(12) United States Patent
Sippy

(10) Patent No.: US 11,858,909 B2
(45) Date of Patent: *Jan. 2, 2024

(54) DEUTERATED ETORICOXIB, METHODS OF MANUFACTURE, AND USE THEREOF

(71) Applicant: Tremeau Pharmaceuticals, Inc., Concord, MA (US)

(72) Inventor: Bradford C. Sippy, Acton, MA (US)

(73) Assignee: Tremeau Pharmaceuticals, Inc., Concord, MA (US)

( * ) Notice: Subject to any disclaimer, the term of this patent is extended or adjusted under 35 U.S.C. 154(b) by 232 days.

This patent is subject to a terminal disclaimer.

(21) Appl. No.: 17/459,838

(22) Filed: Aug. 27, 2021

(65) Prior Publication Data

US 2022/0332696 A1  Oct. 20, 2022

Related U.S. Application Data

(63) Continuation of application No. 17/240,446, filed on Apr. 26, 2021, now Pat. No. 11,161,833.

(60) Provisional application No. 63/173,291, filed on Apr. 9, 2021.

(51) Int. Cl.
| | | |
|---|---|---|
| C07D 401/04 | (2006.01) | |
| A61K 9/00 | (2006.01) | |
| A61K 45/06 | (2006.01) | |

(52) U.S. Cl.
CPC .......... *C07D 401/04* (2013.01); *A61K 9/0053* (2013.01); *A61K 45/06* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 4,675,189 A | 6/1987 | Kent et al. | |
| 5,075,109 A | 12/1991 | Tice et al. | |
| 5,133,974 A | 7/1992 | Paradissis et al. | |
| 5,407,686 A | 4/1995 | Patel et al. | |
| 5,474,995 A | 12/1995 | Ducharme et al. | |
| 5,736,152 A | 4/1998 | Dunn | |
| 5,840,924 A | 11/1998 | Desmond et al. | |
| 5,849,943 A | 12/1998 | Atkinson et al. | |
| 6,063,811 A | 5/2000 | Hancock et al. | |
| 6,407,686 B1 | 6/2002 | Otani et al. | |
| 8,329,216 B2 | 12/2012 | Kao et al. | |
| 8,916,195 B2 | 12/2014 | McKinney et al. | |
| 9,492,408 B2 | 11/2016 | Leikauf | |
| 9,511,037 B2 | 12/2016 | Desai | |
| 10,076,522 B2 | 9/2018 | Huang et al. | |
| 10,376,463 B2 | 8/2019 | Jaffe et al. | |
| 10,564,169 B2 | 2/2020 | Frantz | |
| 10,945,992 B1 | 3/2021 | Sippy et al. | |
| 10,987,337 B2 | 4/2021 | Sippy et al. | |
| 11,161,833 B1 | 11/2021 | Sippy | |
| 2002/0049233 A1 | 4/2002 | Kararli et al. | |
| 2004/0186155 A1 | 9/2004 | Dayno et al. | |
| 2005/0049291 A1 | 3/2005 | Kumar et al. | |
| 2009/0076087 A1 | 3/2009 | Czarnik | |
| 2020/0206182 A1 | 7/2020 | Sippy et al. | |
| 2021/0137878 A1 | 5/2021 | Sippy et al. | |
| 2021/0169845 A1 | 6/2021 | Sippy et al. | |
| 2021/0236455 A1 | 8/2021 | Skwierczynski et al. | |

FOREIGN PATENT DOCUMENTS

| | | |
|---|---|---|
| EP | 754687 A1 | 1/1997 |
| EP | 822190 A1 | 2/1998 |
| EP | 705254 B1 | 5/1998 |
| EP | 980866 A2 | 2/2000 |
| JP | 2000-38375 A | 2/2000 |
| WO | WO 1995/000501 A2 | 1/1995 |
| WO | WO 1995/018799 A1 | 7/1995 |
| WO | WO 1996/008482 A1 | 3/1996 |
| WO | WO 1996/013483 A1 | 5/1996 |
| WO | WO 1997/044028 A1 | 11/1997 |
| WO | WO 1998/000416 A1 | 1/1998 |
| WO | WO 2004/072057 A1 | 8/2004 |
| WO | WO 2005/004806 A2 | 1/2005 |
| WO | WO 2005/016906 A1 | 2/2005 |
| WO | WO 2005/025564 A1 | 3/2005 |
| WO | WO 2005/085199 A1 | 9/2005 |
| WO | WO 2010/033179 A1 | 3/2010 |
| WO | WO 2012/004677 A1 | 1/2012 |
| WO | WO 2019/193417 A1 | 10/2019 |

(Continued)

OTHER PUBLICATIONS

International Search Report and Written Opinion for Application No. PCT/US2022/023900, dated Aug. 29, 2022.

Koniarczyk et al., A General Strategy for Site-Selective Incorporation of Deuterium and Tritium into Pyridines, Diazines, and Pharmaceuticals. J Am Chem Soc. Feb. 14, 2018;140(6):1990-1993. doi: 10.1021/jacs.7b11710. Epub Feb. 5, 2018.

Scheigetz et al., Base-catalyzed deuterium and tritium labeling of aryl methyl sulfones. J Label Compd Radiopharm. 2004; 47:881-889.

Yang et al., Site-Selective Nickel-Catalyzed Hydrogen Isotope Exchange in N-Heterocycles and Its Application to the Tritiation of Pharmaceuticals. ACS Catalysis. Sep. 2018; 8(11):10210-10218. DOI:10.1021/acscatal.8b03717.

(Continued)

*Primary Examiner* — Brian J Davis
(74) *Attorney, Agent, or Firm* — Wolf, Greenfield & Sacks, P.C.

(57) ABSTRACT

Disclosed herein are compounds, such as compounds of Formulae (I), (II), and (III), and d3-etoricoxib, and pharmaceutically acceptable salts, hydrates, solvates, polymorphs, co-crystals, metabolites, and prodrugs thereof, and compositions, methods, uses, and kits thereof. The compounds disclosed herein are COX inhibitors and are therefore useful for the treatment and/or prevention of various conditions (e.g., inflammation, pain, or fever).

31 Claims, 17 Drawing Sheets

(56) References Cited

FOREIGN PATENT DOCUMENTS

WO    WO 2020/106522 A1    5/2020

OTHER PUBLICATIONS

Zarate et al., Ni(I)-X Complexes Bearing a Bulky α-Diimine Ligand: Synthesis, Structure, and Superior Catalytic Performance in the Hydrogen Isotope Exchange in Pharmaceuticals. J Am Chem Soc. Mar. 27, 2019;141(12):5034-5044. doi: 10.1021/jacs.9b00939. Epub Mar. 13, 2019.
International Search Report and Written Opinion, dated Feb. 10, 2021, in connection with Application No. PCT/US2020/060152.
International Search Report and Written Opinion, dated Apr. 14, 2020, in connection with Application No. PCT/US2019/061178.
International Preliminary Report on Patentability, dated Jun. 3, 2021, in connection with Application No. PCT/US2019/061178.
[No Author Listed], An Overview of USP Monographs. Retrieved from usp.org/publicstandards. 2 pages. No Date.
[No Author Listed], Analysis and Recommendations for Agency Action Regarding Nonsteroidal Anti-Inflammatory Drugs and Cardiovascular Risk. J Pain Palliat Car Pharmacother. 2005;19(4):83-97.
[No Author Listed], CSD Entry: CAXMUJ. Retrieved from www.ccdc/cam.acuk/structures/Search?Compound=Rofecoxib&DatabaseToSearch=Published. Accessed May 27, 2020.
[No Author Listed], Etoricoxib—Final Authorized Version 2.0. USPC Medicines Compendium. 6 pages. Retrieved from mc.usp.org/monographs/etoricoxiv-2-0 on Jul. 4, 2020. 6 pages.
[No Author Listed], Etoricoxib D4. Cat. No. HY-15321S. Way Back Machine. Jul. 14, 2017. Retrieved from https://web.archive.org/web/20170714153902/https:/www.medchemexpress.com/Etoricoxib-D4.html. First published on Apr. 10, 2016. 1 page.
[No Author Listed], First Supplement to USP 35-NF 30. Official Monographs / Celecoxib. The United States Pharmacopeial Convention. Aug. 1, 2012:5447-5448.
[No Author Listed], Guidance for Industry—ANDAs: Impurities in Drug Substances. US Department of Health and Human Services. Food and Drug Administration, Center for Drug Evaluation and Research (CDER). Nov. 1999. 19 pages.
[No Author Listed], Guideline on the Limits of Genotoxic Impurities. EMEA/CHMP/QWP/251344/2006. Jun. 28, 2006. 8 pages.
[No Author Listed], M7 Assessment and Control of DNA reactive (Mutagenic) Impurities in Pharmaceuticals to Limit Potential Carcinogenic Risk: Guidance for Industry. US Department of Health and Human Services, Food and Drug Administration, Center for Drug Evaluation and Research (CDER), Center for Biologics Evaluation and Research (CBER). May 2015. 35 pages.
[No Author Listed], M7 Assessment and Control of DNA reactive (Mutagenic) Impurities in Pharmaceuticals to Limit Potential Carcinogenic Risk: Guidance for Industry. US Department of Health and Human Services, Food and Drug Administration, Center for Drug Evaluation and Research (CDER), Center for Biologics Evaluation and Research (CBER). Mar. 2018. 131 pages.
[No Author Listed], Safety Data Sheet for 1,8-Diazabicyclo[5.4.0]undec-7-ene. Cat Nos. ac160610000; ac160610025; ac160610050; ac160610250; ac160611000; ac160615000. ThermoFisher Scientific. Jan. 18, 2018. 7 pages.
[No Author Listed], Safety Data Sheet for 3-Chloroperoxybenzoic acid. Cat Nos. AC255790000; AC255790010' AC255790250; AC255791000; AC255795000. ThermoFisher Scientific. Jan. 23, 2009. 8 pages.
[No Author Listed], Safety Data Sheet for Acetyl chloride. Cat Nos. A27-250. ThermoFisher Scientific. Apr. 25, 2019. 8 pages.
[No Author Listed], Safety Data Sheet for Aluminium chloride. Cat Nos. AC217460000; AC217460025; AC217460050; AC217461000; AC217465000. ThermoFisher Scientific. May 27, 2019. 7 pages.

[No Author Listed], Australian Product Information: Arcoxia® (etoricoxib). Reference ID MK0663-AUS-2017-015150. Retrieved from http://apps.medicines.org.au/files/mkparcox.pdf on Apr. 9, 2021. 27 pages.
[No Author Listed], Vioxx (rofecoxib tablets and oral suspension). Prescribing Information. Reference ID 3928121. Retrieved from https://www.accessdata.fda.gov/drugsatfda_docs/label/2016/021042s033,021052s024lbl.pdf on Dec. 18, 2020. 31 pages.
[No Author Listed], Vioxx (Rofecoxib)—Food and Drug Adminstration Office of Clinical Pharmacology and Biopharmaceutics Review. NDAs 21-042/(SE5-026) & 21-052/(SE5-019). Merck & Co., Inc., Sponsor. Retrieved from www.fda.gov/media/91448/download. 2004. 28 pages (redacted).
[No Author Listed], Vioxx (Rofecoxib)—US Prescribing Information. US Food and Drug Administration, Reference ID: 3928121. Retrieved from www.accessdata.fda.gov/drugsatfda_docs/label/2016/021042s033,021052s024lbl.pdf. 2002. 31 pages.
[No Author Listed], Vioxx® Label. Retrieved from www.accessdata.fda.gov/drugsatfda_docs/label/2004/21647_vioxx_lbl.pdf on May 19, 2021. Mar. 26, 2004. 28 pages.
Abou-Taleb et al., Formulation and Evaluation of Rofecoxib Tablets in Comparison with Marketed Product. Saudi Pharmaceutical Journal. Jul.-Oct. 2006;14(3-4):187-195.
Advisory Action for U.S. Appl. No. 16/867,514, dated Nov. 25, 2020. 116 pages.
Ahuja et al., Rofecoxib: an update on physicochemical, pharmaceutical, pharmacodynamic and pharmacokinetic aspects. J Pharm Pharmacol. Jul. 2003;55(7):859-94. doi: 10.1211/0022357021387.
Andrews et al., A comparison of the Mutagenic Properties of Vinyl Chloride and Methyl Chloride. Mutation Research. 1976;40:273-275.
Azuma et al., Mutagenicity of 12 HPLC Labeling Reagents for Analysing Carboxyl Compounds. J Environ Chem. 1997;7(2):249-255. Abstract Only.
Berge et al., Pharmaceutical Salts. J Pharma Sci. Jan. 1977;66(1):1-19.
Bresalier et al., Cardiovascular Events Associated with Rofecoxib in a Colorectal Adenoma Chemoprevention Trial. N Engl J Med. 2005;352:1092-1102.
Caturla et al., Racemic and chiral sulfoxides as potential prodrugs of the COX-2 inhibitors Vioxx® and Arcoxia®. Bioorg Med Chem Lett. Apr. 17, 2006;16:3209-3212.
Chan et al., Rofecoxib [Vioxx, MK-0966; 4-(4'-Methylsulfonylphenyl)-3--phenyl-2-(5H)-furanone]: a Potent and Orally Active Cyclooxygenase-2 Inhibitor. Pharmacological and Biochemical Profiles. J Pharmacol and Exp Ther. 1999;290(2):551-560.
Davies et al., Pharmacokinetics of Rofecoxib: A Specific Cyclo-Oxygenase-2 Inhibitor. Clin Pharmacokinet. 2003;42(6):545-556.
Dean, Structural Examination of 6-Methylsulphonylphenanthro-[9,10-C]-furan-1(3H)-one—A Rofecoxib Degradation Product. Pharmaceuticals. Feb. 1, 2010;3(3):369-378.
Dembo et al., Central nervous system concentrations of cyclooxygenase-2 inhibitors in humans. Anesthesiology. Feb. 2005;102(2):409-15. doi: 10.1097/00000542-200502000-00026.
Dobo et al., In silico methods combined with expert knowledge rule out mutagenic potential of pharmaceutical impurities: an industry survey. Regulatory Toxicology and Pharmacology. Jan. 31, 2012;62(3):449-455.
Dong et al., Manganese-Catalyzed Selective Oxidation of Aliphatic C—H groups and Secondary Alcohols to Ketones with Hydrogen Peroxide. ChemSusCHem. 2013;6(9):1774-1778.
El-Say et al., Formulation and Evaluation of Rofecoxib Liquisolid Tablets. Int J Pharma Sci Rev Res. Jul.-Aug. 2010;3(Article 028, Issue 1):135-142.
El-Say et al., Optimization of Rofecoxib Liquisolid Tablets using Box-Behnken Design and Desirability Function. J Pharma Res. Oct. 10, 2010;3(10):2388-2392.
Erk et al., Comparison of derivative spectrophotometric and liquid chromatographic methods for the determination of rofecoxib. Pharmazie. Jun. 2004;59(6):453-6.
European Medicines Agency, Note for Guidance on Impurities Testing: Impurities in New Drug Substances. EMEA. Retrieved from www.emea.europa.eu. Oct. 2006. 15 pages.

(56) References Cited

OTHER PUBLICATIONS

Forgione et al., Magnesium mediated carbometallation of propargyl alcohols: direct routes to furans and furanones. Tetra Lett. 2000;41:17-20.

Garde, 'I just white-knuckler it': Hemophilia patients pin their hopes on the revival of Vioxx to fill a void in pain relief. STAT. Dec. 9, 2020. 6 pages.

Groom et al., The Cambridge Structural Database. Acta Cryst. 2016;B72:171-179.

Hansen et al., Benchmark Data Set for in Silico Prediction of Ames Mutagenicity. J Chem Info Model. 2009;49:2077-2081.

Hassan et al., Headaches in vonwillebrand disease. J Haematol Blood Diseases Disorders. Feb. 2014;2(2):023-025. Accessible at www.internationalscholarsjournals.org.

Jenkins et al., Analysis and recommendation for Agency action regarding non-steroidal anti-inflammatory drugs and cardiovascular risk. Memorandum to NDA files 20-998, 21-156, 21-341, 21-042. Apr. 6, 2005. 19 pages.

Koytchev et al., Bioequivalence Study of Rofecoxib Tablets. Arzneim-Forsch/Drug Res. 2004;54(9a):624-628.

Krauskopf, Merck agrees to pay $4.85 billion in Vioxx settlement. Reuters, Business News. Nov. 9, 2007. 6 pages.

Kubota et al., An Unexpected Incident with m-CPBA. Organic Process Research & Development. 2004;8:1076-7078.

Langer, New Methods of Drug Delivery. Science. Sep. 28, 1990;249:1527-1533.

Leber et al., p-Chlorophenyl Methyl Sulfide, p-Chlorophenyl Methyl Sulfoxide, and p-Chlorophenyl Methyls Sulfone. I. Acute Toxicity and Bacterial Mutagenacity Studies. J Am Coll Toxicol. 1993;12(4):369-376.

Leebeek et al., Von Willebrand's Disease. N Engl J Med. Nov. 24, 2016;375(21):2067-2080. doi: 10.1056/NEJMra1601561.

Lenzer, FDA is incapable of protecting US 'against another Vioxx'. BMJ. Nov. 27, 2004;329:1253.

Mao et al., Mao B, Abrahim A, Ge Z, Ellison DK, Hartman R, Prabhu SV, Reamer RA, Wyvratt J. Examination of rofecoxib solution decomposition under alkaline and photolytic stress conditions. J Pharm Biomed Anal. Jun. 15, 2002;28(6):1101-13. doi: 10.1016/s0731-7085(01)00716-6.

Martin, User's Guide for T.E.S.T. (version 4.2) (Toxicity Estimation Software Tool): A program to estimate toxicity from molecular structure. EPA/600/R-16/058. Version 4.2.1. 2016. 63 pages.

Matthews et al., Combined Use of MC4PC, MDL-QSAR, BioEpisteme, Leadscope PDM, and Derek for WIndows Software to Achieve High-Performance, High-Confidence, Mode of Action-Based Predictions of Chemical Carcinogenesis in Rodents. Toxicol Mech Meth. Oct. 9, 2008;18:189-206.

Matthews et al., Improved procedure for the determination of rofecoxib in human plasma involving 96-well solid-phase extraction and fluorescence detection. J Chromatog A. 2002;949:83-89.

Midgley et al., Phase III randomized trial assessing rofecoxib in the adjuvant setting of colorectal cancer: final results of the VICTOR trial. J Clin Oncol. Oct. 20, 2010;28(30):4575-80. doi: 10.1200/JCO.2010.29.6244. Epub Sep. 13, 2010.

Morrison et al., The Optimal Analgesic Dose of Rofecoxib: Overview of Six Randomized Controlled Trials. Clin Pharmacol. JADA Dec. 2000;131:1729-1737.

Muller et al., A rationale for determining, testing, and controlling specific impurities in pharmaceuticals that possess potential for genotoxicity. Regul Toxicol Pharmcol. 2006;44:198-211.

Nicoll-Griffith et al., Synthesis, Characterization, and Activity of Metabolites Derived from the Cyclooxygenase-2 Inhibitor Rofecoxib (MK-0966, Vioxx™). Bioorg Med Chem Lett. 2000;10:2683-2686.

Porras et al., Abstract PII-89: Single and Multiple Dose Pharmacokinetics (PK): of Rofecoxib (R) in Healthy Subjects. Am Soc Clin Pharm Ther. Abstracts of Papers. 2000 Annual Meeting, Clincial Pharamacology & Therapeutics. 2000;67(2):137. 2 pages.

Rabbaa et al., Bioequivalence Study and Pharmacokinetic Evaluation of Two Brands of Rofecoxib 25mg Tablets in a Lebanese Population. J App Res. 2004;4(4):630-634.

Radhakrishna et al., LC determination of rofecoxib in bulk and pharmaceutical formulations. J Pharm Biomed Anal. Nov. 2001;26(4):617-28. doi: 10.1016/s0731-7085(01)00493-9.

Rajendrakumar et al., Comparative Study on Co-Ground Products of Rofecoxib with ß-Cyclodextrin and its Sulfobutyl Ether-7 Derivative in Solution and in the Solid State. J Incl Phenom Macro Chem. 2004;49:259-266.

Ramana et al., A new approach: Enhancement of solubility of rofecoxib. Asian Journal of Pharmaceutics. Apr. 2008:96-101.

Rattray et al., The Use of Rofecoxib (Vioxx) in the Treatment of Hemophilia. Blood. 2004;104:3097. 6 pages.

Reddy et al., Isolation and Characterisation of process-related impurities in rofecoxib. J Pharma Biomed Anal. 2002;29:355-360.

Reddy et al., Novel approaches for colon cancer prevention by cyclooxygenase-2 inhibitors. J Environ Pathol Toxicol Oncol. 2002;21(2):155-64.

Sammour et al., Formulation and optimization of mouth dissolve tablets containing Rofecoxib solid dispersion. AAPS PharmSciTech. 2006;Article 55, 7(2):E1-E9. 9 pages.

Sathesh Babu et al., Solubility Enhancement of Cox-II Inhibitors by Cosolvency Approach. Dhaka Univ. J Pharm Sci. Dec. 2008;7(2):119-126.

Schwartz et al., Abstract 369: Rofecoxib steady-state pharmacokinetics [PK] in moderate hepatic insufficiency patients (HI). Am J Gastroenterol. Sep. 2000:2519. 2 pages.

Schwartz et al., Pharmacokinetic Evaluation of Rofecoxib: Comparison of Tablet and Suspension Formulations. Clin Drug Invest. 2003;23(8):503-509.

Seedher et al., Solubility enhancement of Cox-2 inhibitors using various solvent systems. AAPS PharmSciTech. 2003;4:(3):Article 3. 9 pages.

Sibbald, Rofecoxib (Vioxx) voluntarily withdrawn from market. Synopsis, CMJA. Oct. 26, 2004;171:1027-1028.

Sobera et al., Rofecoxib. Drugs of the Future. 1998;23(12):1287-1296.

Steinbeck et al., The Chemistry Development Kit (CDK): An open-source Java library for chemo- and bioinformatics. J Chem Info and Comp Sci. 2003;43:493-500.

Sutter et al., Use of in silico systems and expert knowledge for structure-based assessment of potentially mutagenic impurities. Regul Toxicol Pharmacol. Article in Press. 2013;67:39-52. doi: 10.1016/j.yrtph.2013.05.001.

Therien et al., Synthesis of Rofecoxib, (MK 0966, Vioxx®, 4(4'-Methylsulfonylphenyl)-3-Phenyl-2(5H)-Furanone), a selective and orally active inhibitor of cyclooxygenase-2. Synthesis (Stuttgart). 2001;12:1778.

Tsoukas et al., Evaluation of the efficacy and safety of etoricoxib in the treatment of hemophilic arthropathy. Blood. Mar. 2006;107(5):1785-1790. Epub Nov. 15, 2005.

US Food and Drug Administration, Patient-Focused Drug Development Meeting on Chronic Pain. Slideshow presentation dated Jul. 9, 2018. Retrieved from https://www.fda.gov/media/114758/download on May 19, 2021. 48 pages.

US Food and Drug Administration, Vioxx (rofecoxib) Questions and Answers. Retrieved from https://www.fda.gov/drugs/postmarket-drug-safety-information-patients-and-providers/vioxx-rofecoxib-questions-and-answers. Sep. 30, 2004. 3 pages.

Werner et al., Selective and rapid liquid chromatography—mass spectrometry method for the quantification of rofecoxib in pharmacokinetic studies with humans. J Chromatograph B. 2001;760:83-90.

Zeiger et al., *Salmonella* Mutagenicity Tests: V. Results from the Testing of 311 Chemicals. Environ Mol Mutagenesis. 1992;19(Supplement 21):2-141.

U.S. Appl. No. 16/867,514, filed May 5, 2020, Sippy et al.
U.S. Appl. No. 17/127,970, filed Dec. 18, 2020, Sippy et al.
U.S. Appl. No. 17/182,728, filed Feb. 23, 2021, Sippy et al.
U.S. Appl. No. 17/513,281, filed Oct. 28, 2021, Sippy et al.
U.S. Appl. No. 16/716,242, filed Dec. 16, 2019, Sippy et al.
U.S. Appl. No. 17/186,697, filed Feb. 26, 2021, Skwierczynski et al.
U.S. Appl. No. 17/240,446, filed Apr. 26, 2021, Sippy et al.
PCT/US2020/060152, Feb. 10, 2021, International Search Report and Written Opinion.

(56) References Cited

OTHER PUBLICATIONS

PCT/US2019/061178, Apr. 14, 2020, International Search Report and Written Opinion.
PCT/US2019/061178, Jun. 3, 2021, International Preliminary Report on Patentability.
[No Author Listed] Vioxx Final. N-21,042. Merck & Co. May 1999. 22 pages.
[No Author Listed], STN Registry No. 2469242-72-4 [online]. [Entered STN: Sep. 2, 2020]. Retrieved from: Chemical Abstracts Service. 1 page.

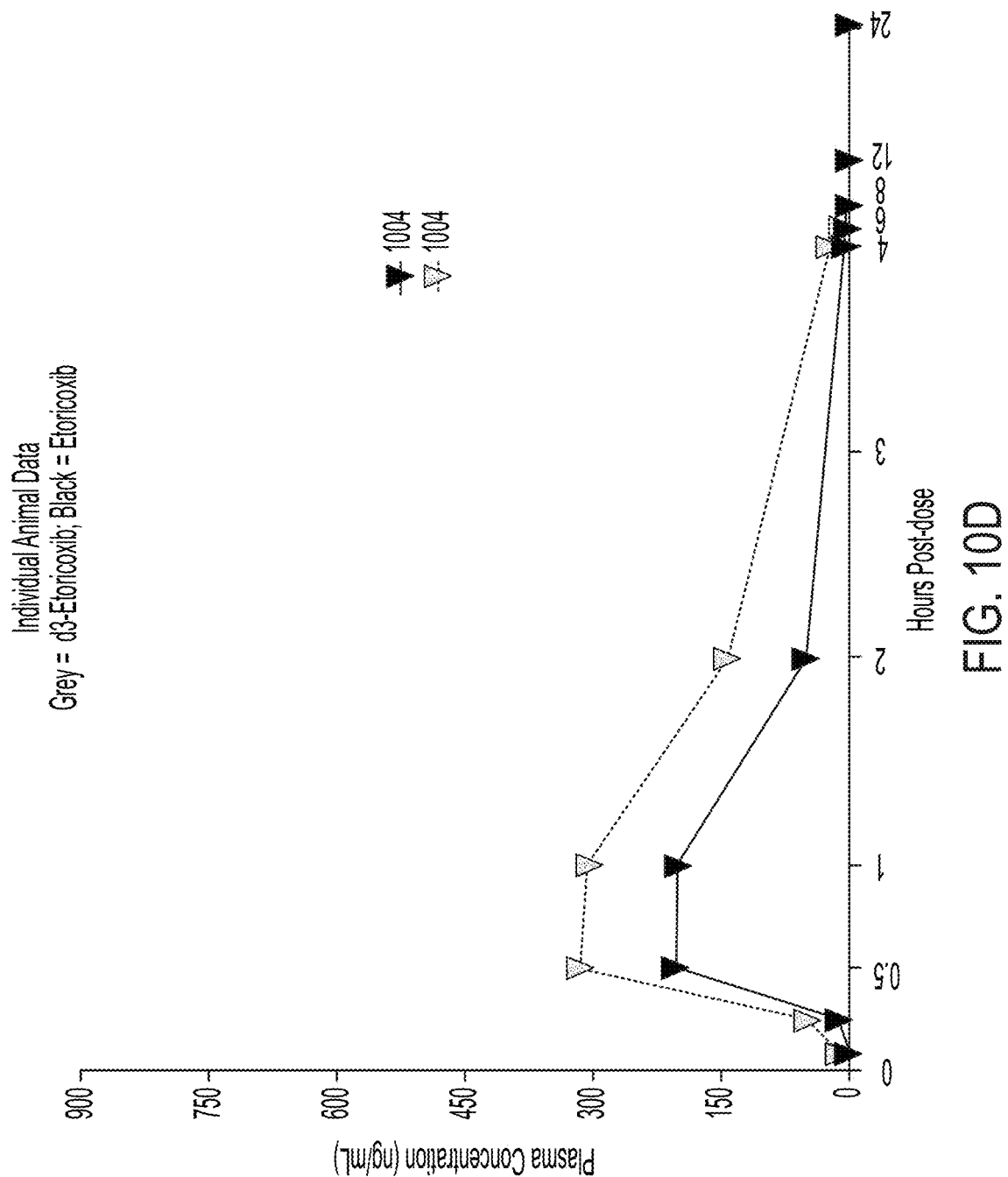

DEUTERATED ETORICOXIB, METHODS OF MANUFACTURE, AND USE THEREOF

CROSS REFERENCE TO RELATED APPLICATIONS

This application is a continuation of U.S. application Ser. No. 17/240,446, filed Apr. 26, 2021, titled DEUTERATED ETORICOXIB, METHODS OF MANUFACTURE, AND USE THEREOF, which claims priority under 35 U.S.C. § 119(e) to U.S. Provisional Application, U.S.S.N. 63/173,291, filed on Apr. 9, 2021, the entire contents of each of the foregoing of which are incorporated herein by reference in their entirety.

BACKGROUND

Etoricoxib (also known by the chemical name 5-chloro-6'-methyl-3-[4-methylsulfonyl)phenyl]-2,3'-bipyridine) is a selective cyclooxygenase 2 (COX-2) inhibitor, nonsteroidal anti-inflammatory drug (NSAID), marketed in numerous jurisdictions under the brand name ARCOXIA®. Etoricoxib has the chemical structure:

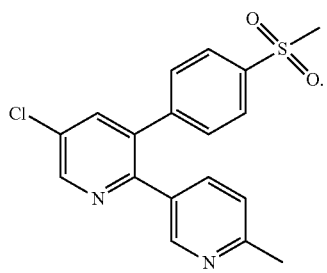 [SMILES: Cc1ccc(-c2ncc(Cl)cc2-c2ccc(S(C)(=O)=O)cc2)cn1]

ARCOXIA® is approved in over 80 countries globally, but was not approved for use in the United States by the Food and Drug Administration. Outside of the United States, ARCOXIA® is approved for indications including acute pain, post-operative pain (e.g., due to dental surgery), chronic musculoskeletal pain, short-term pain (e.g., due to menstrual cramps), pain, fever, or inflammation associated with osteoarthritis, rheumatoid arthritis, psoriatic arthritis, ankylosing spondylitis, and gout.

SUMMARY OF THE INVENTION

Certain novel deuterated forms of etoricoxib have been discovered to have favorable properties. Accordingly, disclosed herein are compositions comprising a deuterated form of etoricoxib, or a pharmaceutically acceptable salt, hydrate, solvate, polymorph, co-crystal, metabolite, or prodrug thereof, as well as methods, and kits comprising the same.

In one aspect, the present disclosure provides a compound of Formula (I):

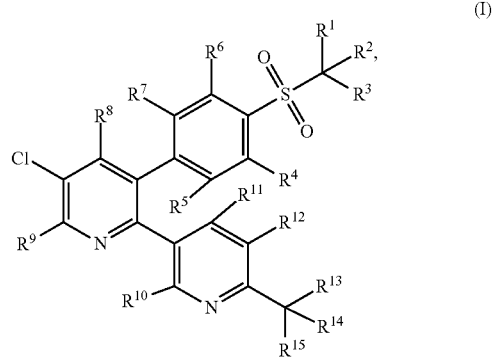

or a pharmaceutically acceptable salt thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined herein, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of Formula (I):

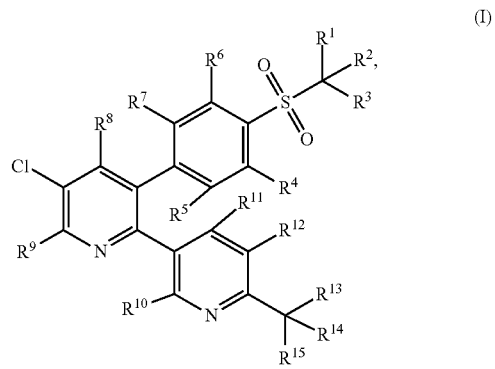

or a pharmaceutically acceptable salt, hydrate, solvate, polymorph, or co-crystal thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined herein, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of Formula (I):

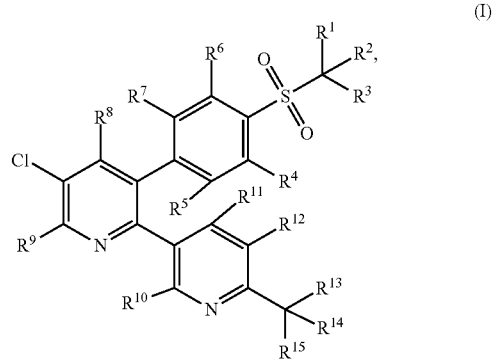

or a pharmaceutically acceptable salt, hydrate, solvate, polymorph, co-crystal, metabolite, or prodrug thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined herein, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of Formula (I):

$R^{15}$ are as defined herein, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides d3-etoricoxib, or a pharmaceutically acceptable salt, hydrate, solvate, polymorph, co-crystal, metabolite, or prodrug thereof. As used herein, "d3-etoricoxib" refers to the compound 5-chloro-6'-(methyl-d3)-3-(4-(methylsulfonyl)phenyl)-2,3'-bipyridine, having the structural formula:

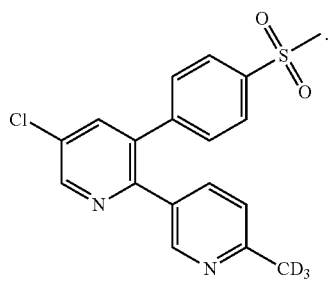 [SMILES: [2H]C([2H])([2H])c1ccc(-c2ncc(Cl)cc2-c2ccc(S(C)(=O)=O)cc2)cn1]

In another aspect, the present disclosure provides a compound of the formula:

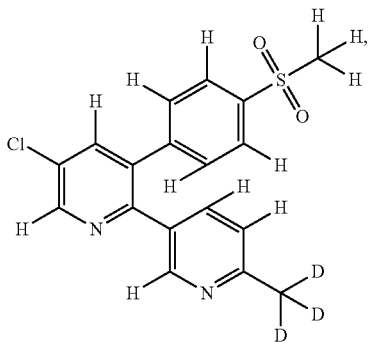

or a pharmaceutically acceptable salt, hydrate, solvate, polymorph, co-crystal, metabolite, or prodrug thereof.

In another aspect, the present disclosure provides a compound of the formula:

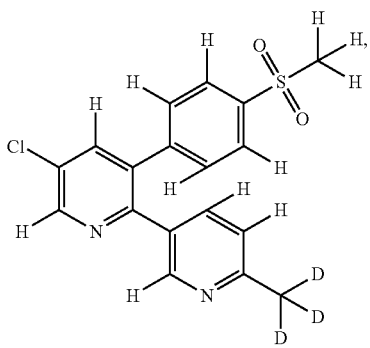

or a pharmaceutically acceptable salt, hydrate, solvate, polymorph, or co-crystal thereof.

In another aspect, the present disclosure provides a compound of the formula:

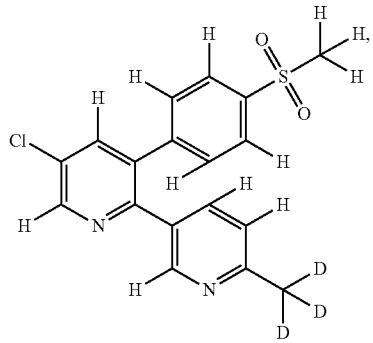

or a pharmaceutically acceptable salt thereof.

In another aspect, the present disclosure provides a compound of Formula (II):

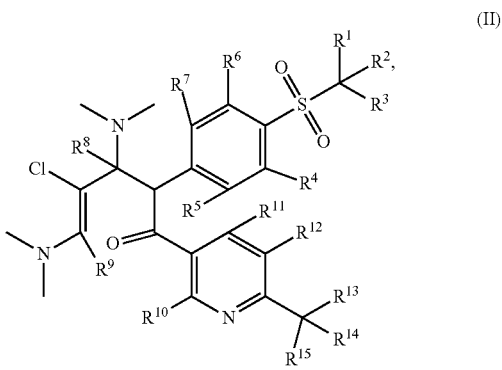

or a salt, hydrate, solvate, polymorph, or co-crystal thereof; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is as defined herein, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of Formula (II):

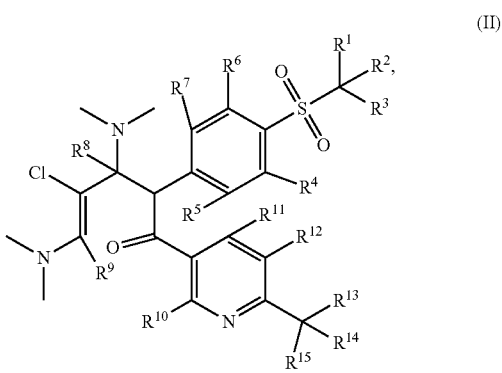

or a salt thereof; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of the formula:

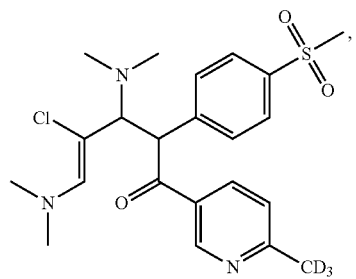

or a pharmaceutically acceptable salt, hydrate, solvate, polymorph, or co-crystal thereof.

In another aspect, the present disclosure provides a compound of the formula:

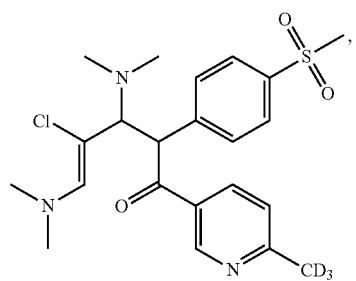

or a pharmaceutically acceptable salt thereof.

In another aspect, the present disclosure provides a compound of Formula (III):

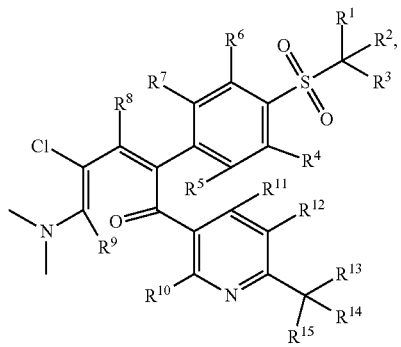

or a salt, hydrate, solvate, polymorph, or co-crystal thereof; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of Formula (III):

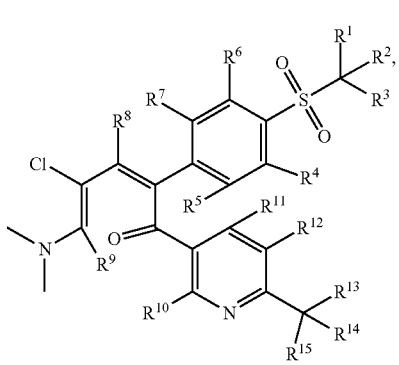

or a salt thereof; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of the formula:

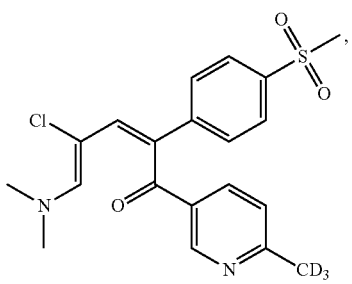

or a salt, hydrate, solvate, polymorph, or co-crystal thereof.

In another aspect, the present disclosure provides a compound of the formula:

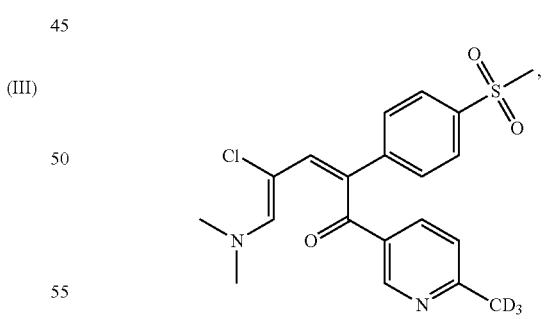

or a salt thereof.

In another aspect, the present disclosure provides a pharmaceutical composition comprising a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof; and a pharmaceutically acceptable excipient.

In another aspect, the present disclosure provides a pharmaceutical composition comprising a compound disclosed herein (e.g., a compound of any one of Formulae (I), (II), or (III), or d3-etoricoxib), or a pharmaceutically acceptable salt, hydrate, solvate, polymorph, or co-crystal thereof; and a pharmaceutically acceptable excipient.

In another aspect, the present disclosure provides a pharmaceutical composition comprising a compound disclosed herein (e.g., a compound of any one of Formulae (I), (II), or (III), or d3-etoricoxib), or a pharmaceutically acceptable salt thereof; and a pharmaceutically acceptable excipient.

In another aspect, the present disclosure provides a pharmaceutical composition comprising a compound of the formula:

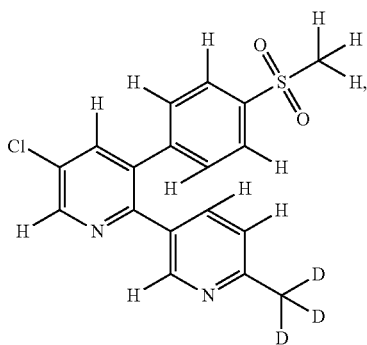

or a pharmaceutically acceptable salt thereof, or a pharmaceutically acceptable salt, hydrate, solvate, polymorph, co-crystal, metabolite, or prodrug thereof; and a pharmaceutically acceptable excipient.

In another aspect, the present disclosure provides a pharmaceutical composition comprising a compound of the formula:

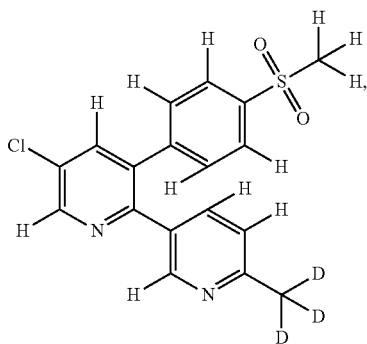

or a pharmaceutically acceptable salt, hydrate, solvate, polymorph, or co-crystal thereof; and a pharmaceutically acceptable excipient.

In another aspect, the present disclosure provides a pharmaceutical composition comprising a compound of the formula:

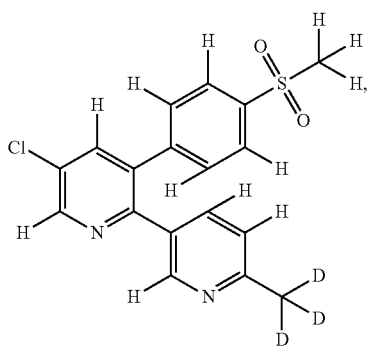

or a pharmaceutically acceptable salt thereof; and a pharmaceutically acceptable excipient.

In another aspect, the present disclosure provides a method for treating pain, fever, or inflammation in a subject in need thereof comprising administering to the subject a therapeutically effective amount of a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof, or a pharmaceutical composition thereof.

In another aspect, the present disclosure provides a method for preventing pain, fever, or inflammation in a subject in need thereof comprising administering to the subject a prophylactically effective amount of a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof, or a pharmaceutical composition thereof.

In another aspect, the present disclosure provides the use of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, in the manufacture of a medicament for treating pain, fever, or inflammation in a subject in need thereof.

In another aspect, the present disclosure provides the use of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, in the manufacture of a medicament for preventing pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in treating pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in preventing pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in therapy.

In another aspect, the present disclosure provides a method of inhibiting cyclooxygenase (COX) activity in vitro comprising contacting a cell, tissue, or biological sample with a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof, or a pharmaceutical composition thereof.

In another aspect, the present disclosure provides the use of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, in the manufacture of a medicament for inhibiting COX-2 activity in a subject in need thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of a compound disclosed herein (e.g., a compound of any one of Formulae (I), (II), or (III), or d3-etoricoxib), or a pharmaceutically acceptable salt, hydrate, solvate, polymorph, or co-crystal thereof, or a pharmaceutical composition thereof.

In another aspect, the present disclosure provides a method for preventing pain, fever, or inflammation in a subject in need thereof comprising administering to the subject a prophylactically effective amount of a compound disclosed herein (e.g., a compound of any one of Formulae (I), (II), or (III), or d3-etoricoxib), or a pharmaceutically acceptable salt, hydrate, solvate, polymorph, or co-crystal thereof, or a pharmaceutical composition thereof.

In another aspect, the present disclosure provides the use of a compound of any one of Formulae (I), (II), or (III), or d3-etoricoxib, or a pharmaceutically acceptable salt, hydrate, solvate, polymorph, or co-crystal thereof, or a pharmaceutical composition thereof, in the manufacture of a medicament for treating pain, fever, or inflammation in a subject in need thereof.

In another aspect, the present disclosure provides the use of a compound of any one of Formulae (I), (II), or (III), or d3-etoricoxib, or a pharmaceutically acceptable salt, hydrate, solvate, polymorph, or co-crystal thereof, or a pharmaceutical composition thereof, in the manufacture of a medicament for preventing pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in treating pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in preventing pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in therapy.

In another aspect, the present disclosure provides a method of inhibiting cyclooxygenase (COX) activity in vitro comprising contacting a cell, tissue, or biological sample with a compound disclosed herein (e.g., a compound of any one of Formulae (I), (II), or (III), or d3-etoricoxib), or a pharmaceutically acceptable salt, hydrate, solvate, polymorph, or co-crystal thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with a compound disclosed herein (e.g., a compound of any one of Formulae (I), (II), or (III), or d3-etoricoxib), or a pharmaceutically acceptable salt, hydrate, solvate, polymorph, or co-crystal thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of a compound disclosed herein (e.g., a compound of any one of Formulae (I), (II), or (III), or d3-etoricoxib), or a pharmaceutically acceptable salt, hydrate, solvate, polymorph, or co-crystal thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of a compound disclosed herein (e.g., a compound of any one of Formulae (I), (II), or (III), or d3-etoricoxib), or a pharmaceutically acceptable salt, hydrate, solvate, polymorph, or co-crystal thereof, or a pharmaceutical composition thereof.

In another aspect, the present disclosure provides the use of a compound of any one of Formulae (I), (II), or (III), or d3-etoricoxib, or a pharmaceutically acceptable salt, hydrate, solvate, polymorph, or co-crystal thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of a compound of any one of Formulae (I), (II), or (III), or d3-etoricoxib, or a pharmaceutically acceptable salt, hydrate, solvate, polymorph, or co-crystal thereof, or a pharmaceutical composition thereof, in the manufacture of a medicament for inhibiting COX-2 activity in a subject in need thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of a compound disclosed herein (e.g., a compound of any one of Formulae (I), (II), or (III), or d3-etoricoxib), or a pharmaceutically acceptable salt thereof, or a pharmaceutical composition thereof.

In another aspect, the present disclosure provides a method for preventing pain, fever, or inflammation in a subject in need thereof comprising administering to the subject a prophylactically effective amount of a compound disclosed herein (e.g., a compound of any one of Formulae (I), (II), or (III), or d3-etoricoxib), or a pharmaceutically acceptable salt thereof, or a pharmaceutical composition thereof.

In another aspect, the present disclosure provides the use of a compound of any one of Formulae (I), (II), or (III), or d3-etoricoxib, or a pharmaceutically acceptable salt thereof, or a pharmaceutical composition thereof, in the manufacture of a medicament for treating pain, fever, or inflammation in a subject in need thereof.

In another aspect, the present disclosure provides the use of a compound of any one of Formulae (I), (II), or (III), or d3-etoricoxib, or a pharmaceutically acceptable salt thereof, or a pharmaceutical composition thereof, in the manufacture of a medicament for preventing pain, fever, or inflammation in a subject in need thereof.

In another aspect, the present disclosure provides a compound of any one of Formulae (I), (II), or (III), or d3-etoricoxib, or a pharmaceutically acceptable salt thereof, or a pharmaceutical composition thereof, for use in treating pain, fever, or inflammation in a subject in need thereof.

In another aspect, the present disclosure provides a compound of any one of Formulae (I), (II), or (III), or d3-etoricoxib, or a pharmaceutically acceptable salt thereof, or a pharmaceutical composition thereof, for use in preventing pain, fever, or inflammation in a subject in need thereof.

In another aspect, the present disclosure provides a compound of any one of Formulae (I), (II), or (III), or d3-etoricoxib, or a pharmaceutically acceptable salt thereof, or a pharmaceutical composition thereof, for use in therapy.

In yet another aspect, the present disclosure provides a method of inhibiting cyclooxygenase (COX) activity in vitro comprising contacting a cell, tissue, or biological sample with a compound disclosed herein (e.g., a compound of any one of Formulae (I), (II), or (III), or d3-etoricoxib), or a pharmaceutically acceptable salt thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with a compound disclosed herein (e.g., a compound of any one of Formulae (I), (II), or (III), or d3-etoricoxib), or a pharmaceutically acceptable salt thereof.

In another aspect, the present disclosure provides a compound of any one of Formulae (I), (II), or (III), or d3-etoricoxib, or a pharmaceutically acceptable salt thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of a compound disclosed herein (e.g., a compound of any one of Formulae (I), (II), or (III), or d3-etoricoxib), or a pharmaceutically acceptable salt thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of a compound disclosed herein (e.g., a compound of any one of Formulae (I), (II), or (III), or d3-etoricoxib), or a pharmaceutically acceptable salt thereof, or a pharmaceutical composition thereof.

In another aspect, the present disclosure provides the use of a compound of any one of Formulae (I), (II), or (III), or d3-etoricoxib, or a pharmaceutically acceptable salt thereof, or a pharmaceutical composition thereof, in the manufacture of a medicament for inhibiting cyclooxygenase activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of a compound of any one of Formulae (I), (II), or (III), or d3-etoricoxib, or a pharmaceutically acceptable salt thereof, or a pharmaceutical composition thereof, in the manufacture of a medicament for inhibiting COX-2 activity in a subject in need thereof.

In another aspect, the present disclosure provides a compound of any one of Formulae (I), (II), or (III), or d3-etoricoxib, or a pharmaceutically acceptable salt thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of d3-etoricoxib, or a pharmaceutically acceptable salt, hydrate, solvate, polymorph, co-crystal, metabolite, or prodrug thereof, or a pharmaceutical composition thereof.

In another aspect, the present disclosure provides a method for preventing pain, fever, or inflammation in a subject in need thereof comprising administering to the subject a prophylactically effective amount of d3-etoricoxib, or a pharmaceutically acceptable salt, hydrate, solvate, polymorph, co-crystal, metabolite, or prodrug thereof, or a pharmaceutical composition thereof.

In another aspect, the present disclosure provides the use of d3-etoricoxib, or a pharmaceutically acceptable salt, hydrate, solvate, polymorph, co-crystal, metabolite, or prodrug thereof, or a pharmaceutical composition thereof, in the manufacture of a medicament for treating pain, fever, or inflammation in a subject in need thereof.

In another aspect, the present disclosure provides the use of d3-etoricoxib, or a pharmaceutically acceptable salt, hydrate, solvate, polymorph, co-crystal, metabolite, or prodrug thereof, or a pharmaceutical composition thereof, in the manufacture of a medicament for preventing pain, fever, or inflammation in a subject in need thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in treating pain, fever, or inflammation in a subject in need thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in preventing pain, fever, or inflammation in a subject in need thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in therapy.

In another aspect, the present disclosure provides a method of inhibiting cyclooxygenase (COX) activity in vitro comprising contacting a cell, tissue, or biological sample with d3-etoricoxib, or a pharmaceutically acceptable salt, hydrate, solvate, polymorph, co-crystal, metabolite, or prodrug thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with d3-etoricoxib, or a pharmaceutically acceptable salt, hydrate, solvate, polymorph, co-crystal, metabolite, or prodrug thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of d3-etoricoxib, or a pharmaceutically acceptable salt, hydrate, solvate, polymorph, co-crystal, metabolite, or prodrug thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of d3-etoricoxib, or a pharmaceutically acceptable salt, hydrate, solvate, polymorph, co-crystal, metabolite, or prodrug thereof, or a pharmaceutical composition thereof.

In another aspect, the present disclosure provides the use of d3-etoricoxib, or a pharmaceutically acceptable salt, hydrate, solvate, polymorph, co-crystal, metabolite, or prodrug thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of d3-etoricoxib, or a pharmaceutically acceptable salt, hydrate, solvate, polymorph, co-crystal, metabolite, or prodrug thereof, or a pharmaceutical composition thereof, in the manufacture of a medicament for inhibiting COX-2 activity in a subject in need thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of d3-etoricoxib, or a pharmaceutically acceptable salt, hydrate, solvate, polymorph, or co-crystal thereof, or a pharmaceutical composition thereof.

In another aspect, the present disclosure provides a method for preventing pain, fever, or inflammation in a subject in need thereof comprising administering to the subject a prophylactically effective amount of d3-etoricoxib, or a pharmaceutically acceptable salt, hydrate, solvate, polymorph, or co-crystal thereof, or a pharmaceutical composition thereof.

In another aspect, the present disclosure provides the use of d3-etoricoxib, or a pharmaceutically acceptable salt, hydrate, solvate, polymorph, or co-crystal thereof, or a pharmaceutical composition thereof, in the manufacture of a medicament for treating pain, fever, or inflammation in a subject in need thereof.

In another aspect, the present disclosure provides the use of d3-etoricoxib, or a pharmaceutically acceptable salt, hydrate, solvate, polymorph, or co-crystal thereof, or a pharmaceutical composition thereof, in the manufacture of a medicament for preventing pain, fever, or inflammation in a subject in need thereof.

In another aspect, the present disclosure provides d3-etoricoxib, or a pharmaceutically acceptable salt, hydrate, solvate, polymorph, or co-crystal thereof, or a pharmaceutical composition thereof, for use in treating pain, fever, or inflammation in a subject in need thereof.

In another aspect, the present disclosure provides d3-etoricoxib, or a pharmaceutically acceptable salt, hydrate, solvate, polymorph, or co-crystal thereof, or a pharmaceutical composition thereof, for use in preventing pain, fever, or inflammation in a subject in need thereof.

In another aspect, the present disclosure provides d3-etoricoxib, or a pharmaceutically acceptable salt, hydrate, solvate, polymorph, or co-crystal thereof, or a pharmaceutical composition thereof, for use in therapy.

In yet another aspect, the present disclosure provides a method of inhibiting cyclooxygenase (COX) activity in vitro comprising contacting a cell, tissue, or biological sample with d3-etoricoxib, or a pharmaceutically acceptable salt, hydrate, solvate, polymorph, or co-crystal thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with d3-etoricoxib, or a pharmaceutically acceptable salt, hydrate, solvate, polymorph, or co-crystal thereof.

In another aspect, the present disclosure provides d3-etoricoxib, or a pharmaceutically acceptable salt, hydrate, solvate, polymorph, or co-crystal thereof, or a pharmaceutical composition thereof, for use in inhibiting cyclooxygenase activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt, hydrate, solvate, polymorph, or co-crystal thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of d3-etoricoxib, or a pharmaceutically acceptable salt, hydrate, solvate, polymorph, or co-crystal thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of d3-etoricoxib, or a pharmaceutically acceptable salt, hydrate, solvate, polymorph, or co-crystal thereof, or a pharmaceutical composition thereof.

In another aspect, the present disclosure provides the use of d3-etoricoxib, or a pharmaceutically acceptable salt, hydrate, solvate, polymorph, or co-crystal thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of d3-etoricoxib, or a pharmaceutically acceptable salt, hydrate, solvate, polymorph, or co-crystal thereof, or a pharmaceutical composition thereof, in the manufacture of a medicament for inhibiting COX-2 activity in a subject in need thereof.

In another aspect, the present disclosure provides d3-etoricoxib, or a pharmaceutically acceptable salt, hydrate, solvate, polymorph, or co-crystal thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt, hydrate, solvate, polymorph, or co-crystal thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of d3-etoricoxib, or a pharmaceutically acceptable salt thereof, or a pharmaceutical composition thereof.

In another aspect, the present disclosure provides a method for preventing pain, fever, or inflammation in a subject in need thereof comprising administering to the subject a prophylactically effective amount of d3-etoricoxib, or a pharmaceutically acceptable salt thereof, or a pharmaceutical composition thereof.

In another aspect, the present disclosure provides the use of d3-etoricoxib, or a pharmaceutically acceptable salt thereof, or a pharmaceutical composition thereof, in the manufacture of a medicament for treating pain, fever, or inflammation in a subject in need thereof.

In another aspect, the present disclosure provides the use of d3-etoricoxib, or a pharmaceutically acceptable salt thereof, or a pharmaceutical composition thereof, in the manufacture of a medicament for preventing pain, fever, or inflammation in a subject in need thereof.

In another aspect, the present disclosure provides d3-etoricoxib, or a pharmaceutically acceptable salt thereof, or a pharmaceutical composition thereof, for use in treating pain, fever, or inflammation in a subject in need thereof.

In another aspect, the present disclosure provides d3-etoricoxib, or a pharmaceutically acceptable salt thereof, or a pharmaceutical composition thereof, for use in preventing pain, fever, or inflammation in a subject in need thereof.

In another aspect, the present disclosure provides d3-etoricoxib, or a pharmaceutically acceptable salt thereof, or a pharmaceutical composition thereof, for use in therapy.

In another aspect, the present disclosure provides a method of inhibiting cyclooxygenase (COX) activity in vitro comprising contacting a cell, tissue, or biological sample with d3-etoricoxib, or a pharmaceutically acceptable salt thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with d3-etoricoxib, or a pharmaceutically acceptable salt thereof.

In another aspect, the present disclosure provides d3-etoricoxib, or a pharmaceutically acceptable salt thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of d3-etoricoxib, or a pharmaceutically acceptable salt thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of d3-etoricoxib, or a pharmaceutically acceptable salt thereof, or a pharmaceutical composition thereof.

In another aspect, the present disclosure provides the use of d3-etoricoxib, or a pharmaceutically acceptable salt thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of d3-etoricoxib, or a pharmaceutically acceptable salt thereof, or a pharmaceutical composition thereof, in the manufacture of a medicament for inhibiting COX-2 activity in a subject in need thereof.

In another aspect, the present disclosure provides d3-etoricoxib, or a pharmaceutically acceptable salt thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt thereof, or a pharmaceutical composition thereof, for use in inhibiting COX-2 activity in a subject in need thereof.

In another aspect, the present disclosure provides a kit comprising a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof; or a pharmaceutical composition thereof; and instructions for using the compound, or a pharmaceutically acceptable salt, hydrate, solvate, polymorph, co-crystal, metabolite, or prodrug thereof, or the pharmaceutical composition.

In another aspect, the present disclosure provides a kit comprising a compound disclosed herein (e.g., a compound of any one of Formulae (I), (II), or (III), or d3-etoricoxib), or a pharmaceutically acceptable salt, hydrate, solvate, polymorph, or co-crystal thereof; or a pharmaceutical composition thereof; and instructions for using the compound, or a pharmaceutically acceptable salt, hydrate, solvate, polymorph, or co-crystal thereof, or the pharmaceutical composition.

In another aspect, the present disclosure provides a kit comprising a compound disclosed herein (e.g., a compound of any one of Formulae (I), (II), or (III), or d3-etoricoxib), or a pharmaceutically acceptable salt thereof; or a pharmaceutical composition thereof; and instructions for using the compound, or a pharmaceutically acceptable salt thereof, or the pharmaceutical composition.

In another aspect, the present disclosure provides a kit comprising a compound of the formula:

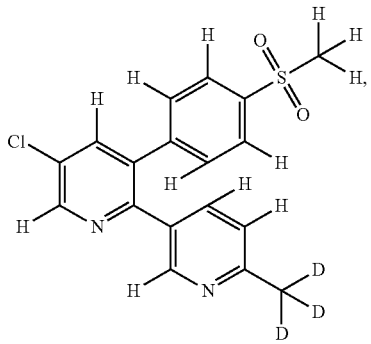

or a pharmaceutically acceptable salt, hydrate, solvate, polymorph, co-crystal, metabolite, or prodrug thereof; or a pharmaceutical composition thereof; and instructions for using the compound, or a pharmaceutically acceptable salt, hydrate, solvate, polymorph, co-crystal, metabolite, or prodrug thereof, or the pharmaceutical composition.

In another aspect, the present disclosure provides a kit comprising a compound of the formula:

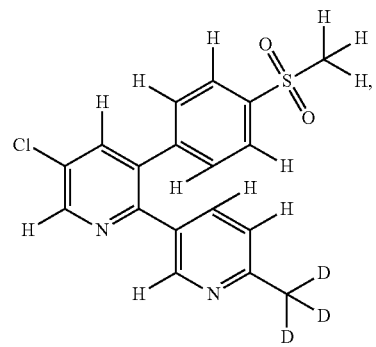

or a pharmaceutically acceptable salt, hydrate, solvate, polymorph, or co-crystal thereof; or a pharmaceutical composition thereof; and instructions for using the compound, or a pharmaceutically acceptable salt, hydrate, solvate, polymorph, or co-crystal thereof, or the pharmaceutical composition.

In another aspect, the present disclosure provides a kit comprising a compound of the formula:

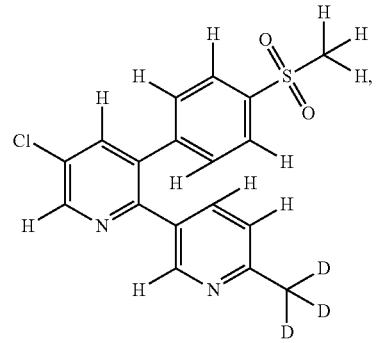

or a pharmaceutically acceptable salt thereof; or a pharmaceutical composition thereof; and instructions for using the compound, or a pharmaceutically acceptable salt thereof, or the pharmaceutical composition.

In another aspect, the present disclosure provides a method of preparing a compound of Formula (I):

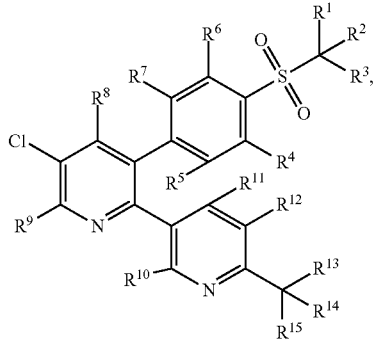
(I)

or a pharmaceutically acceptable salt, hydrate, solvate, polymorph, co-crystal, metabolite, or prodrug thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined herein, the method comprising contacting a compound of Formula (III):

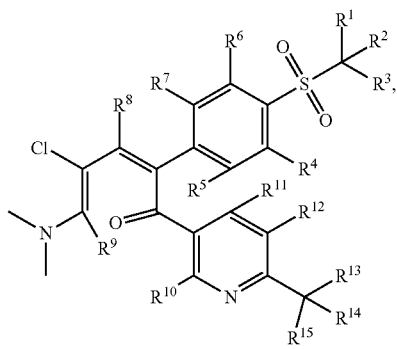
(III)

or a salt, hydrate, solvate, polymorph, or co-crystal thereof with a source of nitrogen to produce the compound of Formula (I), or a pharmaceutically acceptable salt, hydrate, solvate, polymorph, or co-crystal thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined herein.

In another aspect, the present disclosure provides a method of preparing a compound of Formula (I):

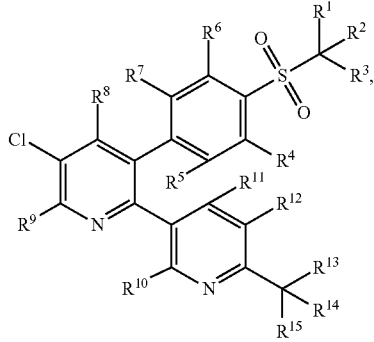
(I)

or a pharmaceutically acceptable salt, hydrate, solvate, polymorph, co-crystal, metabolite, or prodrug thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined herein, the method comprising:

(1) contacting a compound of Formula (II):

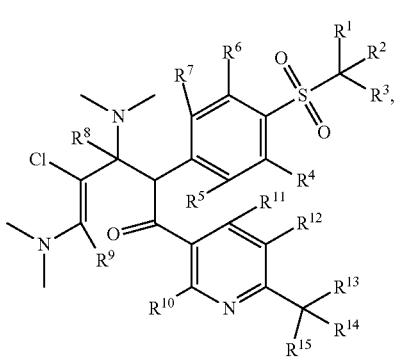
(II)

or a salt, hydrate, solvate, polymorph, or co-crystal thereof with one or more acids to produce a compound of Formula (III):

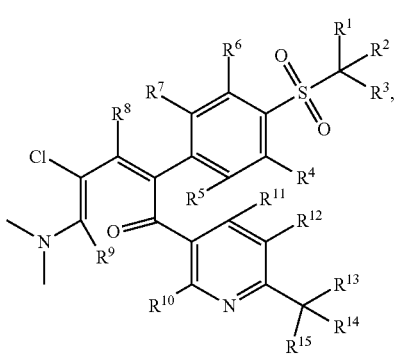
(III)

or a salt, hydrate, solvate, polymorph, or co-crystal thereof; and (2) contacting the compound of Formula (III), or a salt, hydrate, solvate, polymorph, or co-crystal thereof with a source of nitrogen to produce the compound of Formula (I), or a pharmaceutically acceptable salt, hydrate, solvate, polymorph, or co-crystal thereof;

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined herein.

In another aspect, the present disclosure provides a method of preparing a compound of Formula (I):

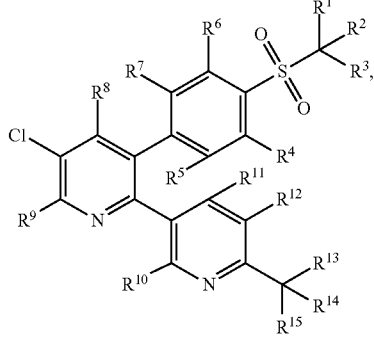

or a pharmaceutically acceptable salt, hydrate, solvate, polymorph, co-crystal, metabolite, or prodrug thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined herein, the method comprising:

(1) contacting a compound of Formula (A):

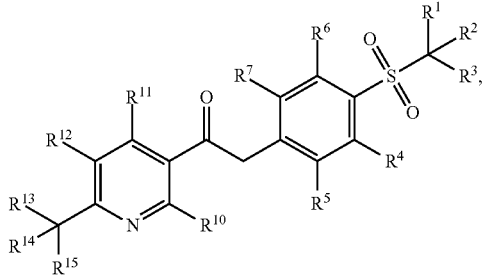

or a salt, hydrate, solvate, polymorph, or co-crystal thereof with one or more bases and a compound of Formula (B):

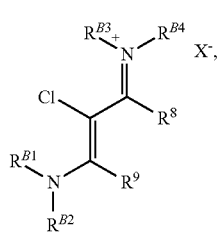

or a salt, hydrate, solvate, polymorph, or co-crystal thereof to produce a compound of Formula (II):

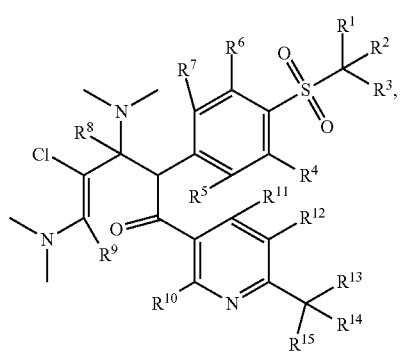

or a salt, hydrate, solvate, polymorph, or co-crystal thereof;

(2) contacting the compound of Formula (II), or a salt, hydrate, solvate, polymorph, or co-crystal thereof with one or more acids to produce a compound of Formula (III):

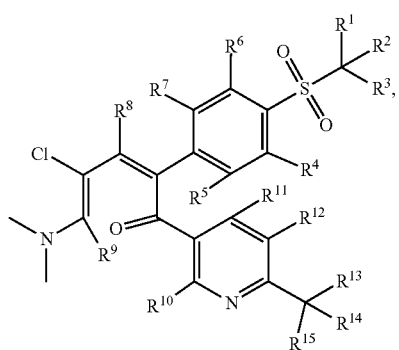

or a salt, hydrate, solvate, polymorph, or co-crystal thereof; and (3) contacting the compound of Formula (III) with a source of nitrogen to produce the compound of Formula (I), or a pharmaceutically acceptable salt, hydrate, solvate, polymorph, or co-crystal thereof;

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{B1}$, $R^{B2}$, $R^{B3}$, $R^{B4}$, and $X^-$ are as defined herein.

In another aspect, the present disclosure provides a method of preparing a compound of Formula (I):

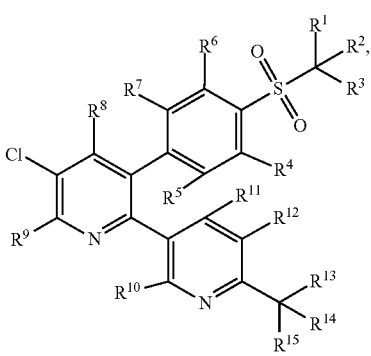

or a pharmaceutically acceptable salt, hydrate, solvate, polymorph, co-crystal, metabolite, or prodrug thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined herein, the method comprising:

(1) contacting a compound of Formula (C):

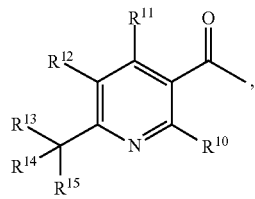

(C)

or a salt, hydrate, solvate, polymorph, or co-crystal thereof with a compound of Formula (D):

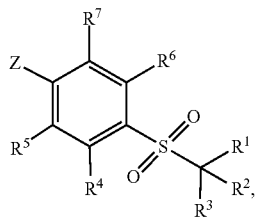

(D)

or a salt, hydrate, solvate, polymorph, or co-crystal thereof to produce a compound of Formula (A):

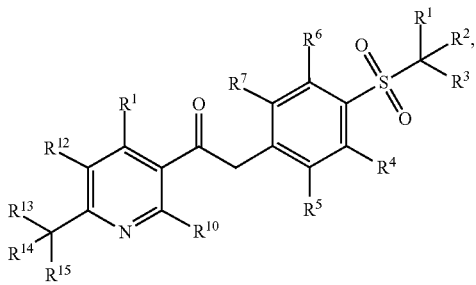

(A)

or a salt, hydrate, solvate, polymorph, or co-crystal thereof;

(2) contacting the compound of Formula (A), or a salt, hydrate, solvate, polymorph, or co-crystal thereof with one or more bases and a compound of Formula (B):

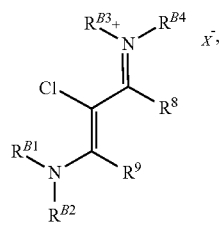

(B)

or a salt, hydrate, solvate, polymorph, or co-crystal thereof to produce a compound of Formula (II):

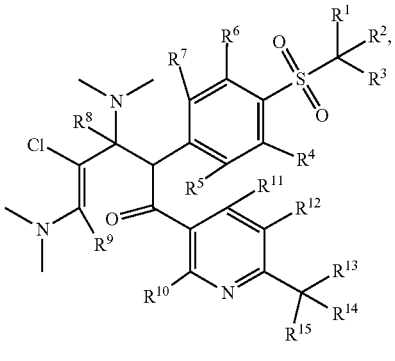

(II)

or a salt, hydrate, solvate, polymorph, or co-crystal thereof;

(3) contacting the compound of Formula (II), or a salt, hydrate, solvate, polymorph, or co-crystal thereof with one or more acids to produce a compound of Formula (III):

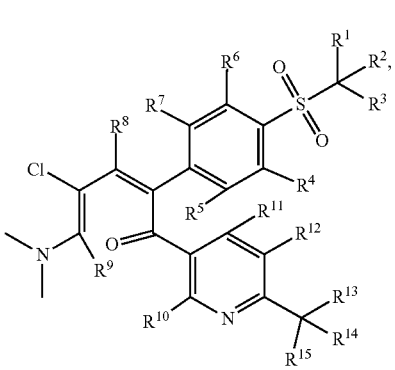

(III)

or a salt, hydrate, solvate, polymorph, or co-crystal thereof; and (4) contacting the compound of Formula (III) with a source of nitrogen to produce the compound of Formula (I), or a pharmaceutically acceptable salt, hydrate, solvate, polymorph, or co-crystal thereof;

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{B1}$, $R^{B2}$, $R^{B3}$, $R^{B4}$, $X^-$, and $Z$ are as defined herein.

The details of certain embodiments of the invention are set forth in the Detailed Description of Certain Embodiments, as described below. Other features, objects, and advantages of the invention will be apparent from the Definitions, Examples, Figures, and Claims. It should be understood that the aspects disclosed herein are not limited to specific embodiments, methods, or configurations, and as such can, of course, vary. It is also to be understood that the terminology used herein is for the purpose of describing particular aspects only and, unless specifically defined herein, is not intended to be limiting.

BRIEF DESCRIPTION OF THE DRAWINGS

The accompanying drawings, which constitute a part of this specification, illustrate several embodiments of the present disclosure and together with the description, provide non-limiting examples of the invention.

FIGS. 10A-D show a comparison of individual mean plasma concentrations of etoricoxib (black trace) and d3-etoricoxib (grey trace) over 24 hours following administration to dogs.

DEFINITIONS

Figure 1:
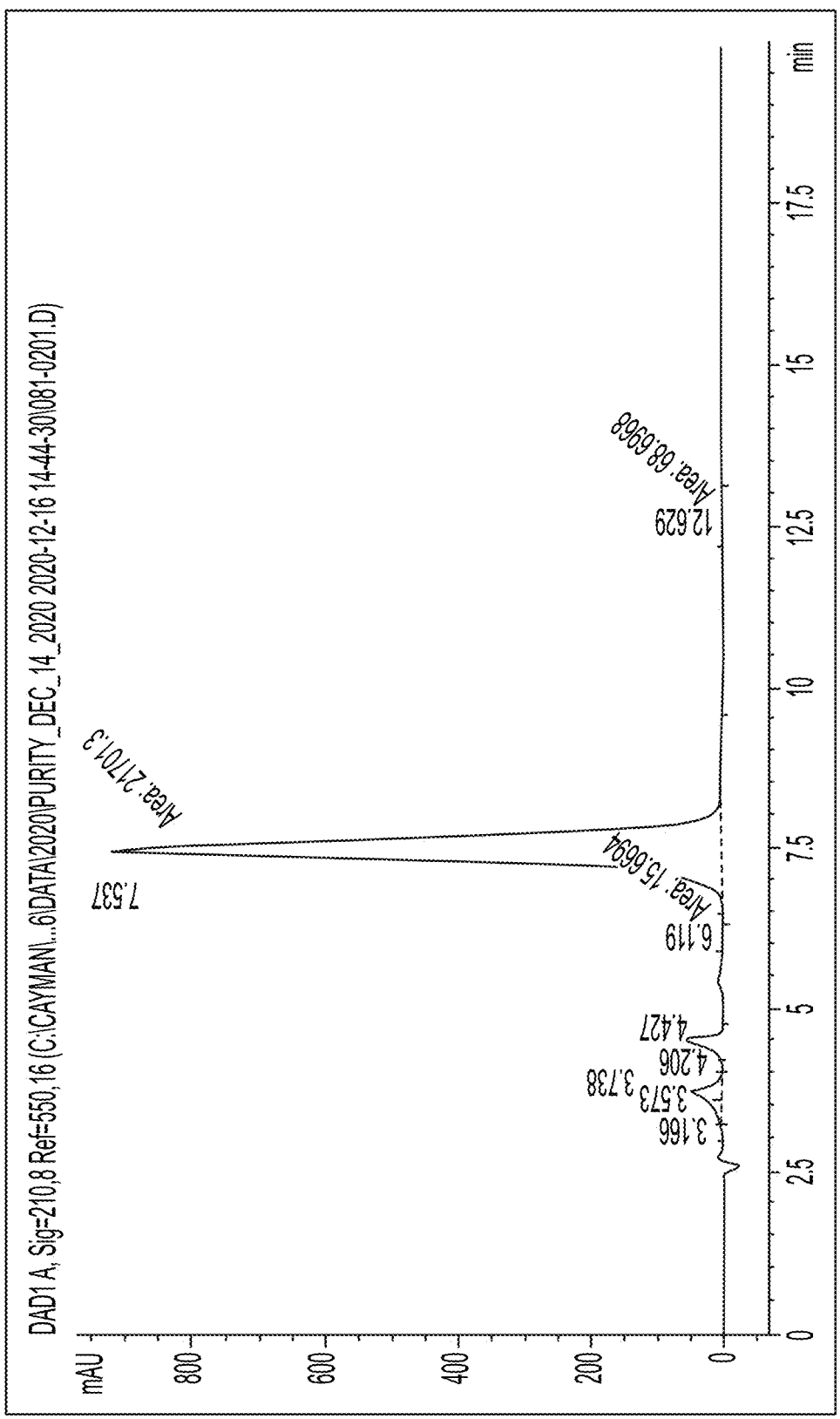
FIG. 1 shows a high performance liquid chromatography ("HPLC") chromatogram of d3-etoricoxib.

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

As used here, "etoricoxib" refers to 5-chloro-6'-methyl-3-[4-methylsulfonyl)pheny]-2,3'-bipyridine, or a pharmaceutically acceptable salt or solvate thereof. Etoricoxib has the chemical structure:

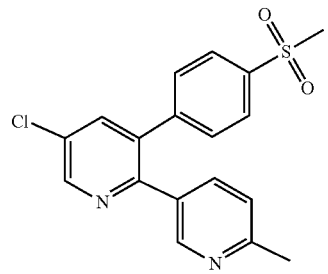

Salts of etoricoxib are described in International Patent Application Publication No. WO 2012/004677 A1 to Actavis Group PTC EHF/Khunt, the contents of which are incorporated herein by reference in their entirety. Polymorphs of etoricoxib are described in International Patent Application Publication No. WO 2005/085199 A1 to Cadila HealthCare Ltd./Lohray, the contents of which are incorporated herein by reference in their entirety.

As used herein, "d3-etoricoxib" refers to the compound 5-chloro-6'-(methyl-d3)-3-(4-(methylsulfonyl) phenyl)-2,3'-bipyridine, having the structural formula:

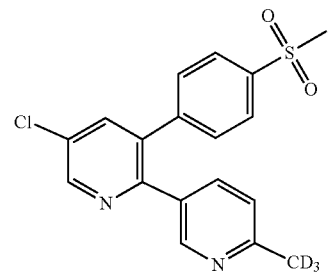

As used herein, the term "salt" refers to any and all salts, and encompasses pharmaceutically acceptable salts. Salts include ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. In some embodiments, this physical association includes hydrogen bonding. Conventional solvents include water, methanol, ethanol, acetic acid, DMSO, THF, diethyl ether, and the like. In some embodiments, the compounds disclosed herein are prepared, e.g., in crystalline form, and are solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "stoichiometric solvate" refers to a solvate, which comprises a compound (e.g., a compound disclosed herein) and a solvent, wherein the solvent molecules are an integral part of the crystal lattice, in which they interact strongly with the compound and each other. The removal of the solvent molecules will cause instability of the crystal network, which subsequently collapses into an amorphous phase or recrystallizes as a new crystalline form with reduced solvent content.

The term "non-stoichiometric solvate" refers to a solvate, which comprises a compound (e.g., a compound disclosed herein) and a solvent. In some embodiments, the solvent content varies without major changes in the crystal structure. The amount of solvent in the crystal lattice only depends on the partial pressure of solvent in the surrounding atmosphere. In the fully solvated state, non-stoichiometric solvates may, but not necessarily have to, show an integer molar ratio of solvent to the compound. In some embodiments, during drying of a non-stoichiometric solvate, a portion of the solvent is removed without significantly disturbing the crystal network, and the resulting solvate can subsequently be resolvated to give the initial crystalline form. Unlike stoichiometric solvates, the desolvation and resolvation of non-stoichiometric solvates is not accompanied by a phase transition, and all solvation states represent the same crystal form.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. In some embodiments, a given compound forms more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "crystalline" or "crystalline form" refers to a solid form substantially exhibiting long-range three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks. In some embodiments, the composition comprises one or more crystalline forms.

The term "amorphous" or "amorphous form" refers to a form of a solid ("solid form"), the form substantially lacking three-dimensional order. In certain embodiments, an amorphous form of a solid is a solid form that is substantially not crystalline. In certain embodiments, the X-ray powder diffraction (XRPD) pattern of an amorphous form includes a wide scattering band with a peak at $2\theta$ of, e.g., between 20 and 70°, inclusive, using CuKα radiation. In certain embodiments, the XRPD pattern of an amorphous form further includes one or more peaks attributed to crystalline structures. In certain embodiments, the maximum intensity of any one of the one or more peaks attributed to crystalline structures observed at a $2\theta$ of between 20 and 70°, inclusive, is not more than 300-fold, not more than 100-fold, not more than 30-fold, not more than 10-fold, or not more than 3-fold of the maximum intensity of the wide scattering band. In certain embodiments, the XRPD pattern of an amorphous form includes no peaks attributed to crystalline structures.

The term "co-crystal" refers to a crystalline structure comprising at least two different components (e.g., a compound disclosed herein and an acid), wherein each of the components is independently an atom, ion, or molecule. In certain embodiments, none of the components is a solvent. In certain embodiments, at least one of the components is a solvent. A co-crystal of a compound disclosed herein and an acid is different from a salt formed from a compound disclosed herein and the acid. In the salt, a compound disclosed herein is complexed with the acid in a way that proton transfer (e.g., a complete proton transfer) from the acid to a compound disclosed herein easily occurs at room temperature. In the co-crystal, however, a compound disclosed herein is complexed with the acid in a way that proton transfer from the acid to a compound disclosed herein does not easily occur at room temperature. In certain embodiments, in the co-crystal, there is no proton transfer from the acid to a compound disclosed herein. In certain embodiments, in the co-crystal, there is partial proton transfer from the acid to a compound disclosed herein. In some embodiments, co-crystals improve the properties (e.g., solubility, stability, and ease of formulation) of a compound disclosed herein.

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. In some embodiments, recrystallization solvent, rate of crystallization, storage temperature, and other factors cause one crystal form to dominate. In some embodiments, various polymorphs of a compound are prepared by crystallization under different conditions.

The term "prodrug" as employed herein denotes a compound that, upon administration to a subject, undergoes chemical conversion by metabolic or chemical processes to yield a compound of the present subject matter, or a salt and/or solvate thereof.

The term "isotopes" refers to variants of a particular chemical element such that, while all isotopes of a given element share the same number of protons in each atom of the element, those isotopes differ in the number of neutrons. Deuterium is a stable isotope of hydrogen with a nucleus consisting of one proton and one neutron.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)).

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which is substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not limited in any manner by the exemplary substituents described herein.

Exemplary carbon atom substituents include halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(=O)$R^{aa}$, —$CO_2H$, —CHO, —C(OR^{cc})_2, —$CO_2R^{aa}$, —OC(=O)$R^{aa}$, —$OCO_2R^{aa}$, —C(=O)N(R^{bb})_2, —OC(=O)N(R^{bb})_2, —$NR^{bb}$C(=O)$R^{aa}$, —$NR^{bb}CO_2R^{aa}$, —$NR^{bb}$C(=O)N(R^{bb})_2, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)N(R^{bb})_2, —OC(=$NR^{bb}$)N(R^{bb})_2, —$NR^{bb}$C(=$NR^{bb}$)N(R^{bb})_2, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —Si($R^{aa}$)_3, —OSi($R^{aa}$)_3, —C(=S)N(R^{bb})_2, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)$OR^{aa}$, —SC(=O)$R^{aa}$, —P(=O)($R^{aa}$)_2, —P(=O)($OR^{cc}$)_2, —OP(=O)($R^{aa}$)_2, —OP(=O)($OR^{cc}$)_2, —P(=O)(N($R^{bb}$)_2)_2, —OP(=O)(N($R^{bb}$)_2)_2, —$NR^{bb}$P(=O)($R^{aa}$)_2, —$NR^{bb}$P(=O)($OR^{cc}$)_2, —$NR^{bb}$P(=O)(N($R^{bb}$)_2)_2, —P($R^{cc}$)_2, —P($OR^{cc}$)_2, —P($R^{cc}$)_3^+X^-, —P($OR^{cc}$)_3^+X^-, —P($R^{cc}$)_4, —P($OR^{cc}$)_4, —OP($R^{cc}$)_2, —OP($R^{cc}$)_3^+X^-, —OP($OR^{cc}$)_2, —OP($OR^{cc}$)_3^+X^-, —OP($R^{cc}$)_4, —OP($OR^{cc}$)_4, —B($R^{aa}$)_2, —B($OR^{cc}$)_2, —$BR^{aa}$($OR^{cc}$), $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group $=O$, $=S$, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

wherein:

each instance of $R^{aa}$ is, independently, selected from $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, $—OH$, $—OR^{aa}$, $—N(R^{cc})_2$, $—CN$, $—C(=O)R^{aa}$, $—C(=O)N(R^{cc})_2$, $—CO_2R^{aa}$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)(R^{aa})_2$, $—P(=O)(OR^{cc})_2$, $—P(=O)(N(R^{cc})_2)_2$, $C_{1-20}$ alkyl, $C_{1-20}$ perhaloalkyl, $C_{1-20}$ alkenyl, $C_{1-20}$ alkynyl, hetero$C_{1-20}$alkyl, hetero$C_{1-20}$alkenyl, hetero$C_{1-20}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, $—CN$, $—NO_2$, $—N_3$, $—SO_2H$, $—SO_3H$, $—OH$, $—OR^{ee}$, $—ON(R^{ff})_2$, $—N(R^{ff})_2$, $—N(R^{ff})_3^+X^-$, $—N(OR^{ee})R^{ff}$, $—SH$, $—SR^{ee}$, $—SSR^{ee}$, $—C(=O)R^{ee}$, $—CO_2H$, $—CO_2R^{ee}$, $—OC(=O)R^{ee}$, $—OCO_2R^{ee}$, $—C(=O)N(R^{ff})_2$, $—OC(=O)N(R^{ff})_2$, $—NR^{ff}C(=O)R^{ee}$, $—NR^{ff}CO_2R^{ee}$, $—NR^{ff}C(=O)N(R^{ff})_2$, $—C(=NR^{ff})OR^{ee}$, $—OC(=NR^{ff})R^{ee}$, $—OC(=NR^{ff})OR^{ee}$, $—C(=NR^{ff})N(R^{ff})_2$, $—OC(=NR^{ff})N(R^{ff})_2$, $—NR^{ff}C(=NR^{ff})N(R^{ff})_2$, $—NR^{ff}SO_2R^{ee}$, $—SO_2N(R^{ff})_2$, $—SO_2R^{ee}$, $—SO_2OR^{ee}$, $—OSO_2R^{ee}$, $—S(=O)R^{ee}$, $—Si(R^{ee})_3$, $—OSi(R^{ee})_3$, $—C(=S)N(R^{ff})_2$, $—C(=O)SR^{ee}$, $—C(=S)SR^{ee}$, $—SC(=S)SR^{ee}$, $—P(=O)(OR^{ee})_2$, $—P(=O)(R^{ee})_2$, $—OP(=O)(R^{ee})_2$, $—OP(=O)(OR^{ee})_2$, $C_{1-10}$ alkyl, $C_{1-10}$ perhaloalkyl, $C_{1-10}$ alkenyl, $C_{1-10}$ alkynyl, hetero$C_{1-10}$alkyl, hetero$C_{1-10}$alkenyl, hetero$C_{1-10}$alkynyl, $C_{3-10}$ carbocyclyl, 3-10 membered heterocyclyl, $C_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents are joined to form $=O$ or $=S$; wherein $X^-$ is a counterion;

each instance of $R^{ee}$ is, independently, selected from $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, 3-10 membered heterocyclyl, $C_{6-10}$ aryl, and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, $—CN$, $—NO_2$, $—N_3$, $—SO_2H$, $—SO_3H$, $—OH$, $—OC_{1-6}$ alkyl, $—ON(C_{1-6}$ alkyl), $—N(C_{1-6}$ alkyl$)_2$, $—N(C_{1-6}$ alkyl$)_3^+X^-$, $—NH(C_{1-6}$ alkyl$)_2^+X^-$, $—NH_2(C_{1-6}$ alkyl$)^+X^-$, $—NH_3^+X^-$, $—N(OC_{1-6}$ alkyl)$(C_{1-6}$ alkyl), $—N(OH)(C_{1-6}$ alkyl), $—NH(OH)$, $—SH$, $—SC_{1-6}$ alkyl, $—SS(C_{1-6}$ alkyl), $—C(=O)(C_{1-6}$ alkyl), $—CO_2H$, $—CO_2(C_{1-6}$ alkyl), $—OC(=O)(C_{1-6}$ alkyl), $—OCO_2(C_{1-6}$ alkyl), $—C(=O)NH_2$, $—C(=O)N(C_{1-6}$ alkyl$)_2$, $—OC(=O)NH(C_{1-6}$ alkyl), $—NHC(=O)(C_{1-6}$ alkyl), $—N(C_{1-6}$ alkyl)C$(=O)(C_{1-6}$ alkyl), $—NHCO_2(C_{1-6}$ alkyl), $—NHC(=O)N(C_{1-6}$ alkyl$)_2$, $—NHC(=O)NH(C_{1-6}$ alkyl), $—NHC(=O)NH_2$, $—C(=NH)O(C_{1-6}$ alkyl), $—OC(=NH)(C_{1-6}$ alkyl), $—OC(=NH)OC_{1-6}$ alkyl, $—C(=NH)N(C_{1-6}$ alkyl$)_2$, $—C(=NH)NH(C_{1-6}$ alkyl), $—C(=NH)NH_2$, $—OC(=NH)N(C_{1-6}$ alkyl$)_2$, $—OC(NH)NH(C_{1-6}$ alkyl), $—OC(NH)NH_2$, $—NHC(NH)N(C_{1-6}$ alkyl$)_2$, $—NHC(=NH)NH_2$, $—NHSO_2(C_{1-6}$ alkyl), $—SO_2N(C_{1-6}$ alkyl$)_2$, $—SO_2NH(C_{1-6}$ alkyl), $—SO_2NH_2$, $—SO_2C_{1-6}$ alkyl, $—SO_2OC_{1-6}$ alkyl, $—OSO_2C_{1-6}$ alkyl, $—SOC_{1-6}$ alkyl, $—Si(C_{1-6}$ alkyl$)_3$, $—OSi(C_{1-6}$ alkyl$)_3$ $—C(=S)N(C_{1-6}$ alkyl$)_2$, C$(=S)NH(C_{1-6}$ alkyl), C$(=S)NH_2$, $—C(=O)S(C_{1-6}$ alkyl), $—C(=S)SC_{1-6}$ alkyl, $—SC(=S)SC_{1-6}$ alkyl, $—P(=O)(OC_{1-6}$ alkyl$)_2$, $—P(=O)(C_{1-6}$ alkyl), $—OP(=O)(C_{1-6}$ alkyl), $—OP(=O)(OC_{1-6}$ alkyl$)_2$, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, or 5-10 membered heteroaryl; or two geminal $R_{gg}$ substituents can be joined to form $=O$ or $=S$; and each $X^-$ is a counterion.

In certain embodiments, each carbon atom substituent is independently halogen, substituted (e.g., substituted with one or more halogen) or unsubstituted $C_{1-6}$ alkyl, $—OR^{aa}$, $—SR^{aa}$, $—N(R^{bb})_2$, $—CN$, $—SCN$, $—NO_2$, $—C(=O)R^{aa}$, $—CO_2R^{aa}$, $—C(=O)N(R^{bb})_2$, $—OC(=O)R^{aa}$, $—OCO_2R^{aa}$, $—OC(=O)N(R^{bb})_2$, $—NR^{bb}C(=O)R^{aa}$, $—NR^{bb}CO_2R^{aa}$, or $—NR^{bb}C(=O)N(R^{bb})_2$. In certain embodiments, each carbon atom substituent is independently halogen, substituted (e.g., substituted with one or more halogen) or unsubstituted $C_{1-10}$ alkyl, —$OR^{aa}$, —$SR^{aa}$, —$N(R^{bb})_2$, —CN, —SCN, —$NO_2$, —$C(=O)R^{aa}$, —$CO_2R^{aa}$, —$C(=O)N(R^{bb})_2$, —$OC(=O)R^{aa}$, —$OC_2R^{aa}$, —$OC(=O)N(R^{bb})_2$, —$NR^{bb}C(=O)R^{aa}$, —$NR^{bb}CO_2R^{aa}$, or —$NR^{bb}C(=O)N(R^{bb})_2$, wherein $R^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts). In certain embodiments, each carbon atom substituent is independently halogen, substituted (e.g., substituted with one or more halogen) or unsubstituted $C_{1-6}$ alkyl, —$OR^{aa}$, —$SR^{aa}$, —$N(R^{bb})_2$, —CN, —SCN, or —$NO_2$. In certain embodiments, each carbon atom substituent is independently halogen, substituted (e.g., substituted with one or more halogen moieties) or unsubstituted $C_{1-10}$ alkyl, —$OR^{aa}$, —$SR^{aa}$, —$N(R^{bb})_2$, —CN, —SCN, or —$NO_2$, wherein $R^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts).

As used herein, the "purity" of a compound refers to the amount of the compound in a composition relative to the total amount of the composition.

In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 80% to 100%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 80%, 81%, 82%, 83%, 84%, 85%, 86%, 87%, 88%, 89%, 90%, 91%, 92%, 93%, 94%, 95%, 96%, 97%, 98%, 99%. In certain embodiments, embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 80%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 81%. In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 82%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 83%. In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 84%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 85%. In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 86%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 87%. In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 88%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 89%. In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 90%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 91%. In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 92%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 93%. In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 94%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 95%. In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 96%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 97%. In certain embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 98%. In some embodiments, the compound of any one of Formulae (I), (II), or (III), or d3-etoricoxib, or a pharmaceutically acceptable salt, hydrate, solvate, polymorph, co-crystal, metabolite, or prodrug thereof, has a purity of at least 99%. In some embodiments, the purity of compounds and compositions disclosed herein (e.g., a compound of any one of Formulae (I), (II), or (III), or d3-etoricoxib) is determined as a percent (%) area basis. In some embodiments, purity is quantified by analytical chromatography. In some embodiments, purity is quantified by HPLC, UHPLC, or UPLC. In certain embodiments, purity is quantified by HPLC.

As used herein, the term "isotopic purity" refers to the percentage of molecules of an isotopically enriched compound (e.g., incorporating one or more heavy atoms, e.g., deuterium) present relative to the total number of molecules of all isotopes of the compound. For example, the isotopic purity of d3-etoricoxib as recited herein refers to the percentage of molecules of d3-etoricoxib present relative to the total number of molecules of etoricoxib isotopes. In some embodiments, a compound disclosed herein has an isotopic purity of at least 50.0%, 60.0%, 70.0%, 75.0%, 80.0%, 85.0%, 90.0%, 95.0%, 97.0%, 98.0%, 99.0%, 99.5%, 99.7%, 99.8%, or 99.9%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 50.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 60.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 70.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 75.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 80.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 85.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 90.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 95.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 97.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 98.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 99.0%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 99.5%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 99.7%. In some embodiments, a compound of any one of Formulae (I), (II), or (III), or d3-etoricoxib, or a pharmaceutically acceptable salt, hydrate, solvate, polymorph, co-crystal, metabolite, or prodrug thereof, has an isotopic purity of at least 99.9%. More specifically, a "compound" may be considered to include more than a single molecule. For example, in some embodiments, the compound is present in an amount measured in micrograms, milligrams, grams, or kilograms, and as such comprises a large number of individual molecules.

As used herein, the terms "isotopic enrichment" or "isotopically enriched" refer to a compound which comprises a greater percentage of one or more heavy atoms (e.g., deuterium) than that which would occur naturally, i.e., as a result of natural abundance. The terms "isotopic enrichment" or "isotopically enriched" may also refer to a particular site (or particular sites) on a molecule which comprise a greater percentage of isotopic atoms (e.g., deuterium) at that site or sites of the molecule than that which would occur naturally, i.e., as a result of natural abundance. In some embodiments, isotopically-enriched etoricoxib disclosed herein comprises a greater percentage of the compound of any one of Formulae (I), (II), or (III), or d3-etoricoxib than would occur as a result of the natural abundance of deuterium (i.e., greater than approximately 0.0115% to 0.0156% relative to the total number of hydrogen isotopes). In some embodiments, the percentage of the compound of any one of Formulae (I), (II), or (III), or d3-etoricoxib is isotopically enriched by at least 0.05%, at least 0.1%, at least 0.5%, at least 1.0, at least 2.0%, at least 3.0%, at least 4.0%, at least 5.0%, at least 10.0%, at least 20.0%, at least 30.0%, at least 40.0%, at least 50.0%, at least 60.0%, at least 70.0%, at least 75.0%, at least 80.0%, at least 85.0%, at least 90.0%, at least 94.0%, at least 95.0%, at least 96.0%, at least 97.0%, at least 98.0%, at least 99.0%, at least 99.5%, at least 99.7%, at least 99.8%, at least 99.9%, or at least 100%. In some embodiments, the percentage of the compound of any one of Formulae (I), (II), or (III), or d3-etoricoxib is isotopically enriched by at least 0.05%. In some embodiments, the percentage of the compound of any one of Formulae (I), (II), or (III), or d3-etoricoxib is isotopically enriched by at least 0.1%. In some embodiments, the percentage of the compound of any one of Formulae (I), (II), or (III), or d3-etoricoxib is isotopically enriched by at least 0.5%. In some embodiments, the percentage of the compound of any one of Formulae (I), (II), or (III), or d3-etoricoxib is isotopically enriched by at least 1.0. In some embodiments, the percentage of the compound of any one of Formulae (I), (II), or (III), or d3-etoricoxib is isotopically enriched by at least 2.0%. In some embodiments, the percentage of the compound of any one of Formulae (I), (II), or (III), or d3-etoricoxib is isotopically enriched by at least 3.0%. In some embodiments, the percentage of the compound of any one of Formulae (I), (II), or (III), or d3-etoricoxib is isotopically enriched by at least 4.0%. In some embodiments, the percentage of the compound of any one of Formulae (I), (II), or (III), or d3-etoricoxib is isotopically enriched by at least 5.0%. In some embodiments, the percentage of the compound of any one of Formulae (I), (II), or (III), or d3-etoricoxib is isotopically enriched by at least 10.0%. In some embodiments, the percentage of the compound of any one of Formulae (I), (II), or (III), or d3-etoricoxib is isotopically enriched by at least 20.0%. In some embodiments, the percentage of the compound of any one of Formulae (I), (II), or (III), or d3-etoricoxib is isotopically enriched by at least 30.0%. In some embodiments, the percentage of the compound of any one of Formulae (I), (II), or (III), or d3-etoricoxib is isotopically enriched by at least 40.0%. In some embodiments, the percentage of the compound of any one of Formulae (I), (II), or (III), or d3-etoricoxib is isotopically enriched by at least 50.0%. In some embodiments, the percentage of the compound of any one of Formulae (I), (II), or (III), or d3-etoricoxib is isotopically enriched by at least 60.0%. In some embodiments, the percentage of the compound of any one of Formulae (I), (II), or (III), or d3-etoricoxib is isotopically enriched by at least 70.0%. In some embodiments, the percentage of the compound of any one of Formulae (I), (II), or (III), or d3-etoricoxib is isotopically enriched by at least 75.0%. In some embodiments, the percentage of the compound of any one of Formulae (I), (II), or (III), or d3-etoricoxib is isotopically enriched by at least 80.0%. In some embodiments, the percentage of the compound of any one of Formulae (I), (II), or (III), or d3-etoricoxib is isotopically enriched by at least 85.0%. In some embodiments, the percentage of the compound of any one of Formulae (I), (II), or (III), or d3-etoricoxib is isotopically enriched by at least 90.0%. In some embodiments, the percentage of the compound of any one of Formulae (I), (II), or (III), or d3-etoricoxib is isotopically enriched by at least 94.0%. In some embodiments, the percentage of the compound of any one of Formulae (I), (II), or (III), or d3-etoricoxib is isotopically enriched by at least 95.0%. In some embodiments, the percentage of the compound of any one of Formulae (I), (II), or (III), or d3-etoricoxib is isotopically enriched by at least 96.0%. In some embodiments, the percentage of the compound of any one of Formulae (I), (II), or (III), or d3-etoricoxib is isotopically enriched by at least 97.0%. In some embodiments, the percentage of the compound of any one of Formulae (I), (II), or (III), or d3-etoricoxib is isotopically enriched by at least 98.0%. In some embodiments, the percentage of the compound of any one of Formulae (I), (II), or (III), or d3-etoricoxib is isotopically enriched by at least 99.0%. In some embodiments, the percentage of the compound of any one of Formulae (I), (II), or (III), or d3-etoricoxib is isotopically enriched by at least 99.5%. In some embodiments, the percentage of the compound of any one of Formulae (I), (II), or (III), or d3-etoricoxib is isotopically enriched by at least 99.7%. In some embodiments, the percentage of the compound of any one of Formulae (I), (II), or (III), or d3-etoricoxib is isotopically enriched by at least 99.8%. In some embodiments, the percentage of the compound of any one of Formulae (I), (II), or (III), or d3-etoricoxib is isotopically enriched by at least 99.9%. In some embodiments, the percentage of the compound of any one of Formulae (I), (II), or (III), or d3-etoricoxib is isotopically enriched by at least 100%. In some embodiments, the compound of Formula (I) is isotopically enriched at one or more of $R^1$, $R^2$, $R^3$, $R^4$, $R^5$, $R^6$, $R^7$, $R_8$, $R_9$, $R^{10}$, $R^{11}$, $R^{12}$, $R^{13}$, $R^{14}$, and $R^{15}$. In certain embodiments, the compound of Formula (I) is isotopically enriched at one or more of $R^{13}$, $R^{14}$, and $R^{15}$. In some embodiments, the compound of Formula (I) is isotopically enriched at each of $R^{13}$, $R^{14}$, and $R^{15}$.

As used herein, the term "the percentage of deuterium" refers to the percentage of hydrogen atoms replaced by deuterium atoms in a compound disclosed herein.

The term "total amount of etoricoxib" refers to the combined total amount of deuterated etoricoxib and non-isotopically enriched etoricoxib in a given composition.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. In some embodiments, the non-human animal is a male or female at any stage of development. In some embodiments, the non-human animal is a transgenic animal or genetically engineered animal.

As used herein, the term "patient" refers to a subject that is a human or animal. In some embodiments, the patient is a healthy patient who is in a generally healthy condition. In some embodiments, the patient is a health patient who is in a generally healthy condition and is eligible to participate as a healthy volunteer in a Phase 1 pharmacokinetic study of a compound or pharmaceutical composition disclosed herein.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound disclosed herein, or a composition thereof, in or on a subject.

The terms "treatment," "treat," and "treating" refer to reversing, alleviating, delaying the onset of, or inhibiting the progress of a disease disclosed herein. In some embodiments, treatment is administered after one or more signs or symptoms of the disease have developed or have been observed. In other embodiments, treatment is administered in the absence of signs or symptoms of the disease. For example, in some embodiments, treatment is administered to a susceptible subject prior to the onset of symptoms (e.g., in light of a history of symptoms and/or in light of exposure to a pathogen). In some embodiments, treatment is continued after symptoms have resolved, for example, to delay or prevent recurrence of a disease or condition.

The terms "condition," "disease," and "disorder" are used interchangeably.

An "effective amount" of a compound disclosed herein refers to an amount sufficient to elicit the desired biological response. In some embodiments, an effective amount of a compound disclosed herein varies depending on such factors as the desired biological endpoint, severity of side effects, disease, or disorder, the identity, pharmacokinetics, and pharmacodynamics of the particular compound, the condition being treated, the mode, route, and desired or required frequency of administration, the species, age and health or general condition of the subject. In certain embodiments, an effective amount is a therapeutically effective amount. In certain embodiments, an effective amount is a prophylactic treatment. In certain embodiments, an effective amount is the amount of a compound disclosed herein in a single dose. In certain embodiments, an effective amount is the combined amounts of a compound disclosed herein in multiple doses. In certain embodiments, the desired dosage is delivered three times a day, two times a day, once a day, every other day, every third day, every week, every two weeks, every three weeks, or every four weeks. In certain embodiments, the desired dosage is delivered using multiple administrations (e.g., two, three, four, five, six, seven, eight, nine, ten, eleven, twelve, thirteen, fourteen, or more administrations).

A "therapeutically effective amount" of a compound disclosed herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for inhibiting COX activity. In certain embodiments, a therapeutically effective amount is an amount sufficient for inhibiting COX-1 activity. In certain embodiments, a therapeutically effective amount is an amount sufficient for inhibiting COX-2 activity. In certain embodiments, a therapeutically effective amount is an amount sufficient for inhibiting COX-3 activity. In certain embodiments, a therapeutically effective amount is an amount sufficient for inhibiting one or more of COX-1 activity, COX-2 activity, and/or COX-3 activity. In certain embodiments, a therapeutically effective amount is an amount sufficient for treating pain, fever, or inflammation. In certain embodiments, a therapeutically effective amount is an amount sufficient for treating pain, fever, or inflammation. In certain embodiments, a therapeutically effective amount is an amount sufficient for inhibiting COX activity and treating pain, fever, or inflammation. In certain embodiments, a therapeutically effective amount is an amount sufficient for inhibiting COX-1 activity and treating pain, fever, or inflammation. In certain embodiments, a therapeutically effective amount is an amount sufficient for inhibiting COX-2 activity and treating pain, fever, or inflammation. In certain embodiments, a therapeutically effective amount is an amount sufficient for inhibiting COX-3 activity and treating pain, fever, or inflammation. In certain embodiments, a therapeutically effective amount is an amount sufficient for inhibiting one or more of COX-1 activity, COX-2 activity, and/or COX-3 activity and treating pain, fever, or inflammation.

A "prophylactically effective amount" of a compound disclosed herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for inhibiting COX activity. In certain embodiments, a prophylactically effective amount is an amount sufficient for inhibiting COX-1 activity. In certain embodiments, a prophylactically effective amount is an amount sufficient for inhibiting COX-2 activity. In certain embodiments, a prophylactically effective amount is an amount sufficient for inhibiting COX-3 activity. In certain embodiments, a prophylactically effective amount is an amount sufficient for inhibiting one or more of COX-1 activity, COX-2 activity, and/or COX-3 activity. In certain embodiments, a prophylactically effective amount is an amount sufficient for preventing pain, fever, or inflammation. In certain embodiments, a prophylactically effective amount is an amount sufficient for inhibiting COX activity and preventing pain, fever, or inflammation. In certain embodiments, a prophylactically effective amount is an amount sufficient for inhibiting COX-1 activity and preventing pain, fever, or inflammation. In certain embodiments, a prophylactically effective amount is an amount sufficient for inhibiting COX-2 activity and preventing pain, fever, or inflammation. In certain embodiments, a prophylactically effective amount is an amount sufficient for inhibiting COX-3 activity and preventing pain, fever, or inflammation. In certain embodiments, a prophylactically effective amount is an amount sufficient for inhibiting one or more of COX-1 activity, COX-2 activity, and/or COX-3 activity and preventing pain, fever, or inflammation.

The phrase "same or equivalent amount," as used herein refers to amounts as measured by mass or by moles, respectively.

As used herein the term "inhibit" or "inhibition" in the context of enzymes, for example, in the context of COX or COX-2, refers to a reduction in the activity of the enzyme. In some embodiments, the term refers to a reduction of the level of enzyme activity, e.g., COX activity or COX-2 activity, to a level that is statistically significantly lower than an initial level, which may, for example, be a baseline level of enzyme activity. In some embodiments, the term refers to a reduction of the level of enzyme activity, e.g., COX activity or COX-2 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

As used herein, the term "mean" refers to a geometric mean unless expressly indicated otherwise. The pharmacokinetic parameters such as "mean $C_{max}$" or "mean AUC" refers to the geometric mean value of a $C_{max}$ or an AUC, unless expressly indicated otherwise (e.g., an arithmetic mean).

The term "inflammation" refers to the biological response of cells, tissues to harmful stimuli, such as pathogens, damaged cells, toxic molecules, or irritants. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

The terms "inflammatory disease" and "inflammatory condition" are used interchangeably herein, and refer to a disease or condition caused by, resulting from, or resulting in inflammation Inflammatory diseases and conditions include those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, partial or complete, temporary or permanent). In some embodiments, the term "inflammatory disease" refers to a dysregulated inflammatory reaction that causes an exaggerated response by macrophages, granulocytes, and/or T-lymphocytes leading to abnormal tissue damage and/or cell death. In some embodiments, an inflammatory disease is either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative joint disease, degenerative arthritis, tendonitis, bursitis, psoriasis, cystic fibrosis, hemophilic arthropathy, arthrosteitis, rheumatoid arthritis, inflammatory arthritis, Sjogren's syndrome, giant cell arteritis, progressive systemic sclerosis (scleroderma), ankylosing spondylitis, myositis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

Additional exemplary inflammatory conditions include, but are not limited to, inflammation associated with acne, anemia (e.g., aplastic anemia, hemolytic autoimmune anemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, Type II diabetes mellitus), a skin condition (e.g., psoriasis, eczema, burns, dermatitis, pruritus (itch)), endometriosis, Guillain-Barre syndrome, infection, ischemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischemic colitis, diversion colitis, Behcet's syndrome, indeterminate colitis) and inflammatory bowel syndrome (IBS)), lupus, multiple sclerosis, morphea, myasthenia gravis, myocardial ischemia, nephrotic syndrome, pemphigus vulgaris, pernicious aneemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, scleroderma, scleroderma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). In some embodiments, the compounds are useful in treating inflammation associated with trauma and non-inflammatory myalgia. In some embodiments, the compounds disclosed herein are useful in treating inflammation associated with cancer.

The term "pain" includes, but is not limited to, neuropathic pain (e.g., peripheral neuropathic pain), central pain, deafferentiation pain, short-term pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (including phantom and transient acute pain), noninflammatory pain, inflammatory pain, pain associated with cancer, wound pain, burn pain, post-operative pain, pain associated with medical procedures, pain resulting from pruritus, painful bladder syndrome, pain associated with premenstrual dysphoric disorder and/or premenstrual syndrome, dysmenorrhea, post-partum pain, pain associated with endometriosis, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, acute gouty arthritis, reactive arthritis, rheumatoid arthritis or Reiter's arthritis), lumbosacral pain, musculoskeletal pain, headache, migraine, muscle ache, lower back pain, neck pain, toothache, dental pain, maxillofacial pain, visceral pain and the like.

In some embodiments, the post-operative pain or pain associated with medical procedures (iatrogenic pain) is associated with anorectal, pelvic floor, or urogynecologic procedures (vaginal/perineal approach) (e.g., colon resection, hemorrhoidectomy, vaginal hysterectomy), breast procedures (e.g., lumpectomy, mastectomy, reconstruction, reduction), dental surgery (e.g., third molar extraction), extremity trauma requiring surgery (e.g., amputation, open reduction, internal fixation), orthopedic surgery or procedures, joint replacement (e.g. total hip arthroplasty (THA), total knee arthroplasty (TKA)), laparoscopic abdominal procedures (e.g., appendectomy, bariatric surgery, cholecystectomy, colectomy, hysterectomy, prostatectomy), open abdominal procedures (e.g., appendectomy, cholecystectomy, colectomy, hysterectomy), laparoscopic or open abdominal wall procedures (e.g., femoral hernia, incisional hernia, inguinal hernia), obstetric procedures (e.g., cesarean delivery, vaginal delivery), oropharyngeal procedures (e.g., tonsillectomy), spine procedures (e.g., fusion in both adults and children, laminectomy), procedures related to sport-related injuries (e.g., ACL repair and reconstruction, joint arthroscopy, rotator cuff repair), or thoracic procedures (e.g., thoracoscopy, repair of pectus excavatum in children (Nuss procedure)).

As disclosed herein, pain can comprise mixtures of various types of pain provided above and herein (e.g., nociceptive pain, inflammatory pain, neuropathic pain, etc.). In some embodiments, a particular pain can dominate. In other embodiments, the pain comprises two or more types of pains without one dominating. A skilled clinician can determine the dosage to achieve a therapeutically effective amount for a particular subject based on the pain.

In certain embodiments, the pain is inflammatory pain. In certain embodiments, the pain (e.g., inflammatory pain) is associated with inflammation or an inflammatory condition.

In certain embodiments, the pain is non-inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory input to the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists, such as a limb that has been amputated), pain felt by psychiatric subjects (e.g., pain where no physical cause exists), and wandering pain (e.g., wherein the pain repeatedly changes location in the body).

In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

In some embodiments, pain is measured through any clinically-validated pain assessment measurement. In some embodiments, pain is measured through the Pain Intensity Numerical Rating Scale. In some embodiments, pain is measured by use of a visual analogue scale ("VAS," such as a 10 cm scale with 0 representing no pain and 10 representing maximal pain).

The term "fever" refers to an elevated body temperature that is approximately 37.7° C. (99.9° F.) or greater for a human subject. In some embodiments, the fever is an infectious fever caused by or associated with an infectious cause, disorder or disease or a non-infectious fever not caused by or associated with an infectious cause, disorder or disease. Common causes of infectious fevers include, but are not limited to, upper and lower respiratory tract infections, gastrointestinal infections, urinary tract infection, and skin infections. Non-limiting pathogens associated with infectious diseases include viruses, bacteria, fungi, yeast, protozoans, nematodes, and other parasites. In some embodiments, a non-infectious fever is associated with an inflammatory disorder or disease, or cancer, or is caused by a drug, an immunization, heat exhaustion, sunburn, and the like. In some embodiments, the fever is associated with a viral infection (e.g., influenza, the common cold, COVID-19), dengue fever, or rheumatic fever.

Unless otherwise required by context, singular terms shall include pluralities, and plural terms shall include the singular. The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

When a range of values ("range") is listed, it encompasses each value and sub-range within the range. A range is inclusive of the values at the two ends of the range unless otherwise provided. It will be understood that when a range is recited in the application, the ends of the range are specifically disclosed as if specifically recited. For example, a range of about 19% to about 99% specifically include a disclosure separately of 19% and separately of 99%.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2%, or 1% of a given value or range of values.

DETAILED DESCRIPTION OF CERTAIN EMBODIMENTS

Disclosed herein are deuterated forms of etoricoxib, or a pharmaceutically acceptable salt, hydrate, solvate, polymorph, co-crystal, metabolite, or prodrug thereof, compositions and kits comprising the same, and methods of using the same. United States Patent Application Publication No. US 2009/0076087 A1 to Czarnik/Protia, LLC generically and prophetically discloses "deuterium-enriched etoricoxib." However, the inventors unexpectedly discovered that certain deuterated forms of etoricoxib display improved properties, including improved pharmacokinetic properties. For example, certain deuterated forms of etoricoxib disclosed herein possess improved maximum serum concentration ($C_{max}$), total systemic exposure (AUC), time of maximal plasma concentration ($T_{max}$), and/or half-life ($t_{1/2}$) that are distinct from those demonstrated by previously known etoricoxib compositions. Without wishing to be bound by theory, the inventors posit that these deuterated forms of etoricoxib allow for advantages such as reduced dosages, reduced dosage intervals, improved therapeutic windows, modified release, reduced formation of one or more metabolites of etoricoxib, and/or reduced side effects, as compared to previously known etoricoxib compositions.

Compounds

In one aspect, the present disclosure provides a compound of Formula (I):

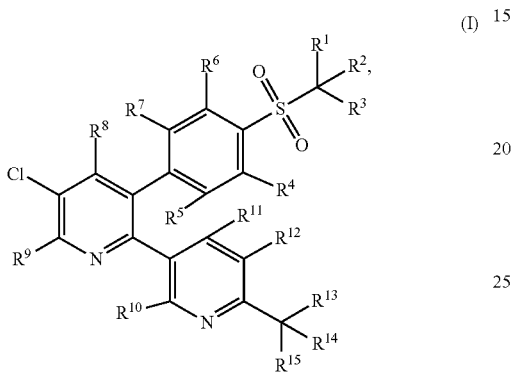

or a pharmaceutically acceptable salt, hydrate, solvate, polymorph, co-crystal, metabolite, or prodrug thereof; wherein:
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium; provided that:
(1) at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium; and
(2) the compound is not of the formula:

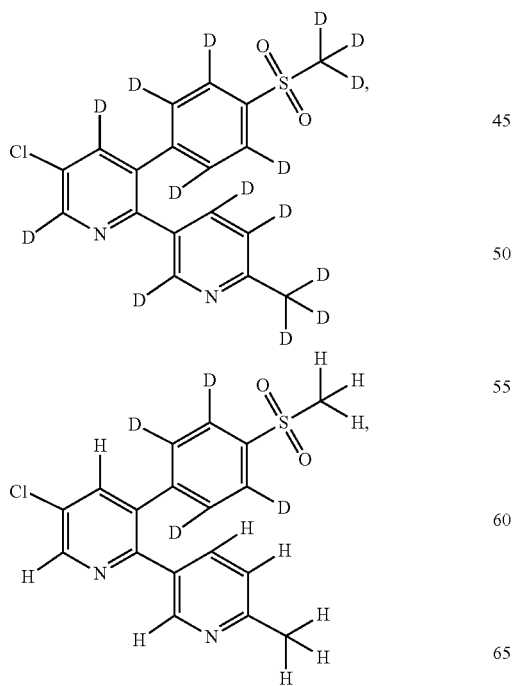

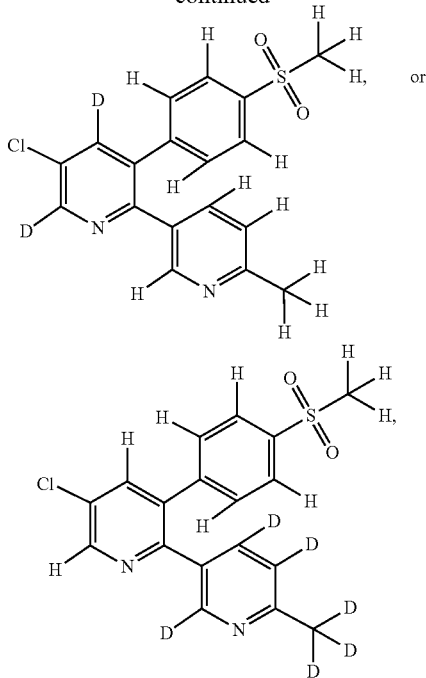

or a pharmaceutically acceptable salt, hydrate, solvate, polymorph, co-crystal, metabolite, or prodrug thereof.

In another aspect, the present disclosure provides a compound of Formula (I):

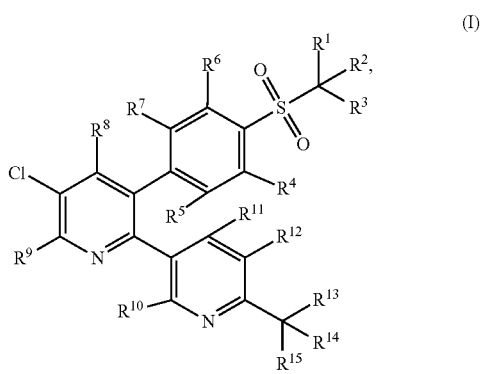

or a pharmaceutically acceptable salt, hydrate, solvate, polymorph, co-crystal, metabolite, or prodrug thereof; wherein:
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium; provided that:
(1) at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium;
(2) at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is hydrogen;
(3) when each of $R^1$, $R^2$, $R^3$, $R^8$, $R^9$, $R^{10}$, $R^{11}$, $R^{12}$, $R^{13}$, $R^{14}$, and $R^{15}$ is hydrogen, at least one of $R^4$, $R^5$, $R^6$, and $R^7$ is hydrogen;
(4) when each of $R^1$, $R^2$, $R^3$, $R^4$, $R^5$, $R^6$, $R^7$, $R^{10}$, $R^{11}$, $R^{12}$, $R^{13}$, $R^{14}$, and $R^{15}$ is hydrogen, at least one of $R^8$ and $R^9$ is hydrogen; and
(5) when each of $R^1$, $R^2$, $R^3$, $R^4$, $R^5$, $R^6$, $R^7$, $R^8$, and $R^9$ is hydrogen, at least one of $R^{10}$, $R^{11}$, $R^{12}$, $R^{13}$, $R^{14}$, and $R^{15}$ is hydrogen.

In some embodiments, the compound of Formula (I) is of Formula (I-A):

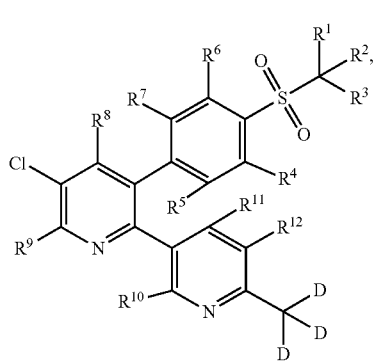

(I-A)

or a pharmaceutically acceptable salt, hydrate, solvate, polymorph, co-crystal, metabolite, or prodrug thereof.

In some embodiments, at least one of $R^4$, $R^5$, $R^6$, and $R^7$ is hydrogen. In some embodiments, at least one of $R^8$ and $R^9$ is hydrogen. In some embodiments, when each of $R^{13}$, $R^{14}$, and $R^{15}$ is deuterium, at least one of $R^{10}$, $R^{11}$, and $R^{12}$ is hydrogen. In some embodiments, when each of $R^{10}$, $R^{11}$, and $R^{12}$ is deuterium, at least one of $R^{13}$, $R^{14}$, and $R^{15}$ is hydrogen. In some embodiments, at least one of $R^4$, $R^5$, $R^6$, and $R^7$ is hydrogen, at least one of $R^8$ and $R^9$ is hydrogen, when each of $R^{13}$, $R^{14}$, and $R^{15}$ is deuterium, at least one of $R^{10}$, $R^{11}$, and $R^{12}$ is hydrogen, and when each of $R^{10}$, $R^{11}$, and $R^{12}$ is deuterium, at least one of $R^{13}$, $R^{14}$, and $R^{15}$ is hydrogen.

In some embodiments, at least one of $R^1$, $R^2$, and $R^3$ is deuterium. In some embodiments, at least two of $R^1$, $R^2$, and $R^3$ are deuterium. In some embodiments, each of $R^1$, $R^2$, and $R^3$ is deuterium. In some embodiments, $R^1$ is deuterium. In some embodiments $R^2$ is deuterium. In some embodiments $R^3$ is deuterium. In some embodiments $R^1$ and $R^2$ are deuterium. In some embodiments, $R^1$ and $R^3$ are deuterium. In some embodiments, $R^2$ and $R^3$ are deuterium. In some embodiments, each of $R^1$, $R^2$, and $R^3$ is hydrogen.

In some embodiments, at least one of $R^4$, $R^5$, $R^6$, and $R^7$ is deuterium. In some embodiments, at least two of $R^4$, $R^5$, $R^6$ and $R^7$ are deuterium. In some embodiments, three of $R^4$, $R^5$, $R^6$, and $R^7$ are deuterium. In some embodiments, $R^4$ is deuterium. In some embodiments, $R^5$ is deuterium. In some embodiments, $R^6$ is deuterium. In some embodiments, $R^7$ is deuterium. In some embodiments, $R^4$ and $R^5$ are deuterium. In some embodiments, $R^4$ and $R^6$ are deuterium. In some embodiments, $R^4$ and $R^7$ are deuterium. In some embodiments, $R^5$ and $R^6$ are deuterium. In some embodiments, $R^5$ and $R^7$ are deuterium. In some embodiments, $R^6$ and $R^7$ are deuterium. In some embodiments, $R^4$, $R^5$, and $R^6$ are deuterium. In some embodiments, $R^4$, $R^5$, and $R^7$ are deuterium. In some embodiments, $R^4$, $R^6$, and $R^7$ are deuterium. In some embodiments, $R^5$, $R^6$, and $R^7$ are deuterium. In some embodiments, each of $R^4$, $R^5$, $R^6$, and $R^7$ is hydrogen.

In some embodiments, one of $R^8$ and $R^9$ is deuterium. In some embodiments, $R^8$ is deuterium. In some embodiments, $R^9$ is deuterium. In some embodiments, each of $R^8$ and $R^9$ is hydrogen.

In some embodiments, at least one of $R^{10}$, $R^{11}$, and $R^{12}$ is deuterium. In some embodiments, at least two of $R^{10}$, $R^{11}$, and $R^{12}$ are deuterium. In some embodiments, each of $R^{10}$, $R^{11}$, and $R^{12}$ is deuterium. In some embodiments, $R^{10}$ is deuterium. In some embodiments, $R^{11}$ is deuterium. In some embodiments, $R^{12}$ is deuterium. In some embodiments, $R^{10}$ and $R^{11}$ are deuterium. In some embodiments, $R^{10}$ and $R^{12}$ are deuterium. In some embodiments, $R^{11}$ and $R^{12}$ are deuterium. In some embodiments, each of $R^{10}$, $R^{11}$, and $R^{12}$ is hydrogen.

In some embodiments, at least one of $R^{13}$, $R^{14}$, and $R^{15}$ is deuterium. In some embodiments, at least two of $R^{13}$, $R^{14}$, and $R^{15}$ are deuterium. In some embodiments, each of $R^{13}$, $R^{14}$, and $R^{15}$ is deuterium. In some embodiments, $R^{13}$ is deuterium. In some embodiments, $R^{14}$ is deuterium. In some embodiments, $R^{15}$ is deuterium. In some embodiments, $R^{13}$ and $R^{14}$ are deuterium. In some embodiments, $R^{13}$ and $R^{15}$ are deuterium. In some embodiments, $R^{14}$ and $R^{15}$ are deuterium. In some embodiments, each of $R^{13}$, $R^{14}$, and $R^{15}$ is hydrogen.

In some embodiments, each of $R^{13}$, $R^{14}$, and $R^{15}$ is deuterium, and $R^{10}$ is hydrogen. In some embodiments, each of $R^{13}$, $R^{14}$, and $R^{15}$ is deuterium, and $R^{11}$ is hydrogen. In some embodiments, each of $R^{13}$, $R^{14}$, and $R^{15}$ is deuterium, and $R^{12}$ is hydrogen. In some embodiments, each of $R^{13}$, $R^{14}$, and $R^{15}$ is deuterium, and $R^{10}$ and $R^{11}$ are hydrogen. In some embodiments, each of $R^{13}$, $R^{14}$, and $R^{15}$ is deuterium, and $R^{10}$ and $R^{12}$ are hydrogen. In some embodiments, each of $R^{13}$, $R^{14}$, and $R^{15}$ is deuterium, and $R^{11}$ and $R^{12}$ are hydrogen. In some embodiments, each of $R^{13}$, $R^{14}$, and $R^{15}$ is deuterium, and $R^{10}$, $R^{11}$, and $R^{12}$ are hydrogen.

In some embodiments, each of $R^{10}$, $R^{11}$, and $R^{12}$ is deuterium, and $R^{13}$ is hydrogen. In some embodiments, each of $R^{10}$, $R^{11}$, and $R^{12}$ is deuterium, and $R^{14}$ is hydrogen. In some embodiments, each of $R^{10}$, $R^{11}$, and $R^{12}$ is deuterium, and $R^{15}$ is hydrogen. In some embodiments, each of $R^{10}$, $R^{11}$, and $R^{12}$ is deuterium, and $R^{13}$ and $R^{14}$ are hydrogen. In some embodiments, each of $R^{10}$, $R^{11}$, and $R^{12}$ is deuterium, and $R^{13}$ and $R^{15}$ are hydrogen. In some embodiments, each of $R^{10}$, $R^{11}$, and $R^{12}$ is deuterium, and $R^{14}$ and $R^{15}$ are hydrogen. In some embodiments, each of $R^{10}$, $R^{11}$, and $R^{12}$ is deuterium, and $R^{13}$, $R^{14}$, and $R^{15}$ are hydrogen.

In some embodiments, each of $R^1$, $R^2$, $R^3$, $R^{13}$, $R^{14}$, and $R^{15}$ is deuterium. In some embodiments, each of $R^1$, $R^2$, $R^3$, $R^4$, $R^5$, $R^6$, $R^7$, $R^{13}$, $R^{14}$, and $R^{15}$ is deuterium. In some embodiments, each of $R^4$, $R^5$, $R^6$, $R^7$, $R^{13}$, $R^{14}$, and $R^{15}$ is deuterium. In some embodiments, each of $R^8$, $R^9$, $R^{13}$, $R^{14}$, and $R^{15}$ is deuterium. In some embodiments, each of $R^1$, $R^2$, $R^3$, $R^8$, $R^9$, $R^{13}$, $R^{14}$, and $R^{15}$ is deuterium.

In some embodiments, the compound is not of the formula:

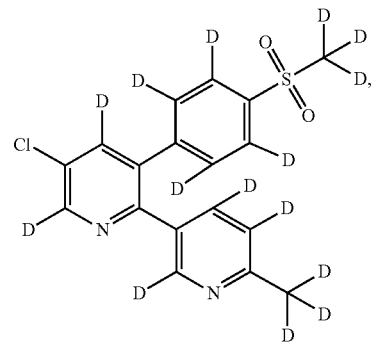

or a pharmaceutically acceptable salt, hydrate, solvate, polymorph, co-crystal, metabolite, or prodrug thereof.

In some embodiments, the compound is not of the formula:

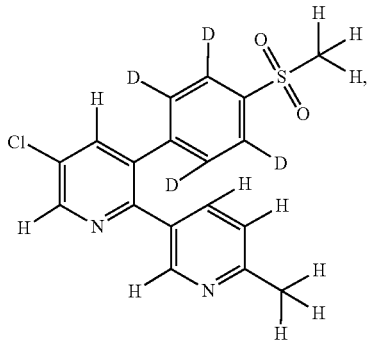

or a pharmaceutically acceptable salt, hydrate, solvate, polymorph, co-crystal, metabolite, or prodrug thereof.

In some embodiments, the compound is not of the formula:

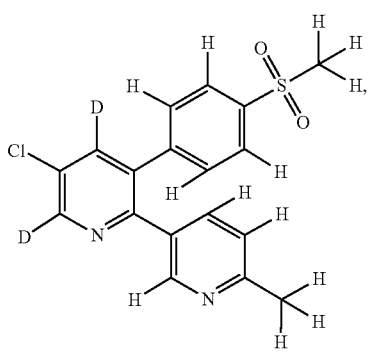

or a pharmaceutically acceptable salt, hydrate, solvate, polymorph, co-crystal, metabolite, or prodrug thereof.

In some embodiments, the compound is not of the formula:

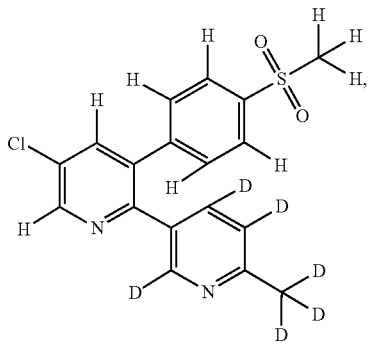

or a pharmaceutically acceptable salt, hydrate, solvate, polymorph, co-crystal, metabolite, or prodrug thereof.

In some embodiments, the compound is not of the formula:

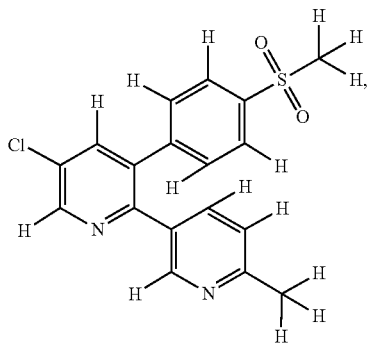

or a pharmaceutically acceptable salt, hydrate, solvate, polymorph, co-crystal, metabolite, or prodrug thereof.

In another aspect, the present disclosure provides a compound of Formula (I):

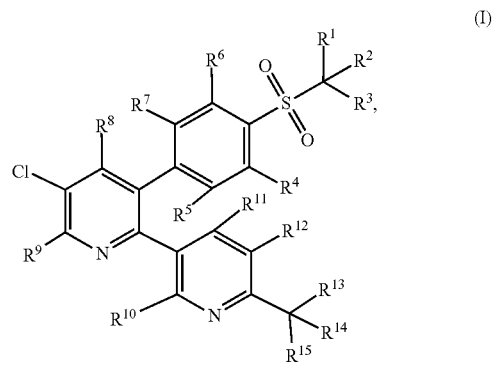

or a pharmaceutically acceptable salt, hydrate, solvate, polymorph, or co-crystal thereof.

In another aspect, the present disclosure provides a compound of Formula (I):

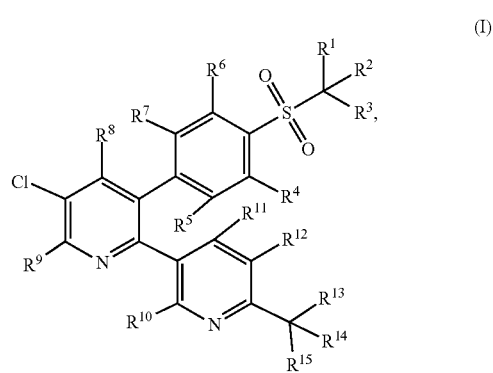

or a pharmaceutically acceptable salt thereof.

In another aspect, the present disclosure provides a compound of the formula:

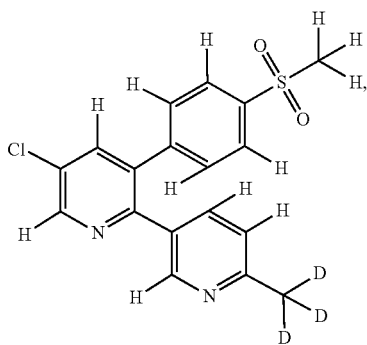

or a pharmaceutically acceptable salt, hydrate, solvate, polymorph, co-crystal, metabolite, or prodrug thereof.

In another aspect, the present disclosure provides a compound of the formula:

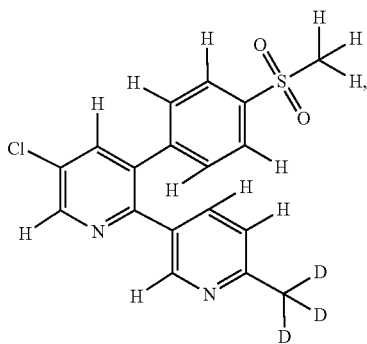

or a pharmaceutically acceptable salt, hydrate, solvate, polymorph, or co-crystal thereof.

In another aspect, the present disclosure provides a compound of the formula:

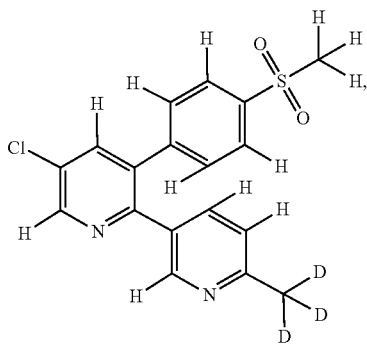

or a pharmaceutically acceptable salt thereof.

In some embodiments, the salt of a compound of any one of Formulae (I), (II), or (III), or d3-etoricoxib is an oxalate, succinate, fumarate, besylate, hydrobromide, hydrochloride, glutamate, sulfamate, benzoate, cinnamate, salicylate, or tosylate salt. In some embodiments, the salt is an oxalate salt. In some embodiments, the salt is a succinate salt. In some embodiments, the salt is a fumarate salt. In some embodiments, the salt is a besylate salt. In some embodiments, the salt is a hydrobromide salt. In some embodiments, the salt is a hydrochloride salt. In some embodiments, the salt is a glutamate salt. In some embodiments, the salt is a sulfamate salt. In some embodiments, the salt is a benzoate salt. In some embodiments, the salt is a cinnamate salt. In some embodiments, the salt is a salicylate salt. In some embodiments, the salt is a tosylate salt.

In some embodiments, the metabolite of a compound of any one of Formulae (I), (II), or (III), or d3-etoricoxib, or a pharmaceutically acceptable salt, hydrate, solvate, polymorph, co-crystal, metabolite, or prodrug thereof, comprises a hydroxyl group in place of a hydrogen or deuterium. In some embodiments, the metabolite substitutes a hydroxyl group for hydrogen or deuterium at $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, or $R^{15}$. In some embodiments, the metabolite substitutes a hydroxyl group for hydrogen or deuterium at one or more of $R^{13}$, $R^{14}$, and $R^{15}$. In some embodiments, the metabolite substitutes a hydroxyl group for one hydrogen or deuterium at $R^{13}$, $R^{14}$, and $R^{15}$. In some embodiments, the metabolite substitutes a hydroxyl group for hydrogen or deuterium at two of $R^{13}$, $R^{14}$, and $R^{15}$. In some embodiments, the metabolite substitutes a hydroxyl group for hydrogen or deuterium at each of $R^{13}$, $R^{14}$, and $R^{15}$.

In some embodiments, the metabolite of a compound of Formula (I) has the structure:

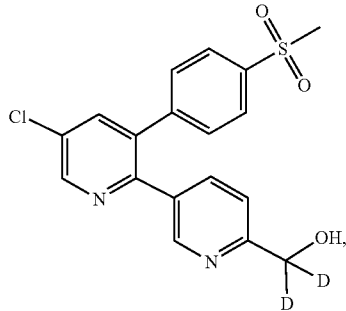 [SMILES: [2H]C([2H])(O)c1ccc(-c2ncc(Cl)cc2-c2ccc(S(C)(=O)=O)cc2)cn1]

or a pharmaceutically acceptable salt, hydrate, solvate, polymorph, or co-crystal thereof.

In some embodiments, the compound of any one of Formulae (I), (II), or (III), or d3-etoricoxib, or a pharmaceutically acceptable salt, hydrate, solvate, polymorph, co-crystal, metabolite, or prodrug thereof, achieves a higher geometric mean $C_{max}$ plasma concentration following administration of a single dose of the compound, or a pharmaceutically acceptable salt, hydrate, solvate, polymorph, co-crystal, metabolite, or prodrug thereof, or the pharmaceutical composition, to a population of patients compared to a control composition comprising non-isotopically enriched etoricoxib, or a pharmaceutically acceptable salt, hydrate, solvate, polymorph, co-crystal, metabolite, or prodrug thereof, or a pharmaceutical composition comprising etoricoxib, or a pharmaceutically acceptable salt, hydrate, solvate, polymorph, co-crystal, metabolite, or prodrug thereof, and a pharmaceutically acceptable excipient. In some embodiments, the patients are healthy patients.

In some embodiments, the geometric mean $C_{max}$ plasma concentration is at least 5%, 10%, 15%, 20%, 25%, 30%, 35%, 40%, 45%, or 50% higher. In some embodiments, the geometric mean $C_{max}$ plasma concentration is at least 5% higher. In some embodiments, the geometric mean $C_{max}$ plasma concentration is at least 10% higher. In some embodiments, the geometric mean $C_{max}$ plasma concentration is at least 15% higher. In some embodiments, the geometric mean $C_{max}$ plasma concentration is at least 20% higher. In some embodiments, the geometric mean $C_{max}$ plasma concentration is at least 25% higher. In some embodiments, the geometric mean $C_{max}$ plasma concentration is at least 30% higher. In some embodiments, the geometric mean $C_{max}$ plasma concentration is at least 35% higher. In some embodiments, the geometric mean $C_{max}$ plasma concentration is at least 40% higher. In some embodiments, the geometric mean $C_{max}$ plasma concentration is at least 45% higher. In some embodiments, the geometric mean $C_{max}$ plasma concentration is at least 50% higher.

In some embodiments, the compound of any one of Formulae (I), (II), or (III), or d3-etoricoxib, or a pharmaceutically acceptable salt, hydrate, solvate, polymorph, co-crystal, metabolite, or prodrug thereof, achieves a higher geometric mean plasma AUC following administration of a single dose of the compound, or a pharmaceutically acceptable salt, hydrate, solvate, polymorph, co-crystal, metabolite, or prodrug thereof, or the pharmaceutical composition, to a population of patients compared to a control composition comprising non-isotopically enriched etoricoxib, or a pharmaceutically acceptable salt, hydrate, solvate, polymorph, co-crystal, metabolite, or prodrug thereof, or a pharmaceutical composition comprising etoricoxib, or a pharmaceutically acceptable salt, hydrate, solvate, polymorph, co-crystal, metabolite, or prodrug thereof, and a pharmaceutically acceptable excipient. In some embodiments, the patients are healthy patients.

In some embodiments, the geometric mean plasma AUC is at least 5%, 10%, 15%, 20%, 25%, 30%, 35%, 40%, 45%, or 50% higher. In some embodiments, the geometric mean plasma AUC is at least 5% higher. In some embodiments, the geometric mean plasma AUC is at least 10% higher. In some embodiments, the geometric mean plasma AUC is at least 15% higher. In some embodiments, the geometric mean plasma AUC is at least 20% higher. In some embodiments, the geometric mean plasma AUC is at least 25% higher. In some embodiments, the geometric mean plasma AUC is at least 30% higher. In some embodiments, the geometric mean plasma AUC is at least 35% higher. In some embodiments, the geometric mean plasma AUC is at least 40% higher. In some embodiments, the geometric mean plasma AUC is at least 45% higher. In some embodiments, the geometric mean plasma AUC is at least 50% higher.

In some embodiments, the geometric mean plasma AUC is the geometric mean plasma $AUC_{0-24}$. In some embodiments, the geometric mean plasma AUC is the geometric mean plasma $AUC_{0-\infty}$.

In another aspect, the present disclosure provides a compound of Formula (II):

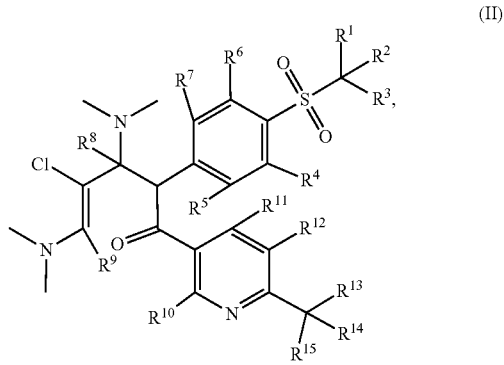

(II)

or a salt, hydrate, solvate, polymorph, or co-crystal thereof; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of Formula (II):

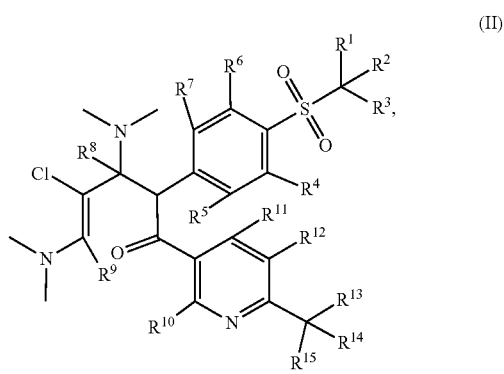

(II)

or a salt thereof; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of the formula:

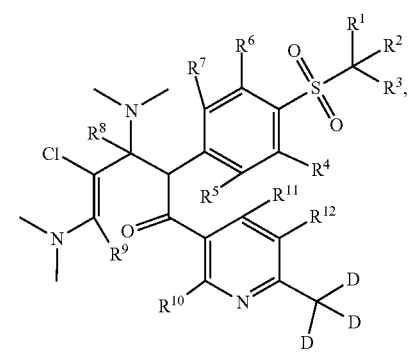

or a salt, hydrate, solvate, polymorph, or co-crystal thereof.

In another aspect, the present disclosure provides a compound of the formula:

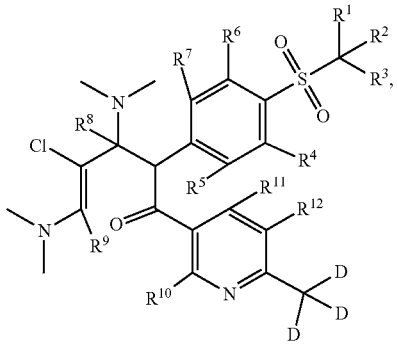

or a salt thereof.

In some embodiments, at least one of $R^4$, $R^5$, $R^6$, and $R^7$ is hydrogen. In some embodiments, at least one of $R^8$ and $R^9$ is hydrogen. In some embodiments, when each of $R^{13}$, $R^{14}$, and $R^{15}$ is deuterium, at least one of $R^{10}$, $R^{11}$, and $R^{12}$ is hydrogen. In some embodiments, when each of $R^{10}$, $R^{11}$, and $R^{12}$ is deuterium, at least one of $R^{13}$, $R^{14}$, and $R^{15}$ is hydrogen. In some embodiments, at least one of $R^4$, $R^5$, $R^6$, and $R^7$ is hydrogen, at least one of $R^8$ and $R^9$ is hydrogen, when each of $R^{13}$, $R^{14}$, and $R^{15}$ is deuterium, at least one of $R^{10}$, $R^{11}$, and $R^{12}$ is hydrogen, and when each of $R^{10}$, $R^{11}$, and $R^{12}$ is deuterium, at least one of $R^{13}$, $R^{14}$, and $R^{15}$ is hydrogen.

In some embodiments, at least one of $R^1$, $R^2$, and $R^3$ is deuterium. In some embodiments, at least two of $R^1$, $R^2$, and $R^3$ are deuterium. In some embodiments, each of $R^1$, $R^2$, and $R^3$ is deuterium. In some embodiments, $R^1$ is deuterium. In some embodiments $R^2$ is deuterium. In some embodiments $R^3$ is deuterium. In some embodiments $R^1$ and $R^2$ are deuterium. In some embodiments, $R^1$ and $R^3$ are deuterium. In some embodiments, $R^2$ and $R^3$ are deuterium. In some embodiments, each of $R^1$, $R^2$, and $R^3$ is hydrogen.

In some embodiments, at least one of $R^4$, $R^5$, $R^6$, and $R^7$ is deuterium. In some embodiments, at least two of $R^4$, $R^5$, $R^6$ and $R^7$ are deuterium. In some embodiments, three of $R^4$, $R^5$, $R^6$, and $R^7$ are deuterium. In some embodiments, $R^4$ is deuterium. In some embodiments, $R^5$ is deuterium. In some embodiments, $R^6$ is deuterium. In some embodiments, $R^7$ is deuterium. In some embodiments, $R^4$ and $R^5$ are deuterium. In some embodiments, $R^4$ and $R^6$ are deuterium. In some embodiments, $R^4$ and $R^7$ are deuterium. In some embodiments, $R^5$ and $R^6$ are deuterium. In some embodiments, $R^5$ and $R^7$ are deuterium. In some embodiments, $R^6$ and $R^7$ are deuterium. In some embodiments, $R^4$, $R^5$, and $R^6$ are deuterium. In some embodiments, $R^4$, $R^5$, and $R^7$ are deuterium. In some embodiments, $R^4$, $R^6$, and $R^7$ are deuterium. In some embodiments, $R^5$, $R^6$, and $R^7$ are deuterium. In some embodiments, each of $R^4$, $R^5$, $R^6$, and $R^7$ is hydrogen.

In some embodiments, one of $R^8$ and $R^9$ is deuterium. In some embodiments, $R^8$ is deuterium. In some embodiments, $R^9$ is deuterium. In some embodiments, each of $R^8$ and $R^9$ is hydrogen.

In some embodiments, at least one of $R^{10}$, $R^{11}$, and $R^{12}$ is deuterium. In some embodiments, at least two of $R^{10}$, $R^{11}$, and $R^{12}$ are deuterium. In some embodiments, each of $R^{10}$, $R^{11}$, and $R^{12}$ is deuterium. In some embodiments, $R^{10}$ is deuterium. In some embodiments, $R^{11}$ is deuterium. In some embodiments, $R^{12}$ is deuterium. In some embodiments, $R^{10}$ and $R^{11}$ are deuterium. In some embodiments, $R^{10}$ and $R^{12}$ are deuterium. In some embodiments, $R^{11}$ and $R^{12}$ are deuterium. In some embodiments, each of $R^{10}$, $R^{11}$, and $R^{12}$ is hydrogen.

In some embodiments, at least one of $R^{13}$, $R^{14}$, and $R^{15}$ is deuterium. In some embodiments, at least two of $R^{13}$, $R^{14}$, and $R^{15}$ are deuterium. In some embodiments, each of $R^{13}$, $R^{14}$, and $R^{15}$ is deuterium. In some embodiments, $R^{13}$ is deuterium. In some embodiments, $R^{14}$ is deuterium. In some embodiments, $R^{15}$ is deuterium. In some embodiments, $R^{13}$ and $R^{14}$ are deuterium. In some embodiments, $R^{13}$ and $R^{15}$ are deuterium. In some embodiments, $R^{14}$ and $R^{15}$ are deuterium. In some embodiments, each of $R^{13}$, $R^{14}$, and $R^{15}$ is hydrogen.

In some embodiments, each of $R^{13}$, $R^{14}$, and $R^{15}$ is deuterium, and $R^{10}$ is hydrogen. In some embodiments, each of $R^{13}$, $R^{14}$, and $R^{15}$ is deuterium, and $R^{11}$ is hydrogen. In some embodiments, each of $R^{13}$, $R^{14}$, and $R^{15}$ is deuterium, and $R^{12}$ is hydrogen. In some embodiments, each of $R^{13}$, $R^{14}$, and $R^{15}$ is deuterium, and $R^{10}$ and $R^{11}$ are hydrogen. In some embodiments, each of $R^{13}$, $R^{14}$, and $R^{15}$ is deuterium, and $R^{10}$ and $R^{12}$ are hydrogen. In some embodiments, each of $R^{13}$, $R^{14}$, and $R^{15}$ is deuterium, and $R^{11}$ and $R^{12}$ are hydrogen. In some embodiments, each of $R^{13}$, $R^{14}$, and $R^{15}$ is deuterium, and $R^{10}$, $R^{11}$, and $R^{12}$ are hydrogen.

In some embodiments, each of $R^{10}$, $R^{11}$, and $R^{12}$ is deuterium, and $R^{13}$ is hydrogen. In some embodiments, each of $R^{10}$, $R^{11}$, and $R^{12}$ is deuterium, and $R^{14}$ is hydrogen. In some embodiments, each of $R^{10}$, $R^{11}$, and $R^{12}$ is deuterium, and $R^{15}$ is hydrogen. In some embodiments, each of $R^{10}$, $R^{11}$, and $R^{12}$ is deuterium, and $R^{13}$ and $R^{14}$ are hydrogen. In some embodiments, each of $R^{10}$, $R^{11}$, and $R^{12}$ is deuterium, and $R^{13}$ and $R^{15}$ are hydrogen. In some embodiments, each of $R^{10}$, $R^{11}$, and $R^{12}$ is deuterium, and $R^{14}$ and $R^{15}$ are hydrogen. In some embodiments, each of $R^{10}$, $R^{11}$, and $R^{12}$ is deuterium, and $R^{13}$, $R^{14}$, and $R^{15}$ are hydrogen.

In some embodiments, each of $R^1$, $R^2$, $R^3$, $R^{13}$, $R^{14}$, and $R^{15}$ is deuterium. In some embodiments, each of $R^1$, $R^2$, $R^3$, $R^4$, $R^5$, $R^6$, $R^7$, $R^{13}$, $R^{14}$, and $R^{15}$ is deuterium. In some embodiments, each of $R^4$, $R^5$, $R^6$, $R^7$, $R^{13}$, $R^{14}$, and $R^{15}$ is deuterium. In some embodiments, each of $R^8$, $R^9$, $R^{13}$, $R^{14}$, and $R^{15}$ is deuterium. In some embodiments, each of $R^1$, $R^2$, $R^3$, $R^8$, $R^9$, $R^{13}$, $R^{14}$, and $R^{15}$ is deuterium.

In another aspect, the present disclosure provides a compound of the formula:

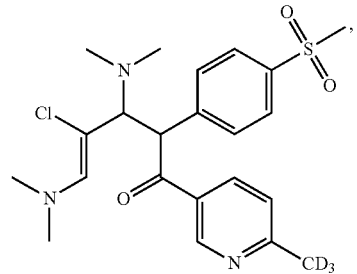

or a pharmaceutically acceptable salt, hydrate, solvate, polymorph, or co-crystal thereof.

In another aspect, the present disclosure provides a compound of the formula:

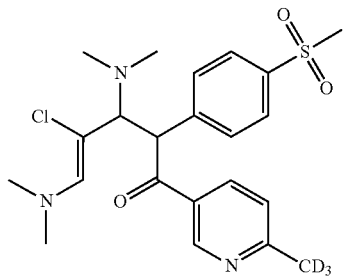

or a pharmaceutically acceptable salt thereof.

In another aspect, the present disclosure provides a compound of Formula (III):

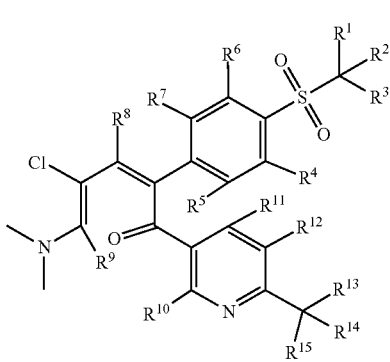

or a salt, hydrate, solvate, polymorph, or co-crystal thereof; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a compound of Formula (III):

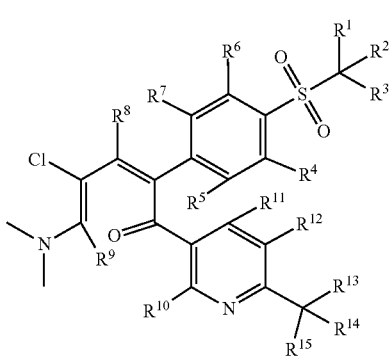

or a salt thereof; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In some embodiments, at least one of $R^4$, $R^5$, $R^6$, and $R^7$ is hydrogen. In some embodiments, at least one of $R^8$ and $R^9$ is hydrogen. In some embodiments, when each of $R^{13}$, $R^{14}$, and $R^{15}$ is deuterium, at least one of $R^{10}$, $R^{11}$, and $R^{12}$ is hydrogen. In some embodiments, when each of $R^{10}$, $R^{11}$, and $R^{12}$ is deuterium, at least one of $R^{13}$, $R^{14}$, and $R^{15}$ is hydrogen. In some embodiments, at least one of $R^4$, $R^5$, $R^6$, and $R^7$ is hydrogen, at least one of $R^8$ and $R^9$ is hydrogen, when each of $R^{13}$, $R^{14}$, and $R^{15}$ is deuterium, at least one of $R^{10}$, $R^{11}$, and $R^{12}$ is hydrogen, and when each of $R^{10}$, $R^{11}$, and $R^{12}$ is deuterium, at least one of $R^{13}$, $R^{14}$, and $R^{15}$ is hydrogen.

In some embodiments, at least one of $R^1$, $R^2$, and $R^3$ is deuterium. In some embodiments, at least two of $R^1$, $R^2$, and $R^3$ are deuterium. In some embodiments, each of $R^1$, $R^2$, and $R^3$ is deuterium. In some embodiments, $R^1$ is deuterium. In some embodiments $R^2$ is deuterium. In some embodiments $R^3$ is deuterium. In some embodiments $R^1$ and $R^2$ are deuterium. In some embodiments, $R^1$ and $R^3$ are deuterium. In some embodiments, $R^2$ and $R^3$ are deuterium. In some embodiments, each of $R^1$, $R^2$, and $R^3$ is hydrogen.

In some embodiments, at least one of $R^4$, $R^5$, $R^6$, and $R^7$ is deuterium. In some embodiments, at least two of $R^4$, $R^5$, $R^6$ and $R^7$ are deuterium. In some embodiments, three of $R^4$, $R^5$, $R^6$, and $R^7$ are deuterium. In some embodiments, $R^4$ is deuterium. In some embodiments, $R^5$ is deuterium. In some embodiments, $R^6$ is deuterium. In some embodiments, $R^7$ is deuterium. In some embodiments, $R^4$ and $R^5$ are deuterium. In some embodiments, $R^4$ and $R^6$ are deuterium. In some embodiments, $R^4$ and $R^7$ are deuterium. In some embodiments, $R^5$ and $R^6$ are deuterium. In some embodiments, $R^5$ and $R^7$ are deuterium. In some embodiments, $R^6$ and $R^7$ are deuterium. In some embodiments, $R^4$, $R^5$, and $R^6$ are deuterium. In some embodiments, $R^4$, $R^5$, and $R^7$ are deuterium. In some embodiments, $R^4$, $R^6$, and $R^7$ are deuterium. In some embodiments, $R^5$, $R^6$, and $R^7$ are deuterium. In some embodiments, each of $R^4$, $R^5$, $R^6$, and $R^7$ is hydrogen.

In some embodiments, one of $R^8$ and $R^9$ is deuterium. In some embodiments, $R^8$ is deuterium. In some embodiments, $R^9$ is deuterium. In some embodiments, each of $R^8$ and $R^9$ is hydrogen.

In some embodiments, at least one of $R^{10}$, $R^{11}$, and $R^{12}$ is deuterium. In some embodiments, at least two of $R^{10}$, $R^{11}$, and $R^{12}$ are deuterium. In some embodiments, each of $R^{10}$, $R^{11}$, and $R^{12}$ is deuterium. In some embodiments, $R^{10}$ is deuterium. In some embodiments, $R^{11}$ is deuterium. In some embodiments, $R^{12}$ is deuterium. In some embodiments, $R^{10}$ and $R^{11}$ are deuterium. In some embodiments, $R^{10}$ and $R^{12}$ are deuterium. In some embodiments, $R^{11}$ and $R^{12}$ are deuterium. In some embodiments, each of $R^{10}$, $R^{11}$, and $R^{12}$ is hydrogen.

In some embodiments, at least one of $R^{13}$, $R^{14}$, and $R^{15}$ is deuterium. In some embodiments, at least two of $R^{13}$, $R^{14}$, and $R^{15}$ are deuterium. In some embodiments, each of $R^{13}$, $R^{14}$, and $R^{15}$ is deuterium. In some embodiments, $R^{13}$ is deuterium. In some embodiments, $R^{14}$ is deuterium. In some embodiments, $R^{15}$ is deuterium. In some embodiments, $R^{13}$ and $R^{14}$ are deuterium. In some embodiments, $R^{13}$ and $R^{15}$ are deuterium. In some embodiments, $R^{14}$ and $R^{15}$ are deuterium. In some embodiments, each of $R^{13}$, $R^{14}$, and $R^{15}$ is hydrogen.

In some embodiments, each of $R^{13}$, $R^{14}$, and $R^{15}$ is deuterium, and $R^{10}$ is hydrogen. In some embodiments, each of $R^{13}$, $R^{14}$, and $R^{15}$ is deuterium, and $R^{11}$ is hydrogen. In some embodiments, each of $R^{13}$, $R^{14}$, and $R^{15}$ is deuterium, and $R^{12}$ is hydrogen. In some embodiments, each of $R^{13}$, $R^{14}$, and $R^{15}$ is deuterium, and $R^{10}$ and $R^{11}$ are hydrogen. In some embodiments, each of $R^{13}$, $R^{14}$, and $R^{15}$ is deuterium, and $R^{10}$ and $R^{12}$ are hydrogen. In some embodiments, each of $R^{13}$, $R^{14}$, and $R^{15}$ is deuterium, and $R^{11}$ and $R^{12}$ are hydrogen. In some embodiments, each of $R^{13}$, $R^{14}$, and $R^{15}$ is deuterium, and $R^{10}$, $R^{11}$, and $R^{12}$ are hydrogen.

In some embodiments, each of $R^{10}$, $R^{11}$, and $R^{12}$ is deuterium, and $R^{13}$ is hydrogen. In some embodiments, each of $R^{10}$, $R^{11}$, and $R^{12}$ is deuterium, and $R^{14}$ is hydrogen. In some embodiments, each of $R^{10}$, $R^{11}$, and $R^{12}$ is deuterium, and $R^{15}$ is hydrogen. In some embodiments, each of $R^{10}$, $R^{11}$, and $R^{12}$ is deuterium, and $R^{13}$ and $R^{14}$ are hydrogen. In some embodiments, each of $R^{10}$, $R^{11}$, and $R^{12}$ is deuterium, and $R^{13}$ and $R^{15}$ are hydrogen. In some embodiments, each of $R^{10}$, $R^{11}$, and $R^{12}$ is deuterium, and $R^{14}$ and $R^{15}$ are hydrogen. In some embodiments, each of $R^{10}$, $R^{11}$, and $R^{12}$ is deuterium, and $R^{13}$, $R^{14}$, and $R^{15}$ are hydrogen.

In some embodiments, each of $R^1$, $R^2$, $R^3$, $R^{13}$, $R^{14}$, and $R^{15}$ is deuterium. In some embodiments, each of $R^1$, $R^2$, $R^3$, $R^4$, $R^5$, $R^6$, $R^7$, $R^{13}$, $R^{14}$, and $R^{15}$ is deuterium. In some embodiments, each of $R^4$, $R^5$, $R^6$, $R^7$, $R^{13}$, $R^{14}$, and $R^{15}$ is deuterium. In some embodiments, each of $R^8$, $R^9$, $R^{13}$, $R^{14}$, and $R^{15}$ is deuterium. In some embodiments, each of $R^1$, $R^2$, $R^3$, $R^8$, $R^9$, $R^{13}$, $R^{14}$, and $R^{15}$ is deuterium.

In another aspect, the present disclosure provides a compound of the formula:

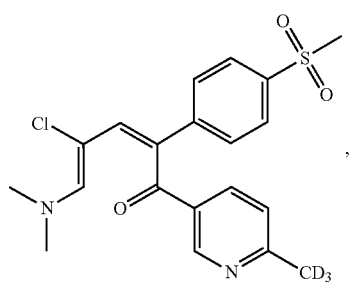

or a pharmaceutically acceptable salt, hydrate, solvate, polymorph, or co-crystal thereof.

In another aspect, the present disclosure provides a compound of the formula:

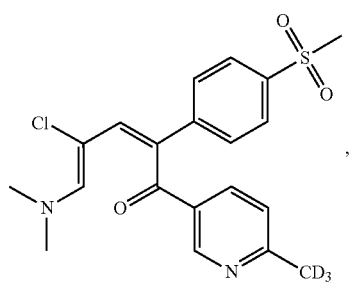

or a pharmaceutically acceptable salt thereof.

Pharmaceutical Compositions, Kits, and Administration

In another aspect, the present disclosure provides a pharmaceutical composition comprising a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof; and a pharmaceutically acceptable excipient.

In another aspect, the present disclosure provides a pharmaceutical composition comprising a compound disclosed herein (e.g., a compound of any one of Formulae (I), (II), or (III), or d3-etoricoxib), or a pharmaceutically acceptable salt, hydrate, solvate, polymorph, or co-crystal thereof; and a pharmaceutically acceptable excipient.

In another aspect, the present disclosure provides a pharmaceutical composition comprising a compound disclosed herein (e.g., a compound of any one of Formulae (I), (II), or (III), or d3-etoricoxib), or a pharmaceutically acceptable salt thereof; and a pharmaceutically acceptable excipient.

In another aspect, the present disclosure provides a pharmaceutical composition comprising a compound of the formula:

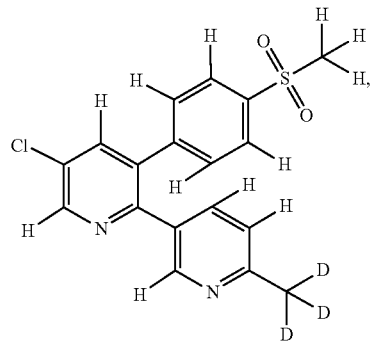

or a pharmaceutically acceptable salt, hydrate, solvate, polymorph, co-crystal, metabolite, or prodrug thereof; and a pharmaceutically acceptable excipient.

In another aspect, the present disclosure provides a pharmaceutical composition comprising a compound of the formula:

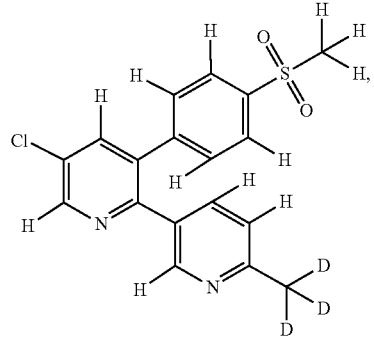

or a pharmaceutically acceptable salt, hydrate, solvate, polymorph, or co-crystal thereof; and a pharmaceutically acceptable excipient.

In another aspect, the present disclosure provides a pharmaceutical composition comprising a compound of the formula:

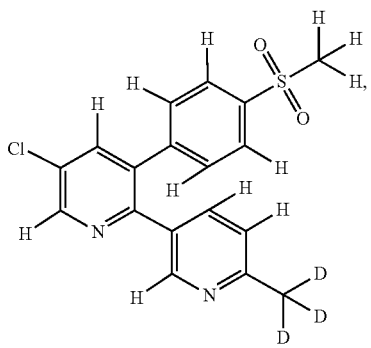

or a pharmaceutically acceptable salt thereof; and a pharmaceutically acceptable excipient.

In another aspect, the present disclosure provides a kit comprising a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof; or a pharmaceutical composition thereof; and instructions for using the compound, or a pharmaceutically acceptable salt, hydrate, solvate, polymorph, co-crystal, metabolite, or prodrug thereof, or the pharmaceutical composition.

In another aspect, the present disclosure provides a kit comprising a compound disclosed herein (e.g., a compound of any one of Formulae (I), (II), or (III), or d3-etoricoxib), or a pharmaceutically acceptable salt, hydrate, solvate, polymorph, or co-crystal thereof; or a pharmaceutical composition thereof; and instructions for using the compound, or a pharmaceutically acceptable salt, hydrate, solvate, polymorph, or co-crystal thereof, or the pharmaceutical composition.

In another aspect, the present disclosure provides a kit comprising a compound disclosed herein (e.g., a compound of any one of Formulae (I), (II), or (III), or d3-etoricoxib), or a pharmaceutically acceptable salt thereof; or a pharmaceutical composition thereof; and instructions for using the compound, or a pharmaceutically acceptable salt thereof, or the pharmaceutical composition.

In another aspect, the present disclosure provides a kit comprising a compound of the formula:

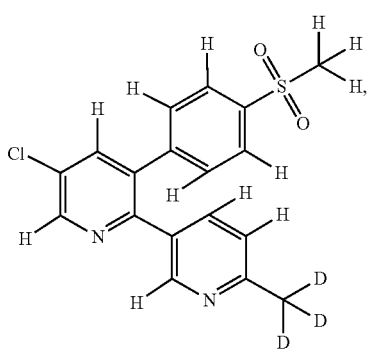

or a pharmaceutically acceptable salt, hydrate, solvate, polymorph, co-crystal, metabolite, or prodrug thereof; or a pharmaceutical composition thereof; and instructions for using the compound, or a pharmaceutically acceptable salt, hydrate, solvate, polymorph, co-crystal, metabolite, or prodrug thereof, or the pharmaceutical composition.

In another aspect, the present disclosure provides a kit comprising a compound of the formula:

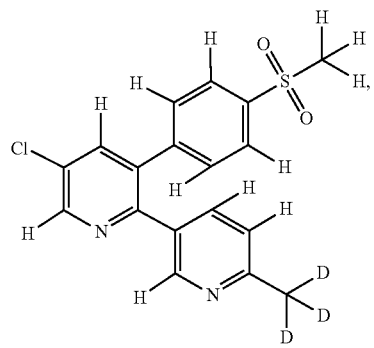

or a pharmaceutically acceptable salt, hydrate, solvate, polymorph, or co-crystal thereof; or a pharmaceutical composition thereof; and instructions for using the compound, or a pharmaceutically acceptable salt, hydrate, solvate, polymorph, or co-crystal thereof, or the pharmaceutical composition.

In another aspect, the present disclosure provides a kit comprising a compound of the formula:

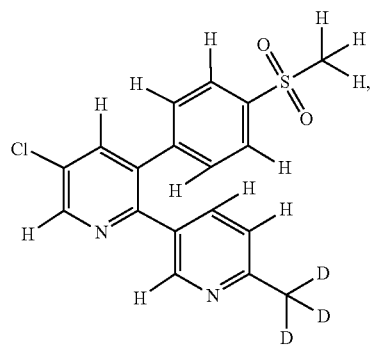

or a pharmaceutically acceptable salt thereof; or a pharmaceutical composition thereof; and instructions for using the compound, or a pharmaceutically acceptable salt thereof, or the pharmaceutical composition.

In some embodiments, the pharmaceutical composition is an oral dosage form. In some embodiments, the pharmaceutical composition is a parenteral, topical, buccal, ophthalmic, rectal, transdermal, or vaginal dosage form. In some embodiments, the pharmaceutical composition is a parenteral dosage form. In some embodiments, the pharmaceutical composition is a topical dosage form. In some embodiments the pharmaceutical composition is a buccal dosage form. In some embodiments, the pharmaceutical composition is an ophthalmic dosage form. In some embodiments, the pharmaceutical composition is a rectal dosage form. In some embodiments, the pharmaceutical composition is a transdermal dosage form. In some embodiments, the pharmaceutical composition is a vaginal dosage form.

In some embodiments, the pharmaceutical composition is an injectable dosage form. In some embodiments, the injectable dosage form is an intravenous dosage form.

In some embodiments, the pharmaceutical composition is a solid dosage formulation. In some embodiments, the solid dosage formulation is a tablet, capsule, granule, powder, sachet, or chewable dosage form.

In some embodiments, the pharmaceutical composition is a liquid dosage formulation. In some embodiments, the pharmaceutical composition is a solution. In some embodiments, pharmaceutical composition is a suspension. In some embodiments, the pharmaceutical composition is a syrup.

In some embodiments, the pharmaceutical composition achieves a higher geometric mean $C_{max}$ plasma concentration following administration of a single dose of the compound, or a pharmaceutically acceptable salt, hydrate, solvate, polymorph, co-crystal, metabolite, or prodrug thereof, or the pharmaceutical composition, to a population of patients compared to a control composition comprising non-isotopically enriched etoricoxib, or a pharmaceutically acceptable salt, hydrate, solvate, polymorph, co-crystal, metabolite, or prodrug thereof, or a pharmaceutical composition comprising etoricoxib, or a pharmaceutically acceptable salt, hydrate, solvate, polymorph, co-crystal, metabolite, or prodrug thereof, and a pharmaceutically acceptable excipient. In some embodiments, the patients are healthy patients.

In some embodiments, the geometric mean $C_{max}$ plasma concentration is at least 5% higher. In some embodiments, the geometric mean $C_{max}$ plasma concentration is at least 10%, 15%, 20%, 25%, 30%, 35%, 40%, 45%, or 50% higher. In some embodiments, the geometric mean $C_{max}$ plasma concentration is at least 10% higher. In some embodiments, the geometric mean $C_{max}$ plasma concentration is at least 15% higher. In some embodiments, the geometric mean $C_{max}$ plasma concentration is at least 20% higher. In some embodiments, the geometric mean $C_{max}$ plasma concentration is at least 25% higher. In some embodiments, the geometric mean $C_{max}$ plasma concentration is at least 30% higher. In some embodiments, the geometric mean $C_{max}$ plasma concentration is at least 35% higher. In some embodiments, the geometric mean $C_{max}$ plasma concentration is at least 40% higher. In some embodiments, the geometric mean $C_{max}$ plasma concentration is at least 45% higher. In some embodiments, the geometric mean $C_{max}$ plasma concentration is at least 50% higher.

In some embodiments, the pharmaceutical composition achieves a higher geometric mean plasma AUC following administration of a single dose of the compound, or a pharmaceutically acceptable salt, hydrate, solvate, polymorph, co-crystal, metabolite, or prodrug thereof, or the pharmaceutical composition, to a population of patients compared to a control composition comprising non-isotopically etoricoxib, or a pharmaceutically acceptable salt, hydrate, solvate, polymorph, co-crystal, metabolite, or prodrug thereof, or a pharmaceutical composition comprising etoricoxib, or a pharmaceutically acceptable salt, hydrate, solvate, polymorph, co-crystal, metabolite, or prodrug thereof, and a pharmaceutically acceptable excipient. In some embodiments, the patients are healthy patients.

In some embodiments, the geometric mean plasma AUC is at least 5% higher. In some embodiments, the geometric mean plasma AUC is at least 10%, 15%, 20%, 25%, 30%, 35%, 40%, 45%, or 50% higher. In some embodiments, the geometric mean plasma AUC is at least 10% higher. In some embodiments, the geometric mean plasma AUC is at least 15% higher. In some embodiments, the geometric mean plasma AUC is at least 20% higher. In some embodiments, the geometric mean plasma AUC is at least 25% higher. In some embodiments, the geometric mean plasma AUC is at least 30% higher. In some embodiments, the geometric mean plasma AUC is at least 35% higher. In some embodiments, the geometric mean plasma AUC is at least 40% higher. In some embodiments, the geometric mean plasma AUC is at least 45% higher. In some embodiments, the geometric mean plasma AUC is at least 50% higher.

In some embodiments, the geometric mean plasma AUC is the geometric mean plasma $AUC_{0-24}$. In some embodiments, the geometric mean plasma AUC is the geometric mean plasma $AUC_{0-\infty}$.

Pharmaceutical compositions disclosed herein can be prepared by any method known in the art of pharmaceutics. In general, such preparatory methods include bringing the compound disclosed herein (i.e., the "active ingredient") into association with a carrier or excipient, and/or one or more other accessory ingredients, and then, if necessary and/or desirable, shaping, and/or packaging the product into a desired single- or multi-dose unit.

In some embodiments, pharmaceutical compositions are prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition disclosed herein will vary, depending upon the identity, size, and/or condition of the subject treated and further depending upon the route by which the composition is to be administered. In some embodiments, the composition comprises between 0.1% and 100% (w/w) active ingredient.

Pharmaceutically acceptable excipients used in the manufacture of the disclosed pharmaceutical compositions include inert diluents, dispersing and/or granulating agents, surface active agents and/or emulsifiers, disintegrating agents, binding agents, preservatives, buffering agents, lubricating agents, and/or oils. In some embodiments, excipients such as cocoa butter and suppository waxes, coloring agents, coating agents, sweetening, flavoring, and perfuming agents are present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In some embodiments, in addition to the active ingredients, the liquid dosage forms comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates disclosed herein are mixed with solubilizing agents such as Cremophor®, alcohols, oils, modified oils, glycols, polysorbates, cyclodextrins, polymers, and mixtures thereof.

In some embodiments, injectable preparations, for example, sterile injectable aqueous or oleaginous suspensions are formulated according to the known art using suitable dispersing or wetting agents and suspending agents. In some embodiments, the sterile injectable preparation is a sterile injectable solution, suspension, or emulsion in a nontoxic parenterally acceptable diluent or solvent, for example, as a solution in 1,3-butanediol. In some embodiments, the acceptable vehicles and solvents that are employed include water, Ringer's solution, U.S.P., and isotonic sodium chloride solution. In addition, sterile, fixed oils are conventionally employed as a solvent or suspending medium. In some embodiments, any bland fixed oil is employed for this purpose, including synthetic mono- or di-glycerides. In addition, fatty acids such as oleic acid are used in the preparation of injectables.

In some embodiments, the injectable formulations are sterilized, for example, by filtration through a bacterial-retaining filter, or by incorporating sterilizing agents in the form of sterile solid compositions. In some embodiments, such sterilized injectable formulations are dissolved or dispersed in sterile water or other sterile injectable medium prior to use.

In order to prolong the effect of a drug, it is often desirable to slow the absorption of the drug from subcutaneous or intramuscular injection. In some embodiments, this is accomplished by the use of a liquid suspension of crystalline or amorphous material with poor water solubility. In some embodiments, the rate of absorption of the drug then depends upon its rate of dissolution, which, in turn, depends upon crystal size and crystalline form. Alternatively, in some embodiments, delayed absorption of a parenterally administered drug form is accomplished by dissolving or suspending the drug in an oil vehicle.

Compositions for rectal or vaginal administration are typically suppositories. In some embodiments, compositions for rectal or vaginal administrations are suppositories prepared by mixing the compounds disclosed herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In some embodiments, in the case of capsules, tablets, and pills, the dosage form includes a buffering agent.

In some embodiments, solid compositions of a similar type are employed as fillers in soft and hard-filled gelatin capsules using such excipients as lactose or milk sugar as well as high molecular weight polyethylene glycols and the like. In some embodiments, the solid dosage forms of tablets, dragees, capsules, pills, and granules are prepared with coatings and shells such as enteric coatings and other coatings well known in the art of pharmacology. In some embodiments, the solid dosage forms optionally comprise opacifying agents. In some embodiments, the solid dosage forms are of a composition that they release the active ingredient(s) only, or preferentially, in a certain part of the intestinal tract, optionally, in a delayed manner. In some embodiments, encapsulating compositions include polymeric substances and waxes. In some embodiments, solid compositions of a similar type are employed as fillers in soft and hard-filled gelatin capsules using such excipients as lactose or milk sugar as well as high molecular weight polyethylene glycols and the like.

In some embodiments, the active ingredient is in a microencapsulated form with one or more excipients as noted above. In some embodiments, the solid dosage forms of tablets, dragees, capsules, pills, and granules are prepared with coatings and shells such as enteric coatings, release controlling coatings, and other coatings well known in the pharmaceutical formulating art. In some embodiments, in such solid dosage forms the active ingredient is admixed with at least one inert diluent such as sucrose, lactose, or starch. In some embodiments, such dosage forms comprise, as is normal practice, additional substances other than inert diluents, e.g., tableting lubricants and other tableting aids such a magnesium stearate and microcrystalline cellulose. In some embodiments, in the case of capsules, tablets and pills, the dosage forms comprise buffering agents. In some embodiments, the dosage forms optionally comprise opacifying agents and are of a composition that they release the active ingredient(s) only, or preferentially, in a certain part of the intestinal tract, optionally, in a delayed manner. In some embodiments, the encapsulating agents include polymeric substances and waxes.

In some embodiments, dosage forms for topical and/or transdermal administration of a compound disclosed herein include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as required. Additionally, the present disclosure contemplates the use of transdermal patches, which often have the added advantage of providing controlled delivery of an active ingredient to the body. In some embodiments, such dosage forms are prepared, for example, by dissolving and/or dispensing the active ingredient in the proper medium. In some embodiments, alternatively or additionally, the rate is controlled by either providing a rate controlling membrane and/or by dispersing the active ingredient in a polymer matrix and/or gel.

Suitable devices for use in delivering intradermal pharmaceutical compositions disclosed herein include short needle devices. In some embodiments, intradermal compositions are administered by devices which limit the effective penetration length of a needle into the skin. In some embodiments, alternatively or additionally, conventional syringes are used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient. In some embodiments, the concentration of the active ingredient is as high as the solubility limit of the active ingredient in the solvent. In some embodiments, formulations for topical administration further comprise one or more of the additional ingredients disclosed herein.

In some embodiments, a pharmaceutical composition disclosed herein is prepared, packaged, and/or sold in a formulation suitable for pulmonary administration via the buccal cavity. In some embodiments, such a formulation comprises dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant is directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. In some embodiments, dry powder compositions include a solid fine powder diluent such as sugar and are conveniently provided in a unit dose form.

Low boiling propellants generally include liquid propellants having a boiling point of below 65° F. at atmospheric pressure. In some embodiments, the propellant constitutes 50 to 99.9% (w/w) of the composition, and the active ingredient constitutes 0.1 to 20% (w/w) of the composition. In some embodiments, the propellant further comprises additional ingredients such as a liquid non-ionic and/or solid anionic surfactant and/or a solid diluent (which may have a particle size of the same order as particles comprising the active ingredient).

In some embodiments, pharmaceutical compositions disclosed herein formulated for pulmonary delivery provide the active ingredient in the form of droplets of a solution and/or suspension. In some embodiments, such formulations are prepared, packaged, and/or sold as aqueous and/or dilute alcoholic solutions and/or suspensions, optionally sterile, comprising the active ingredient, and may conveniently be administered using any nebulization and/or atomization device. In some embodiments, such formulations further comprise one or more additional ingredients including, but not limited to, a flavoring agent such as saccharin sodium, a volatile oil, a buffering agent, a surface active agent, and/or a preservative such as methylhydroxybenzoate. In some embodiments, the droplets provided by this route of administration have an average diameter in the range from about 0.1 to about 200 nanometers.

Formulations disclosed herein as being useful for pulmonary delivery are useful for intranasal delivery of a pharmaceutical composition disclosed herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

For example, in some embodiments, formulations for nasal administration comprise from about as little as 0.1% (w/w) to as much as 100% (w/w) of the active ingredient. In some embodiments, formulations for nasal administration further comprise one or more of the additional ingredients disclosed herein. In some embodiments, a pharmaceutical composition disclosed herein is prepared, packaged, and/or sold in a formulation for buccal administration. For example, in some embodiments, such formulations are in the form of tablets and/or lozenges made using conventional methods, and contain, for example, 0.1 to 20% (w/w) active ingredient, the balance comprising an orally dissolvable and/or degradable composition and, optionally, one or more of the additional ingredients disclosed herein. Alternately, in some embodiments, formulations for buccal administration comprise a powder and/or an aerosolized and/or atomized solution and/or suspension comprising the active ingredient. In some embodiments, such powdered, aerosolized, and/or aerosolized formulations, when dispersed, have an average particle and/or droplet size in the range from about 0.1 to about 200 nanometers, and further comprise one or more of the additional ingredients disclosed herein.

In some embodiments, a pharmaceutical composition disclosed herein is prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. In some embodiments, such drops further comprise buffering agents, salts, and/or one or more other of the additional ingredients disclosed herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions disclosed herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

In some embodiments, the compounds and compositions disclosed herein are administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. In some embodiments, an effective amount is included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound disclosed herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

In some embodiments, a first dose (loading dose) of the compound is provided, followed by a second, lower dose (maintenance dose) of the compound. In some embodiments, the maintenance dose is administered for up to 3 days, up to 5 days, up to 7 days, up to 10 days, up to 14 days, or chronically thereafter.

Dose ranges as disclosed herein provide guidance for the administration of the disclosed pharmaceutical compositions to an adult. In some embodiments, the amount to be administered to, for example, a child or an adolescent is determined by a medical practitioner or person skilled in the art and is lower or the same as that administered to an adult.

In some embodiments, the pharmaceutical composition comprises about 0.1 mg to about 1,000 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 0.1 mg to about 500 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 1 mg to about 1,000 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 1 mg to about 500 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 5 mg to about 300 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 5 mg to about 250 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 5 mg to about 200 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 5 mg to about 150 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 5 mg to about 140 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 5 mg to about 130 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 5 mg to about 120 mg of a compound of any one of Formulae (I), (II), or (III), or d3-etoricoxib, or a pharmaceutically acceptable salt, hydrate, solvate, polymorph, co-crystal, metabolite, or prodrug thereof.

In certain embodiments, the pharmaceutical composition comprises about 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 80 mg, 85 mg, 90 mg, 100 mg, 110 mg, 120 mg, 140 mg, 160 mg, 180 mg, 200 mg, 220 mg, 240 mg, 260 mg, 280 mg, or 300 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 5 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 7.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 10 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 12.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 15 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 17.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 20 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 22.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 25 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 27.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 30 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 35 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 40 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 45 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 50 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 55 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 60 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 65 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 70 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 75 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 80 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 85 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 90 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 100 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 110 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 120 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 140 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 160 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 180 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 200 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 220 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 240 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 260 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 280 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 300 mg of a compound of any one of Formulae (I), (II), or (III), or d3-etoricoxib, or a pharmaceutically acceptable salt, hydrate, solvate, polymorph, co-crystal, metabolite, or prodrug thereof.

In some embodiments, the pharmaceutical composition comprises about 0.1 mg to about 1,000 mg of d3-etoricoxib, or a pharmaceutically acceptable salt, hydrate, solvate, polymorph, co-crystal, metabolite, or prodrug thereof. In some embodiments, the pharmaceutical composition comprises about 0.1 mg to about 500 mg of d3-etoricoxib, or a pharmaceutically acceptable salt, hydrate, solvate, polymorph, co-crystal, metabolite, or prodrug thereof. In some embodiments, the pharmaceutical composition comprises about 1 mg to about 1,000 mg of a compound of d3-etoricoxib, or a pharmaceutically acceptable salt, hydrate, solvate, polymorph, co-crystal, metabolite, or prodrug thereof. In some embodiments, the pharmaceutical composition comprises about 1 mg to about 500 mg of d3-etoricoxib, or a pharmaceutically acceptable salt, hydrate, solvate, polymorph, co-crystal, metabolite, or prodrug thereof. In some embodiments, the pharmaceutical composition comprises about 5 mg to about 300 mg of d3-etoricoxib, or a pharmaceutically acceptable salt, hydrate, solvate, polymorph, co-crystal, metabolite, or prodrug thereof. In certain embodiments, the pharmaceutical composition comprises about 5 mg to about 250 mg of d3-etoricoxib, or a pharmaceutically acceptable salt, hydrate, solvate, polymorph, co-crystal, metabolite, or prodrug thereof. In some embodiments, the pharmaceutical composition comprises about 5 mg to about 200 mg of d3-etoricoxib, or a pharmaceutically acceptable salt, hydrate, solvate, polymorph, co-crystal, metabolite, or prodrug thereof. In certain embodiments, the pharmaceutical composition comprises about 5 mg to about 150 mg of d3-etoricoxib, or a pharmaceutically acceptable salt, hydrate, solvate, polymorph, co-crystal, metabolite, or prodrug thereof. In some embodiments, the pharmaceutical composition comprises about 5 mg to about 140 mg of d3-etoricoxib, or a pharmaceutically acceptable salt, hydrate, solvate, polymorph, co-crystal, metabolite, or prodrug thereof. In certain embodiments, the pharmaceutical composition comprises about 5 mg to about 130 mg of d3-etoricoxib, or a pharmaceutically acceptable salt, hydrate, solvate, polymorph, co-crystal, metabolite, or prodrug thereof. In some embodiments, the pharmaceutical composition comprises about 5 mg to about 120 mg of d3-etoricoxib, or a pharmaceutically acceptable salt, hydrate, solvate, polymorph, co-crystal, metabolite, or prodrug thereof.

In certain embodiments, the pharmaceutical composition comprises about 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 80 mg, 85 mg, 90 mg, 100 mg, 110 mg, 120 mg, 140 mg, 160 mg, 180 mg, 200 mg, 220 mg, 240 mg, 260 mg, 280 mg, or 300 mg of d3-etoricoxib, or a pharmaceutically acceptable salt, hydrate, solvate, polymorph, co-crystal, metabolite, or prodrug thereof. In some embodiments, the pharmaceutical composition comprises about 5 mg of d3-etoricoxib, or a pharmaceutically acceptable salt, hydrate, solvate, polymorph, co-crystal, metabolite, or prodrug thereof. In certain embodiments, the pharmaceutical composition comprises about 7.5 mg of d3-etoricoxib, or a pharmaceutically acceptable salt, hydrate, solvate, polymorph, co-crystal, metabolite, or prodrug thereof. In some embodiments, the pharmaceutical composition comprises about 10 mg of d3-etoricoxib, or a pharmaceutically acceptable salt, hydrate, solvate, polymorph, co-crystal, metabolite, or prodrug thereof. In certain embodiments, the pharmaceutical composition comprises about 12.5 mg of d3-etoricoxib, or a pharmaceutically acceptable salt, hydrate, solvate, polymorph, co-crystal, metabolite, or prodrug thereof. In some embodiments, the pharmaceutical composition comprises about 15 mg of d3-etoricoxib, or a pharmaceutically acceptable salt, hydrate, solvate, polymorph, co-crystal, metabolite, or prodrug thereof. In certain embodiments, the pharmaceutical composition comprises about 17.5 mg of d3-etoricoxib, or a pharmaceutically acceptable salt, hydrate, solvate, polymorph, co-crystal, metabolite, or prodrug thereof. In some embodiments, the pharmaceutical composition comprises about 20 mg of d3-etoricoxib, or a pharmaceutically acceptable salt, hydrate, solvate, polymorph, co-crystal, metabolite, or prodrug thereof. In certain embodiments, the pharmaceutical composition comprises about 22.5 mg of d3-etoricoxib, or a pharmaceutically acceptable salt, hydrate, solvate, polymorph, co-crystal, metabolite, or prodrug thereof. In some embodiments, the pharmaceutical composition comprises about 25 mg of d3-etoricoxib, or a pharmaceutically acceptable salt, hydrate, solvate, polymorph, co-crystal, metabolite, or prodrug thereof. In certain embodiments, the pharmaceutical composition comprises about 27.5 mg of d3-etoricoxib, or a pharmaceutically acceptable salt, hydrate, solvate, polymorph, co-crystal, metabolite, or prodrug thereof. In some embodiments, the pharmaceutical composition comprises about 30 mg of d3-etoricoxib, or a pharmaceutically acceptable salt, hydrate, solvate, polymorph, co-crystal, metabolite, or prodrug thereof. In certain embodiments, the pharmaceutical composition comprises about 35 mg of d3-etoricoxib, or a pharmaceutically acceptable salt, hydrate, solvate, polymorph, co-crystal, metabolite, or prodrug thereof. In some embodiments, the pharmaceutical composition comprises about 40 mg of d3-etoricoxib, or a pharmaceutically acceptable salt, hydrate, solvate, polymorph, co-crystal, metabolite, or prodrug thereof. In certain embodiments, the pharmaceutical composition comprises about 45 mg of d3-etoricoxib, or a pharmaceutically acceptable salt, hydrate, solvate, polymorph, co-crystal, metabolite, or prodrug thereof. In some embodiments, the pharmaceutical composition comprises about 50 mg of d3-etoricoxib, or a pharmaceutically acceptable salt, hydrate, solvate, polymorph, co-crystal, metabolite, or prodrug thereof. In certain embodiments, the pharmaceutical composition comprises about 55 mg of d3-etoricoxib, or a pharmaceutically acceptable salt, hydrate, solvate, polymorph, co-crystal, metabolite, or prodrug thereof. In some embodiments, the pharmaceutical composition comprises about 60 mg of d3-etoricoxib, or a pharmaceutically acceptable salt, hydrate, solvate, polymorph, co-crystal, metabolite, or prodrug thereof. In certain embodiments, the pharmaceutical composition comprises about 65 mg of d3-etoricoxib, or a pharmaceutically acceptable salt, hydrate, solvate, polymorph, co-crystal, metabolite, or prodrug thereof. In some embodiments, the pharmaceutical composition comprises about 70 mg of d3-etoricoxib, or a pharmaceutically acceptable salt, hydrate, solvate, polymorph, co-crystal, metabolite, or prodrug thereof. In certain embodiments, the pharmaceutical composition comprises about 75 mg of d3-etoricoxib, or a pharmaceutically acceptable salt, hydrate, solvate, polymorph, co-crystal, metabolite, or prodrug thereof. In some embodiments, the pharmaceutical composition comprises about 80 mg of d3-etoricoxib, or a pharmaceutically acceptable salt, hydrate, solvate, polymorph, co-crystal, metabolite, or prodrug thereof. In certain embodiments, the pharmaceutical composition comprises about 85 mg of d3-etoricoxib, or a pharmaceutically acceptable salt, hydrate, solvate, polymorph, co-crystal, metabolite, or prodrug thereof. In some embodiments, the pharmaceutical composition comprises about 90 mg of d3-etoricoxib, or a pharmaceutically acceptable salt, hydrate, solvate, polymorph, co-crystal, metabolite, or prodrug thereof. In certain embodiments, the pharmaceutical composition comprises about 100 mg of d3-etoricoxib, or a pharmaceutically acceptable salt, hydrate, solvate, polymorph, co-crystal, metabolite, or prodrug thereof. In some embodiments, the pharmaceutical composition comprises about 110 mg of d3-etoricoxib, or a pharmaceutically acceptable salt, hydrate, solvate, polymorph, co-crystal, metabolite, or prodrug thereof. In certain embodiments, the pharmaceutical composition comprises about 120 mg of d3-etoricoxib, or a pharmaceutically acceptable salt, hydrate, solvate, polymorph, co-crystal, metabolite, or prodrug thereof. In some embodiments, the pharmaceutical composition comprises about 140 mg of d3-etoricoxib, or a pharmaceutically acceptable salt, hydrate, solvate, polymorph, co-crystal, metabolite, or prodrug thereof. In certain embodiments, the pharmaceutical composition comprises about 160 mg of d3-etoricoxib, or a pharmaceutically acceptable salt, hydrate, solvate, polymorph, co-crystal, metabolite, or prodrug thereof. In some embodiments, the pharmaceutical composition comprises about 180 mg of d3-etoricoxib, or a pharmaceutically acceptable salt, hydrate, solvate, polymorph, co-crystal, metabolite, or prodrug thereof. In certain embodiments, the pharmaceutical composition comprises about 200 mg of d3-etoricoxib, or a pharmaceutically acceptable salt, hydrate, solvate, polymorph, co-crystal, metabolite, or prodrug thereof. In some embodiments, the pharmaceutical composition comprises about 220 mg of d3-etoricoxib, or a pharmaceutically acceptable salt, hydrate, solvate, polymorph, co-crystal, metabolite, or prodrug thereof. In certain embodiments, the pharmaceutical composition comprises about 240 mg of d3-etoricoxib, or a pharmaceutically acceptable salt, hydrate, solvate, polymorph, co-crystal, metabolite, or prodrug thereof. In some embodiments, the pharmaceutical composition comprises about 260 mg of d3-etoricoxib, or a pharmaceutically acceptable salt, hydrate, solvate, polymorph, co-crystal, metabolite, or prodrug thereof. In certain embodiments, the pharmaceutical composition comprises about 280 mg of d3-etoricoxib, or a pharmaceutically acceptable salt, hydrate, solvate, polymorph, co-crystal, metabolite, or prodrug thereof. In some embodiments, the pharmaceutical composition comprises about 300 mg of d3-etoricoxib, or a pharmaceutically acceptable salt, hydrate, solvate, polymorph, co-crystal, metabolite, or prodrug thereof.

In some embodiments, the pharmaceutical composition comprises about 0.1 mg/mL to about 25 mg/mL of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 0.1 mg/mL to about 10 mg/mL of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 1 mg/mL to about 25 mg/mL of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 1 mg/mL to about 10 mg/mL of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 0.1 mg/mL to about 2 mg/mL of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 0.1 mg/mL to about 5 mg/mL of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 5 mg/mL to about 10 mg/mL of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 10 mg/mL to about 15 mg/mL of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 15 mg/mL to about 20 mg/mL of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 20 mg/mL to about 25 mg/mL of a compound of any one of Formulae (I), (II), or (III), or d3-etoricoxib, or a pharmaceutically acceptable salt, hydrate, solvate, polymorph, co-crystal, metabolite, or prodrug thereof.

In some embodiments, the pharmaceutical composition comprises about 0.1 mg/mL, 0.5 mg/mL, 1 mg/mL, 2 mg/mL, 5 mg/mL, 7.5 mg/mL, 10 mg/mL, 12.5 mg/mL, 15 mg/mL, 17.5 mg/mL, 20 mg/mL, 22.5 mg/mL, or 25 mg/mL. In some embodiments, the pharmaceutical composition comprises about 0.1 mg/mL. In some embodiments, the pharmaceutical composition comprises about 0.5 mg/mL. In some embodiments, the pharmaceutical composition comprises about 1 mg/mL. In some embodiments, the pharmaceutical composition comprises about 2 mg/mL. In some embodiments, the pharmaceutical composition comprises about 5 mg/mL. In some embodiments, the pharmaceutical composition comprises about 7.5 mg/mL. In some embodiments, the pharmaceutical composition comprises about 10 mg/mL. In some embodiments, the pharmaceutical composition comprises about 12.5 mg/mL. In some embodiments, the pharmaceutical composition comprises about 15 mg/mL. In some embodiments, the pharmaceutical composition comprises about 17.5 mg/mL. In some embodiments, the pharmaceutical composition comprises about 20 mg/mL. In some embodiments, the pharmaceutical composition comprises about 22.5 mg/mL. In some embodiments, the pharmaceutical composition comprises about 25 mg/mL.

In certain embodiments, the pharmaceutical composition comprises about 0.1 mg/kg to about 25 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 0.1 mg/kg to about 20 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 0.1 mg/kg to about 15 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 0.1 mg/kg to about 10 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 0.1 mg/kg to about 5 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 1 mg/kg to about 25 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 1 mg/kg to about 20 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 1 mg/kg to about 15 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 1 mg/kg to about 10 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 1 mg/kg to about 5 mg/kg of a compound of any one of Formulae (I), (II), or (III), or d3-etoricoxib, or a pharmaceutically acceptable salt, hydrate, solvate, polymorph, co-crystal, metabolite, or prodrug thereof.

In certain embodiments, the pharmaceutical composition comprises about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, or about 25 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 0.1 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 0.5 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 1 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 2 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 3 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 4 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 5 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 6 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 7 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 8 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 9 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 10 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 11 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 12 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 13 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 14 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 15 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 16 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 17 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 18 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 19 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the pharmaceutical composition comprises about 20 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the pharmaceutical composition comprises about 25 mg/kg, of a compound of any one of Formulae (I), (II), or (III), or d3-etoricoxib, or a pharmaceutically acceptable salt, hydrate, solvate, polymorph, co-crystal, metabolite, or prodrug thereof.

In certain embodiments, the pharmaceutical composition comprises about 0.1 mg/kg to about 25 mg/kg of d3-etoricoxib, or a pharmaceutically acceptable salt, hydrate, solvate, polymorph, co-crystal, metabolite, or prodrug thereof. In some embodiments, the pharmaceutical composition comprises about 0.1 mg/kg to about 20 mg/kg of d3-etoricoxib, or a pharmaceutically acceptable salt, hydrate, solvate, polymorph, co-crystal, metabolite, or prodrug thereof. In certain embodiments, the pharmaceutical composition comprises about 0.1 mg/kg to about 15 mg/kg of d3-etoricoxib, or a pharmaceutically acceptable salt, hydrate, solvate, polymorph, co-crystal, metabolite, or prodrug thereof. In some embodiments, the pharmaceutical composition comprises about 0.1 mg/kg to about 10 mg/kg of d3-etoricoxib, or a pharmaceutically acceptable salt, hydrate, solvate, polymorph, co-crystal, metabolite, or prodrug thereof. In certain embodiments, the pharmaceutical composition comprises about 0.1 mg/kg to about 5 mg/kg of d3-etoricoxib, or a pharmaceutically acceptable salt, hydrate, solvate, polymorph, co-crystal, metabolite, or prodrug thereof. In some embodiments, the pharmaceutical composition comprises about 1 mg/kg to about 25 mg/kg of d3-etoricoxib, or a pharmaceutically acceptable salt, hydrate, solvate, polymorph, co-crystal, metabolite, or prodrug thereof. In certain embodiments, the pharmaceutical composition comprises about 1 mg/kg to about 20 mg/kg of d3-etoricoxib, or a pharmaceutically acceptable salt, hydrate, solvate, polymorph, co-crystal, metabolite, or prodrug thereof. In some embodiments, the pharmaceutical composition comprises about 1 mg/kg to about 15 mg/kg of d3-etoricoxib, or a pharmaceutically acceptable salt, hydrate, solvate, polymorph, co-crystal, metabolite, or prodrug thereof. In certain embodiments, the pharmaceutical composition comprises about 1 mg/kg to about 10 mg/kg of d3-etoricoxib, or a pharmaceutically acceptable salt, hydrate, solvate, polymorph, co-crystal, metabolite, or prodrug thereof. In some embodiments, the pharmaceutical composition comprises about 1 mg/kg to about 5 mg/kg of d3-etoricoxib, or a pharmaceutically acceptable salt, hydrate, solvate, polymorph, co-crystal, metabolite, or prodrug thereof.

In certain embodiments, the pharmaceutical composition comprises about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, or about 25 mg/kg of d3-etoricoxib, or a pharmaceutically acceptable salt, hydrate, solvate, polymorph, co-crystal, metabolite, or prodrug thereof. In some embodiments, the pharmaceutical composition comprises about 0.1 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 0.5 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 1 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 2 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 3 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 4 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 5 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 6 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 7 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 8 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 9 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 10 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 11 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 12 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 13 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 14 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 15 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 16 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 17 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 18 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 19 mg/kg, of d3-etoricoxib, or a pharmaceutically acceptable salt, hydrate, solvate, polymorph, co-crystal, metabolite, or prodrug thereof. In certain embodiments, the pharmaceutical composition comprises about 20 mg/kg, of d3-etoricoxib, or a pharmaceutically acceptable salt, hydrate, solvate, polymorph, co-crystal, metabolite, or prodrug thereof. In some embodiments, the pharmaceutical composition comprises about 25 mg/kg, of d3-etoricoxib, or a pharmaceutically acceptable salt, hydrate, solvate, polymorph, co-crystal, metabolite, or prodrug thereof.

In some embodiments, the pharmaceutical composition comprises d3-etoricoxib, or a pharmaceutically acceptable salt, hydrate, solvate, polymorph, co-crystal, metabolite, or prodrug thereof, wherein d3-etoricoxib has an isotopic purity of at least 50.0%, 60.0%, 70.0%, 75.0%, 80.0%, 85.0%, 90.0%, 95.0%, 97.0%, 98.0%, 99.0%, 99.5%, 99.7%, 99.8%, or 99.9%. In some embodiments, d3-etoricoxib, or a pharmaceutically acceptable salt, hydrate, solvate, polymorph, co-crystal, metabolite, or prodrug thereof, has an isotopic purity of at least 50.0%. In some embodiments, d3-etoricoxib, or a pharmaceutically acceptable salt, hydrate, solvate, polymorph, co-crystal, metabolite, or prodrug thereof, has an isotopic purity of at least 60.0%. In some embodiments, d3-etoricoxib, or a pharmaceutically acceptable salt, hydrate, solvate, polymorph, co-crystal, metabolite, or prodrug thereof, has an isotopic purity of at least 70.0%. In some embodiments, d3-etoricoxib, or a pharmaceutically acceptable salt, hydrate, solvate, polymorph, co-crystal, metabolite, or prodrug thereof, has an isotopic purity of at least 75.0%. In some embodiments, d3-etoricoxib, or a pharmaceutically acceptable salt, hydrate, solvate, polymorph, co-crystal, metabolite, or prodrug thereof, has an isotopic purity of at least 80.0%. In some embodiments, d3-etoricoxib, or a pharmaceutically acceptable salt, hydrate, solvate, polymorph, co-crystal, metabolite, or prodrug thereof, has an isotopic purity of at least 85.0%. In some embodiments, d3-etoricoxib, or a pharmaceutically acceptable salt, hydrate, solvate, polymorph, co-crystal, metabolite, or prodrug thereof, has an isotopic purity of at least 90.0%. In some embodiments, d3-etoricoxib, or a pharmaceutically acceptable salt, hydrate, solvate, polymorph, co-crystal, metabolite, or prodrug thereof, has an isotopic purity of at least 95.0%. In some embodiments, d3-etoricoxib, or a pharmaceutically acceptable salt, hydrate, solvate, polymorph, co-crystal, metabolite, or prodrug thereof, has an isotopic purity of at least 97.0%. In some embodiments, d3-etoricoxib, or a pharmaceutically acceptable salt, hydrate, solvate, polymorph, co-crystal, metabolite, or prodrug thereof, has an isotopic purity of at least 98.0%. In some embodiments, d3-etoricoxib, or a pharmaceutically acceptable salt, hydrate, solvate, polymorph, co-crystal, metabolite, or prodrug thereof, has an isotopic purity of at least 99.0%. In some embodiments, d3-etoricoxib, or a pharmaceutically acceptable salt, hydrate, solvate, polymorph, co-crystal, metabolite, or prodrug thereof, has an isotopic purity of at least 99.5%. In some embodiments, d3-etoricoxib, or a pharmaceutically acceptable salt, hydrate, solvate, polymorph, co-crystal, metabolite, or prodrug thereof, has an isotopic purity of at least 99.7%. In some embodiments, d3-etoricoxib, or a pharmaceutically acceptable salt, hydrate, solvate, polymorph, co-crystal, metabolite, or prodrug thereof, has an isotopic purity of at least 99.9%.

In some embodiments, the pharmaceutical composition comprises a compound that is isotopically enriched with deuterium at $R^{13}$, $R^{14}$, and $R^{15}$ by at least 50.0%, at least 60.0%, at least 70.0%, at least 75.0%, at least 80.0%, at least 85.0%, at least 90.0%, at least 94.0%, at least 95.0%, at least 96.0%, at least 97.0%, at least 98.0%, at least 99.0%, at least 99.5%, at least 99.7%, at least 99.8%, at least 99.9%, or at least 100%. In some embodiments, the compound is isotopically enriched with deuterium at $R^{13}$, $R^{14}$, and $R^{15}$ by at least 50.0%. In some embodiments, the compound is isotopically enriched at with deuterium $R^{13}$, $R^{14}$, and $R^{15}$ by at least 60.0%. In some embodiments, the compound is isotopically enriched with deuterium at $R^{13}$, $R^{14}$, and $R^{15}$ by at least 70.0%. In some embodiments, the compound is isotopically enriched with deuterium at $R^{13}$, $R^{14}$, and $R^{15}$ by at least 80.0%. In some embodiments, the compound is isotopically enriched with deuterium at $R^{13}$, $R^{14}$, and $R^{15}$ by at least 90.0%. In some embodiments, the compound is isotopically enriched with deuterium at $R^{13}$, $R^{14}$, and $R^{15}$ by at least 94.0%. In some embodiments, the compound is isotopically enriched with deuterium at $R^{13}$, $R^{14}$, and $R^{15}$ by at least 95.0%. In some embodiments, the compound is isotopically enriched with deuterium at $R^{13}$, $R^{14}$, and $R^{15}$ by at least 96.0%. In some embodiments, the compound is isotopically enriched with deuterium at $R^{13}$, $R^{14}$, and $R^{15}$ by at least 97.0%. In some embodiments, the compound is isotopically enriched with deuterium at $R^{13}$, $R^{14}$, and $R^{15}$ by at least 98.0%. In some embodiments, the compound is isotopically enriched with deuterium at $R^{13}$, $R^{14}$, and $R^{15}$ by at least 99.0%. In some embodiments, the compound is isotopically enriched with deuterium at $R^{13}$, $R^{14}$, and $R^{15}$ by at least 99.5%. In some embodiments, the compound is isotopically enriched with deuterium at $R^{13}$, $R^{14}$, and $R^{15}$ by at least 99.7%. In some embodiments, the compound is isotopically enriched with deuterium at $R^{13}$, $R^{14}$, and $R^{15}$ by at least 99.8%. In some embodiments, the compound is isotopically enriched with deuterium at $R^{13}$, $R^{14}$, and $R^{15}$ by at least 99.9%. In some embodiments, the compound is isotopically enriched with deuterium at $R^{13}$, $R^{14}$, and $R^{15}$ by at least 100%.

In some embodiments, a compound or composition, as disclosed herein, is administered in combination with one or more additional pharmaceutical agents (e.g., therapeutically and/or prophylactically active agents). In some embodiments, the compounds or compositions are administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition disclosed herein including a compound disclosed herein and an additional pharmaceutical agent shows a synergistic effect that is absent in a pharmaceutical composition including one of the compound and the additional pharmaceutical agent, but not both. In some embodiments, the additional pharmaceutical agent achieves a desired effect for the same disorder. In some embodiments, the additional pharmaceutical agent achieves different effects.

In some embodiments, the pharmaceutical composition further comprises one or more additional agents. In some embodiments, the compound or composition is administered concurrently with, prior to, or subsequent to one or more additional pharmaceutical agents. For example, the one or more additional pharmaceutical agents are useful as combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. The additional pharmaceutical agents include, but are not limited to, anti-proliferative agents, anti-cancer agents, anti-angiogenesis agents, steroidal or non-steroidal anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, anesthetics, anti-coagulants, inhibitors of an enzyme, steroidal agents, steroidal or antihistamine, antigens, vaccines, antibodies, decongestant, sedatives, opioids, analgesics, anti-pyretics, hormones, and prostaglandins.

In some embodiments, each additional pharmaceutical agent is administered at a dose and/or on a time schedule determined for that pharmaceutical agent. In some embodiments, the additional pharmaceutical agents are administered together with each other and/or with the compound or composition disclosed herein in a single dose or composition or administered separately in different doses or compositions. The particular combination to employ in a regimen will take into account compatibility of the compound disclosed herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional agent is ergotamine, an anti-inflammatory agent, a steroid, a barbiturate, an opioid analgesic, caffeine, or a combination thereof. In some embodiments, the additional agent is ergotamine. In certain embodiments, the additional agent is an anti-inflammatory agent. In some embodiments, the anti-inflammatory agent is one or more of a cyclooxygenase-2 (COX-2) inhibitor, a cyclooxygenase-3 (COX-3) inhibitor, a non-steroidal anti-inflammatory drug (NSAID), or a combination thereof. In certain embodiments, the anti-inflammatory agent is a cyclooxygenase-2 (COX-2) inhibitor. In some embodiments, the COX-2 inhibitor is celecoxib, valdecoxib, rofecoxib, or a combination thereof. In certain embodiments, the anti-inflammatory agent is a cyclooxygenase-3 (COX-3) inhibitor. In some embodiments, the COX-3 inhibitor is acetaminophen, phenacetin, antipyrine, dipyrone, or a combination thereof. In certain embodiments, the anti-inflammatory agent is a non-steroidal anti-inflammatory drug (NSAID). In some embodiments, the NSAID is ibuprofen, naproxen, sulindac, ketoprofen, tolmetin, etodolac, fenoprofen, diclofenac, flurbiprofen, piroxicam, ketorolac, indomethacin, nabumetone, oxaprozin, mefanamic acid, diflunisal, or a combination thereof. In certain embodiments, the additional agent is a steroid. In some embodiments, the additional agent is a barbiturate. In certain embodiments, the barbiturate is secobarbital, mephobarbital, pentobarbital, butabarbital, phenobarbital, amobarbital, or a combination thereof. In some embodiments, the additional agent is an opioid analgesic. In certain embodiments, the opioid analgesic is codeine, fentanyl, hydrocodone, hydromorphone, meperidine, methadone, morphine, oxycodone, or a combination thereof.

Also encompassed by the disclosure are kits (e.g., pharmaceutical packs). In some embodiments, the kits disclosed herein comprise a pharmaceutical composition or compound disclosed herein and a container (e.g., a vial, ampule, bottle, syringe, and/or dispenser package, or other suitable container). In some embodiments, the disclosed kits optionally further include a second container comprising a pharmaceutical excipient for dilution or suspension of a pharmaceutical composition or compound disclosed herein. In some embodiments, the pharmaceutical composition or compound disclosed herein provided in the first container and the second container are combined to form one unit dosage form.

Thus, in one embodiment, disclosed herein are kits including a first container comprising a compound or pharmaceutical composition disclosed herein. In certain embodiments, the kits are useful for treating pain, fever, or inflammation in a subject in need thereof. In certain embodiments, the kits are useful for preventing pain, fever, or inflammation in a subject in need thereof. In certain embodiments, the kits are useful for reducing the risk of developing pain, fever, or inflammation in a subject in need thereof. In certain embodiments, the kits are useful for inhibiting the activity of COX-2 in a subject or cell.

In certain embodiments, a kit disclosed herein further includes instructions for using the kit. In some embodiments, a kit disclosed herein also includes information as required by a regulatory agency such as the U.S. Food and Drug Administration (FDA). In certain embodiments, the information included in the kits is prescribing information. In certain embodiments, the kits and instructions provide for treating pain, fever, or inflammation in a subject in need thereof. In certain embodiments, the kits and instructions provide for preventing pain, fever, or inflammation in a subject in need thereof. In certain embodiments, the kits and instructions provide for reducing the risk of developing pain, fever, or inflammation in a subject in need thereof. In certain embodiments, the kits and instructions provide for inhibiting the activity of COX-2 in a subject or cell. In some embodiments, a kit disclosed herein includes one or more additional pharmaceutical agents disclosed herein as a separate composition.

Methods of Use

In another aspect, the present disclosure provides a method for treating pain, fever, or inflammation in a subject in need thereof comprising administering to the subject a therapeutically effective amount of a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof, or a pharmaceutical composition thereof.

In another aspect, the present disclosure provides a method for preventing pain, fever, or inflammation in a subject in need thereof comprising administering to the subject a prophylactically effective amount of a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof, or a pharmaceutical composition thereof.

In another aspect, the present disclosure provides the use of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, in the manufacture of a medicament for treating pain, fever, or inflammation in a subject in need thereof.

In another aspect, the present disclosure provides the use of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, in the manufacture of a medicament for preventing pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in treating pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in preventing pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in therapy.

In another aspect, the present disclosure provides a method of inhibiting cyclooxygenase (COX) activity in vitro comprising contacting a cell, tissue, or biological sample with a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of a compound disclosed herein (e.g., a compound of any one of Formulae (I), (II), or (III), or d3-etoricoxib), or a pharmaceutically acceptable salt, hydrate, solvate, polymorph, co-crystal, metabolite, or prodrug thereof, or a pharmaceutical composition thereof.

In another aspect, the present disclosure provides the use of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, in the manufacture of a medicament for inhibiting COX-2 activity in a subject in need thereof.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of a compound disclosed herein (e.g., a compound of any one of Formulae (I), (II), or (III), or d3-etoricoxib), or a pharmaceutically acceptable salt, hydrate, solvate, polymorph, or co-crystal thereof, or a pharmaceutical composition thereof.

In another aspect, the present disclosure provides a method for preventing pain, fever, or inflammation in a subject in need thereof comprising administering to the subject a prophylactically effective amount of a compound disclosed herein (e.g., a compound of any one of Formulae (I), (II), or (III), or d3-etoricoxib), or a pharmaceutically acceptable salt, hydrate, solvate, polymorph, or co-crystal thereof, or a pharmaceutical composition thereof.

In another aspect, the present disclosure provides the use of a compound of any one of Formulae (I), (II), or (III), or d3-etoricoxib, or a pharmaceutically acceptable salt, hydrate, solvate, polymorph, or co-crystal thereof, or a pharmaceutical composition thereof, in the manufacture of a medicament for treating pain, fever, or inflammation in a subject in need thereof.

In another aspect, the present disclosure provides the use of a compound of any one of Formulae (I), (II), or (III), or d3-etoricoxib, or a pharmaceutically acceptable salt, hydrate, solvate, polymorph, or co-crystal thereof, or a pharmaceutical composition thereof, in the manufacture of a medicament for preventing pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in treating pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in preventing pain, fever, or inflammation in a subject in need thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in therapy.

In another aspect, the present disclosure provides a method of inhibiting cyclooxygenase (COX) activity in vitro comprising contacting a cell, tissue, or biological sample with a compound disclosed herein (e.g., a compound of any one of Formulae (I), (II), or (III), or d3-etoricoxib), or a pharmaceutically acceptable salt, hydrate, solvate, polymorph, or co-crystal thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with a compound disclosed herein (e.g., a compound of any one of Formulae (I), (II), or (III), or d3-etoricoxib), or a pharmaceutically acceptable salt, hydrate, solvate, polymorph, or co-crystal thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of a compound disclosed herein (e.g., a compound of any one of Formulae (I), (II), or (III), or d3-etoricoxib), or a pharmaceutically acceptable salt, hydrate, solvate, polymorph, or co-crystal thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of a compound disclosed herein (e.g., a compound of any one of Formulae (I), (II), or (III), or d3-etoricoxib), or a pharmaceutically acceptable salt, hydrate, solvate, polymorph, or co-crystal thereof, or a pharmaceutical composition thereof.

In another aspect, the present disclosure provides the use of a compound of any one of Formulae (I), (II), or (III), or d3-etoricoxib, or a pharmaceutically acceptable salt, hydrate, solvate, polymorph, or co-crystal thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of a compound of any one of Formulae (I), (II), or (III), or d3-etoricoxib, or a pharmaceutically acceptable salt, hydrate, solvate, polymorph, or co-crystal thereof, or a pharmaceutical composition thereof, in the manufacture of a medicament for inhibiting COX-2 activity in a subject in need thereof.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt, hydrate, solvate, polymorph, or co-crystal thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of a compound disclosed herein (e.g., a compound of any one of Formulae (I), (II), or (III), or d3-etoricoxib), or a pharmaceutically acceptable salt thereof, or a pharmaceutical composition thereof.

In another aspect, the present disclosure provides a method for preventing pain, fever, or inflammation in a subject in need thereof comprising administering to the subject a prophylactically effective amount of a compound disclosed herein (e.g., a compound of any one of Formulae (I), (II), or (III), or d3-etoricoxib), or a pharmaceutically acceptable salt thereof, or a pharmaceutical composition thereof.

In another aspect, the present disclosure provides the use of a compound of any one of Formulae (I), (II), or (III), or d3-etoricoxib, or a pharmaceutically acceptable salt thereof, or a pharmaceutical composition thereof, in the manufacture of a medicament for treating pain, fever, or inflammation in a subject in need thereof.

In another aspect, the present disclosure provides the use of a compound of any one of Formulae (I), (II), or (III), or d3-etoricoxib, or a pharmaceutically acceptable salt thereof, or a pharmaceutical composition thereof, in the manufacture of a medicament for preventing pain, fever, or inflammation in a subject in need thereof.

In another aspect, the present disclosure provides a compound of any one of Formulae (I), (II), or (III), or d3-etoricoxib, or a pharmaceutically acceptable salt thereof, or a pharmaceutical composition thereof, for use in treating pain, fever, or inflammation in a subject in need thereof.

In another aspect, the present disclosure provides a compound of any one of Formulae (I), (II), or (III), or d3-etoricoxib, or a pharmaceutically acceptable salt thereof, or a pharmaceutical composition thereof, for use in preventing pain, fever, or inflammation in a subject in need thereof.

In another aspect, the present disclosure provides a compound of any one of Formulae (I), (II), or (III), or d3-etoricoxib, or a pharmaceutically acceptable salt thereof, or a pharmaceutical composition thereof, for use in therapy.

In yet another aspect, the present disclosure provides a method of inhibiting cyclooxygenase (COX) activity in vitro comprising contacting a cell, tissue, or biological sample with a compound disclosed herein (e.g., a compound of any one of Formulae (I), (II), or (III), or d3-etoricoxib), or a pharmaceutically acceptable salt thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with a compound disclosed herein (e.g., a compound of any one of Formulae (I), (II), or (III), or d3-etoricoxib), or a pharmaceutically acceptable salt thereof.

In another aspect, the present disclosure provides a compound of any one of Formulae (I), (II), or (III), or d3-etoricoxib, or a pharmaceutically acceptable salt thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of a compound disclosed herein (e.g., a compound of any one of Formulae (I), (II), or (III), or d3-etoricoxib), or a pharmaceutically acceptable salt thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of a compound disclosed herein (e.g., a compound of any one of Formulae (I), (II), or (III), or d3-etoricoxib), or a pharmaceutically acceptable salt thereof, or a pharmaceutical composition thereof.

In another aspect, the present disclosure provides the use of a compound of any one of Formulae (I), (II), or (III), or d3-etoricoxib, or a pharmaceutically acceptable salt thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of a compound of any one of Formulae (I), (II), or (III), or d3-etoricoxib, or a pharmaceutically acceptable salt thereof, or a pharmaceutical composition thereof, in the manufacture of a medicament for inhibiting COX-2 activity in a subject in need thereof.

In another aspect, the present disclosure provides a compound of any one of Formulae (I), (II), or (III), or d3-etoricoxib, or a pharmaceutically acceptable salt thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a compound of any one of Formulae (I), (II), or (III), or d3-etoricoxib, or a pharmaceutically acceptable salt thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of d3-etoricoxib, or a pharmaceutically acceptable salt, hydrate, solvate, polymorph, co-crystal, metabolite, or prodrug thereof, or a pharmaceutical composition thereof.

In another aspect, the present disclosure provides a method for preventing pain, fever, or inflammation in a subject in need thereof comprising administering to the subject a prophylactically effective amount of d3-etoricoxib, or a pharmaceutically acceptable salt, hydrate, solvate, polymorph, co-crystal, metabolite, or prodrug thereof, or a pharmaceutical composition thereof.

In another aspect, the present disclosure provides the use of d3-etoricoxib, or a pharmaceutically acceptable salt, hydrate, solvate, polymorph, co-crystal, metabolite, or prodrug thereof, or a pharmaceutical composition thereof, in the manufacture of a medicament for treating pain, fever, or inflammation in a subject in need thereof.

In another aspect, the present disclosure provides the use of d3-etoricoxib, or a pharmaceutically acceptable salt, hydrate, solvate, polymorph, co-crystal, metabolite, or prodrug thereof, or a pharmaceutical composition thereof, in the manufacture of a medicament for preventing pain, fever, or inflammation in a subject in need thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in treating pain, fever, or inflammation in a subject in need thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in preventing pain, fever, or inflammation in a subject in need thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in therapy.

In another aspect, the present disclosure provides a method of inhibiting cyclooxygenase (COX) activity in vitro comprising contacting a cell, tissue, or biological sample with d3-etoricoxib, or a pharmaceutically acceptable salt, hydrate, solvate, polymorph, co-crystal, metabolite, or prodrug thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with d3-etoricoxib, or a pharmaceutically acceptable salt, hydrate, solvate, polymorph, co-crystal, metabolite, or prodrug thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of d3-etoricoxib, or a pharmaceutically acceptable salt, hydrate, solvate, polymorph, co-crystal, metabolite, or prodrug thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of d3-etoricoxib, or a pharmaceutically acceptable salt, hydrate, solvate, polymorph, co-crystal, metabolite, or prodrug thereof, or a pharmaceutical composition thereof.

In another aspect, the present disclosure provides the use of d3-etoricoxib, or a pharmaceutically acceptable salt, hydrate, solvate, polymorph, co-crystal, metabolite, or prodrug thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of d3-etoricoxib, or a pharmaceutically acceptable salt, hydrate, solvate, polymorph, co-crystal, metabolite, or prodrug thereof, or a pharmaceutical composition thereof, in the manufacture of a medicament for inhibiting COX-2 activity in a subject in need thereof.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt, hydrate, solvate, polymorph, co-crystal, metabolite, or prodrug thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of d3-etoricoxib, or a pharmaceutically acceptable salt, hydrate, solvate, polymorph, or co-crystal thereof, or a pharmaceutical composition thereof.

In another aspect, the present disclosure provides a method for preventing pain, fever, or inflammation in a subject in need thereof comprising administering to the subject a prophylactically effective amount of d3-etoricoxib, or a pharmaceutically acceptable salt, hydrate, solvate, polymorph, or co-crystal thereof, or a pharmaceutical composition thereof.

In another aspect, the present disclosure provides the use of d3-etoricoxib, or a pharmaceutically acceptable salt, hydrate, solvate, polymorph, or co-crystal thereof, or a pharmaceutical composition thereof, in the manufacture of a medicament for treating pain, fever, or inflammation in a subject in need thereof.

In another aspect, the present disclosure provides the use of d3-etoricoxib, or a pharmaceutically acceptable salt, hydrate, solvate, polymorph, or co-crystal thereof, or a pharmaceutical composition thereof, in the manufacture of a medicament for preventing pain, fever, or inflammation in a subject in need thereof.

In another aspect, the present disclosure provides d3-etoricoxib, or a pharmaceutically acceptable salt, hydrate, solvate, polymorph, or co-crystal thereof, or a pharmaceutical composition thereof, for use in treating pain, fever, or inflammation in a subject in need thereof.

In another aspect, the present disclosure provides d3-etoricoxib, or a pharmaceutically acceptable salt, hydrate, solvate, polymorph, or co-crystal thereof, or a pharmaceutical composition thereof, for use in preventing pain, fever, or inflammation in a subject in need thereof.

In another aspect, the present disclosure provides d3-etoricoxib, or a pharmaceutically acceptable salt, hydrate, solvate, polymorph, or co-crystal thereof, or a pharmaceutical composition thereof, for use in therapy.

In yet another aspect, the present disclosure provides a method of inhibiting cyclooxygenase (COX) activity in vitro comprising contacting a cell, tissue, or biological sample with d3-etoricoxib, or a pharmaceutically acceptable salt, hydrate, solvate, polymorph, or co-crystal thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with d3-etoricoxib, or a pharmaceutically acceptable salt, hydrate, solvate, polymorph, or co-crystal thereof.

In another aspect, the present disclosure provides d3-etoricoxib, or a pharmaceutically acceptable salt, hydrate, solvate, polymorph, or co-crystal thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt, hydrate, solvate, polymorph, or co-crystal thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of d3-etoricoxib, or a pharmaceutically acceptable salt, hydrate, solvate, polymorph, or co-crystal thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of d3-etoricoxib, or a pharmaceutically acceptable salt, hydrate, solvate, polymorph, or co-crystal thereof, or a pharmaceutical composition thereof.

In another aspect, the present disclosure provides the use of d3-etoricoxib, or a pharmaceutically acceptable salt, hydrate, solvate, polymorph, or co-crystal thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of d3-etoricoxib, or a pharmaceutically acceptable salt, hydrate, solvate, polymorph, or co-crystal thereof, or a pharmaceutical composition thereof, in the manufacture of a medicament for inhibiting COX-2 activity in a subject in need thereof.

In another aspect, the present disclosure provides d3-etoricoxib, or a pharmaceutically acceptable salt, hydrate, solvate, polymorph, or co-crystal thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt, hydrate, solvate, polymorph, or co-crystal thereof, or a pharmaceutical composition thereof, for use in inhibiting COX-2 activity in a subject in need thereof.

In another aspect, the present disclosure provides a method for treating pain, fever, or inflammation in a subject in need thereof comprising administering to the subject a therapeutically effective amount of d3-etoricoxib, or a pharmaceutically acceptable salt thereof, or a pharmaceutical composition thereof.

In another aspect, the present disclosure provides a method for preventing pain, fever, or inflammation in a subject in need thereof comprising administering to the subject a prophylactically effective amount of d3-etoricoxib, or a pharmaceutically acceptable salt thereof, or a pharmaceutical composition thereof.

In another aspect, the present disclosure provides the use of d3-etoricoxib, or a pharmaceutically acceptable salt thereof, or a pharmaceutical composition thereof, in the manufacture of a medicament for treating pain, fever, or inflammation in a subject in need thereof.

In another aspect, the present disclosure provides the use of d3-etoricoxib, or a pharmaceutically acceptable salt thereof, or a pharmaceutical composition thereof, in the manufacture of a medicament for preventing pain, fever, or inflammation in a subject in need thereof.

In another aspect, the present disclosure provides d3-etoricoxib, or a pharmaceutically acceptable salt thereof, or a pharmaceutical composition thereof, for use in treating pain, fever, or inflammation in a subject in need thereof.

In another aspect, the present disclosure provides d3-etoricoxib, or a pharmaceutically acceptable salt thereof, or a pharmaceutical composition thereof, for use in preventing pain, fever, or inflammation in a subject in need thereof.

In another aspect, the present disclosure provides d3-etoricoxib, or a pharmaceutically acceptable salt thereof, or a pharmaceutical composition thereof, for use in therapy.

In yet another aspect, the present disclosure provides a method of inhibiting cyclooxygenase (COX) activity in vitro comprising contacting a cell, tissue, or biological sample with d3-etoricoxib, or a pharmaceutically acceptable salt thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In yet another aspect, the present disclosure provides a method of inhibiting COX-2 activity in vitro comprising contacting a cell, tissue, or biological sample with d3-etoricoxib, or a pharmaceutically acceptable salt thereof.

In another aspect, the present disclosure provides d3-etoricoxib, or a pharmaceutically acceptable salt thereof, or a pharmaceutical composition thereof, for use in inhibiting cyclooxygenase (COX) activity in vitro. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt thereof, or a pharmaceutical composition thereof, for use in inhibiting COX-2 activity in vitro.

In another aspect, the present disclosure provides a method of inhibiting cyclooxygenase (COX) activity in a subject in need thereof comprising administering to the subject an effective amount of d3-etoricoxib, or a pharmaceutically acceptable salt thereof, or a pharmaceutical composition thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides a method of inhibiting COX-2 activity in a subject in need thereof comprising administering to the subject an effective amount of d3-etoricoxib, or a pharmaceutically acceptable salt thereof, or a pharmaceutical composition thereof.

In another aspect, the present disclosure provides the use of d3-etoricoxib, or a pharmaceutically acceptable salt thereof, or a pharmaceutical composition thereof, in the manufacture of a medicament for inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides the use of d3-etoricoxib, or a pharmaceutically acceptable salt thereof, or a pharmaceutical composition thereof, in the manufacture of a medicament for inhibiting COX-2 activity in a subject in need thereof.

In another aspect, the present disclosure provides d3-etoricoxib, or a pharmaceutically acceptable salt thereof, or a pharmaceutical composition thereof, for use in inhibiting cyclooxygenase (COX) activity in a subject in need thereof. In some embodiments, the cyclooxygenase is one or more of COX-1, COX-2, or COX-3. In some embodiments, the cyclooxygenase is COX-1. In some embodiments, the cyclooxygenase is COX-2. In some embodiments, the cyclooxygenase is COX-3.

In another aspect, the present disclosure provides d3-etoricoxib, or a pharmaceutically acceptable salt thereof, or a pharmaceutical composition thereof, for use in inhibiting COX-2 activity in a subject in need thereof.

In some embodiments, the pain, fever, or inflammation is associated with one or more of a viral infection, the common cold, bursitis, myositis, synovitis, arthritis, a degenerative joint disease, a burn, hemophilic arthropathy, migraine, and rheumatic fever. In some embodiments, the viral infection is influenza or COVID-19. In some embodiments, the degenerative joint disease is osteoarthritis. In some embodiments, the pain is one or more of acute pain, post-operative pain, chronic musculoskeletal pain, or short-term pain. In some embodiments, the pain is one or more of low back pain, chronic low back pain, neck pain, dysmenorrhea, headache, toothache, a muscle sprain, a muscle strain, neuralgia, and a burn. In some embodiments, the short-term pain is cramp-like pain. In some embodiments, the cramp-like pain occurs before or during a menstrual period. In some embodiments, the post-operative pain is due to dental surgery. In some embodiments, the pain, fever, or inflammation is associated with one or more of osteoarthritis, rheumatoid arthritis, psoriatic arthritis, ankylosing spondylitis, and gout.

In some embodiments, the pain is acute pain. In some embodiments, the acute pain is caused by one or more of acute injury, trauma, illness, or surgery (for example, open chest surgery (including open heart surgery or bypass surgery)). Acute pain also includes, but is not limited to, one or more of headache, postoperative pain, pain caused by kidney stones, pain in the gall bladder, pain caused by stones in the gall bladder, birth pain, rheumatic pain, dental pain including toothache, pain due to sports injuries, carpal tunnel syndrome, burns, musculoskeletal sprains and strains, muscle tendon deformities, neck and shoulder pain, dyspepsia, gastric ulcer, duodenal ulcer, dysmenorrhea, as well as endometriosis.

In some embodiments, the pain is post-operative pain. In some embodiments, the post-operative pain is associated with anorectal, pelvic floor, and urogynecologic procedures (vaginal/perineal approach) (e.g., colon resection, hemorrhoidectomy, vaginal hysterectomy). In some embodiments, the pain is associated with obstetric procedures (e.g., cesarean delivery, vaginal delivery). In some embodiments, the pain is associated with breast procedures (e.g., lumpectomy, mastectomy, reconstruction, reduction). In some embodiments, the pain is associated with thoracic procedures (e.g., thoracoscopy, repair of pectus excavatum in children (Nuss procedure)). In some embodiments, the pain is associated with extremity trauma requiring surgery (e.g., amputation, open reduction, and internal fixation). In some embodiments, the pain is associated with spine procedures (e.g., fusion in both adults and children, laminectomy). In some embodiments, the pain is associated with a procedure related to a sport-related injury (e.g., ACL repair and reconstruction, joint arthroscopy, rotator cuff repair). In some embodiments, the pain is associated with joint replacement (e.g., total hip arthroplasty (THA), total knee arthroplasty (TKA)). In some embodiments, the pain is associated with laparoscopic or open abdominal wall procedures (e.g., femoral hernia, incisional hernia, inguinal hernia). In some embodiments, the pain is associated with laparoscopic abdominal procedures (e.g., appendectomy, bariatric surgery, cholecystectomy, colectomy, hysterectomy, prostatectomy). In some embodiments, the pain is associated with open abdominal procedures (e.g., appendectomy, cholecystectomy, colectomy, hysterectomy); see also Laparoscopic abdominal procedures.

In some embodiments, the pain is dental pain. In some embodiments, the pain is associated with dental surgeries (e.g., third molar extraction). In some embodiments, the pain is associated with oropharyngeal procedures (e.g., tonsillectomy).

In some embodiments, the pain is cancer pain. In some embodiments, the pain is associated dysmenorrhea. In some embodiments, the pain is associated with endometriosis. In some embodiments, the pain is associated with migraines. In some embodiments, the migraine is associated with von Willebrand's disease or in a patient having von Willebrand's disease. In some embodiments, the pain is associated with acute gouty arthritis.

In some embodiments, the pain is postpartum pain. In some embodiments, the postpartum pain is associated with postpartum depression.

In some embodiments, the method reduces the risk of developing postpartum depression.

In some embodiments, provided herein is a method for treating postpartum depression in a subject in need thereof, comprising administering to the subject a therapeutically effective amount of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof.

In some embodiments, the fever is dengue fever.

In some embodiments, the inflammation is associated with acute gouty arthritis. In some embodiments, the inflammation is associated with endometriosis.

In some embodiments, the methods disclosed herein avoid or reduce the incidence of one or more side effects or adverse reactions associated with non-isotopically enriched etoricoxib at an equivalent dose. In some embodiments, the methods disclosed herein avoid or reduce the incidence of one or more side effects or adverse reactions associated with non-isotopically enriched etoricoxib at an equivalent dose when administered by the same route of administration. In some embodiments, the method of treating pain, fever, or inflammation reduces side effects associated with the administration of non-isotopically enriched etoricoxib at an equivalent dose. In some embodiments, the method of treating pain, fever, or inflammation reduces side effects associated with the administration of non-isotopically enriched etoricoxib at an equivalent dose when administered by the same route of administration. In some embodiments, the side effect is indigestion, abdominal pain, melena, tiredness, dizziness, constipation, diarrhea, swelling (e.g., swollen ankles), heart palpitations, shortness of breath, bruising, headache, flu-like symptoms, high blood pressure, chest pains, jaundice, or liver problems.

In some embodiments, the subject is a mammal. In some embodiments, the subject is a human. In some embodiments, the subject is at least 16 years of age. In some embodiments, the subject is at most 65 years of age.

In some embodiments, the therapeutically effective amount is administered to the subject once daily. In some embodiments, the therapeutically effective amount is administered to the subject twice daily. In some embodiments, the therapeutically effective amount is administered to the subject three times daily. In some embodiments, the method further comprises administering a loading dose of the compound and a maintenance dose of the compound. In some embodiments, the therapeutically effective amount is administered with food. In some embodiments, the therapeutically effective amount is administered under fasted conditions.

In some embodiments, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 10 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 25 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 50 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 75 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 100 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 150 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 200 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 250 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 300 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 350 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 400 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 450 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 500 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 550 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 600 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 650 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 700 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 750 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 800 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 850 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day. In some embodiments, about 900 mg of a compound of any one of Formulae (I), (II), or (III), or d3-etoricoxib, or a pharmaceutically acceptable salt, hydrate, solvate, polymorph, co-crystal, metabolite, or prodrug thereof, or a pharmaceutical composition thereof, is administered to the subject per day.

In some embodiments, the method further comprises administering to the subject ergotamine, an anti-inflammatory agent, a steroid, a barbiturate, an opioid analgesic, caffeine, or a combination thereof. In some embodiments, the anti-inflammatory agent is a cyclooxygenase-2 (COX-2) inhibitor, a cyclooxygenase-3 (COX-3) inhibitor, a non-steroidal anti-inflammatory drug (NSAID), or a combination thereof. In some embodiments, the NSAID is ibuprofen, naproxen, sulindac, ketoprofen, tolmetin, etodolac, fenoprofen, diclofenac, flurbiprofen, piroxicam, ketorolac, indomethacin, nabumetone, oxaprozin, mefanamic acid, diflunisal, or a combination thereof. In some embodiments, the opioid analgesic is codeine, fentanyl, hydrocodone, hydromorphone, meperidine, methadone, morphine, oxycodone, or a combination thereof. In some embodiments, the barbiturate is secobarbital, mephobarbital, pentobarbital, butabarbital, phenobarbital, amobarbital, or a combination thereof. In some embodiments, the COX-2 inhibitor is celecoxib, valdecoxib, rofecoxib, or a combination thereof. In some embodiments, the COX-3 inhibitor is acetaminophen, phenacetin, antipyrine, dipyrone, or a combination thereof.

In some embodiments, the therapeutically effective amount is about 5 mg to about 300 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 5 mg to about 250 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 5 mg to about 200 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 5 mg to about 150 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 5 mg to about 140 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 5 mg to about 130 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 5 mg to about 120 mg of a compound of any one of Formulae (I), (II), or (III), or d3-etoricoxib, or a pharmaceutically acceptable salt, hydrate, solvate, polymorph, co-crystal, metabolite, or prodrug thereof.

In certain embodiments, the therapeutically effective amount is about 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 80 mg, 85 mg, 90 mg, 100 mg, 110 mg, 120 mg, 140 mg, 160 mg, 180 mg, 200 mg, 220 mg, 240 mg, 260 mg, 280 mg, or 300 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 5 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 7.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 10 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 12.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 15 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 17.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 20 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 22.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 25 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 27.5 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 30 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 35 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 40 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 45 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 50 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 55 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments the therapeutically effective amount is about 60 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 65 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 70 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 75 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 80 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 85 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 90 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 100 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 110 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 120 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 140 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 160 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 180 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 200 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 220 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 240 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 260 mg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 280 mg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 300 mg of a compound of any one of Formulae (I), (II), or (III), or d3-etoricoxib, or a pharmaceutically acceptable salt, hydrate, solvate, polymorph, co-crystal, metabolite, or prodrug thereof.

In certain embodiments, the therapeutically effective amount is about 0.1 mg/kg to about 25 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 0.1 mg/kg to about 20 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 0.1 mg/kg to about 15 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 0.1 mg/kg to about 10 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 0.1 mg/kg to about 5 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 1 mg/kg to about 25 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 1 mg/kg to about 20 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 1 mg/kg to about 15 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 1 mg/kg to about 10 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 1 mg/kg to about 5 mg/kg of a compound of any one of Formulae (I), (II), or (III), or d3-etoricoxib, or a pharmaceutically acceptable salt, hydrate, solvate, polymorph, co-crystal, metabolite, or prodrug thereof.

In certain embodiments, the therapeutically effective amount is about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, or about 25 mg/kg of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 0.1 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 0.5 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 1 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 2 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 3 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 4 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 5 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 6 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 7 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 8 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 9 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 10 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 11 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 12 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 13 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 14 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 15 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 16 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 17 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 18 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 19 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In certain embodiments, the therapeutically effective amount is about 20 mg/kg, of a compound of any one of Formulae (I), (II), or (III), or d3-etoricoxib, or a pharmaceutically acceptable salt, hydrate, solvate, polymorph, co-crystal, metabolite, or prodrug thereof. In some embodiments, the therapeutically effective amount is about 25 mg/kg, of a compound of any one of Formulae (I), (II), or (III), or d3-etoricoxib, or a pharmaceutically acceptable salt, hydrate, solvate, polymorph, co-crystal, metabolite, or prodrug thereof.

Methods of Preparation

In another aspect, the present disclosure provides a method of preparing a compound of Formula (I):

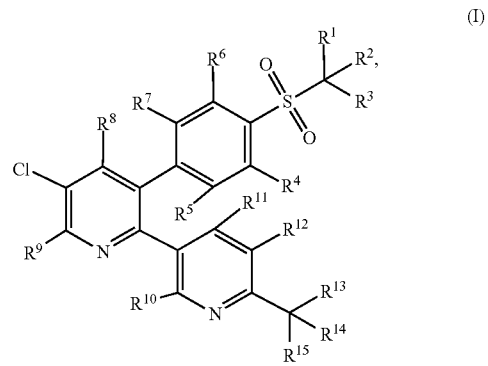

(I)

or a pharmaceutically acceptable salt, hydrate, solvate, polymorph, co-crystal, metabolite, or prodrug thereof, the method comprising contacting a compound of Formula (III):

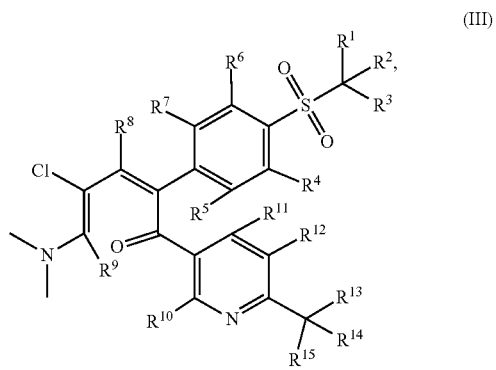

(III)

or a salt, hydrate, solvate, polymorph, or co-crystal thereof with a source of nitrogen to produce the compound of Formula (I), or a pharmaceutically acceptable salt, hydrate, solvate, polymorph, or co-crystal thereof, wherein:

each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium;

provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a method of preparing a compound of Formula (I):

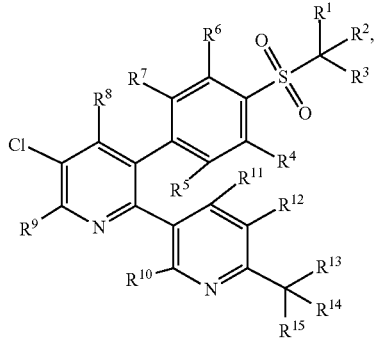

(I)

or a pharmaceutically acceptable salt, hydrate, solvate, polymorph, co-crystal, metabolite, or prodrug thereof, the method comprising:

(1) contacting a compound of Formula (II):

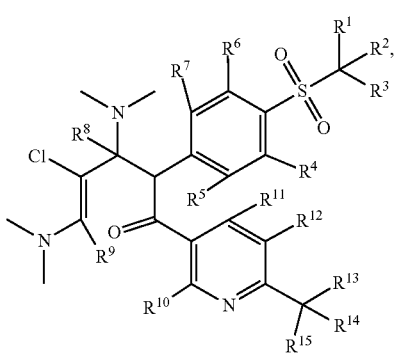

(II)

or a salt, hydrate, solvate, polymorph, or co-crystal thereof with one or more acids to produce a compound of Formula (III):

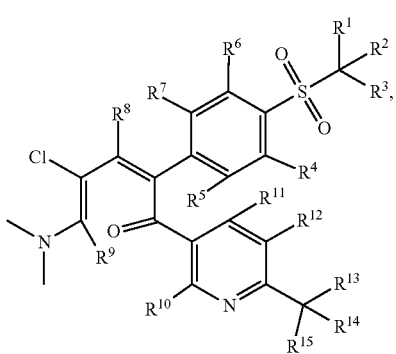

(III)

or a salt, hydrate, solvate, polymorph, or co-crystal thereof; and (2) contacting the compound of Formula (III), or a salt, hydrate, solvate, polymorph, or co-crystal thereof with a source of nitrogen to produce the compound Formula (I), or a pharmaceutically acceptable salt, hydrate, solvate, polymorph, or co-crystal thereof;

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium;

provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium.

In another aspect, the present disclosure provides a method of preparing a compound of Formula (I):

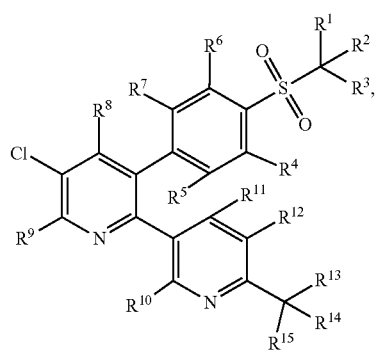

(I)

or a pharmaceutically acceptable salt, hydrate, solvate, polymorph, co-crystal, metabolite, or prodrug thereof, the method comprising:

(1) contacting a compound of Formula (A):

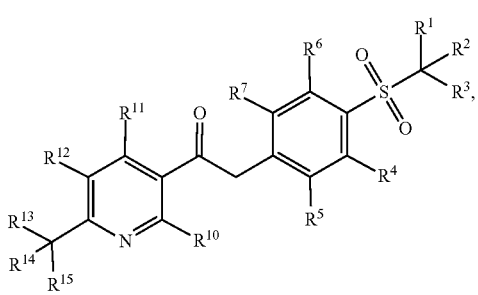

(A)

or a salt, hydrate, solvate, polymorph, or co-crystal thereof with one or more bases and a compound of Formula (B):

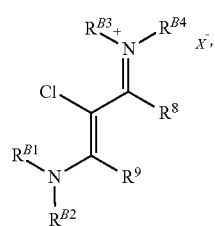

(B)

or a salt, hydrate, solvate, polymorph, or co-crystal thereof to produce a compound of Formula (II):

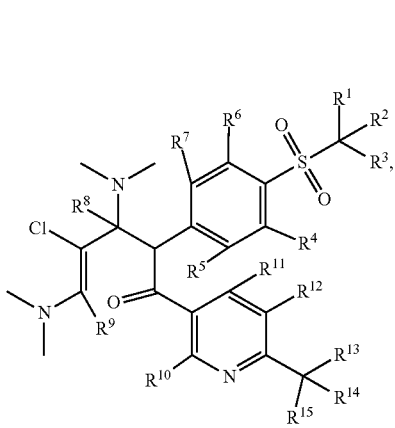

or a salt, hydrate, solvate, polymorph, or co-crystal thereof;
(2) contacting the compound of Formula (II), or a salt, hydrate, solvate, polymorph, or co-crystal thereof with one or more acids to produce a compound of Formula (III):

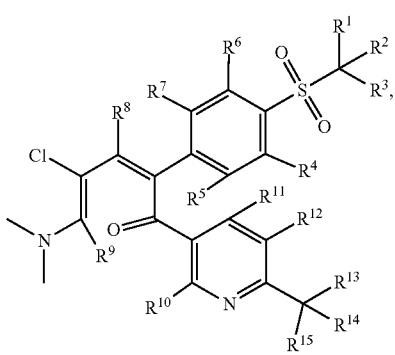

or a salt, hydrate, solvate, polymorph, or co-crystal thereof; and
(3) contacting the compound of Formula (III) with a source of nitrogen to produce the compound of Formula (I), or a pharmaceutically acceptable salt, hydrate, solvate, polymorph, or co-crystal thereof;

wherein:
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium;
each of $R^{B1}$, $R^{B2}$, $R^{B3}$, and $R^{B4}$ is independently optionally substituted alkyl; and
$X^-$ is an anion.

In another aspect, the present disclosure provides a method of preparing a compound of Formula (I):

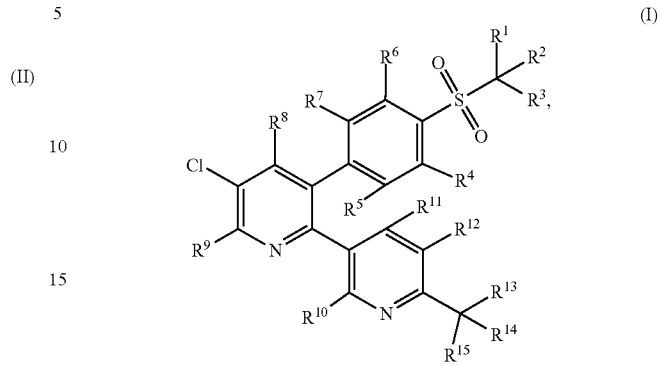

or a pharmaceutically acceptable salt, hydrate, solvate, polymorph, co-crystal, metabolite, or prodrug thereof, the method comprising:
(1) contacting a compound of Formula (C):

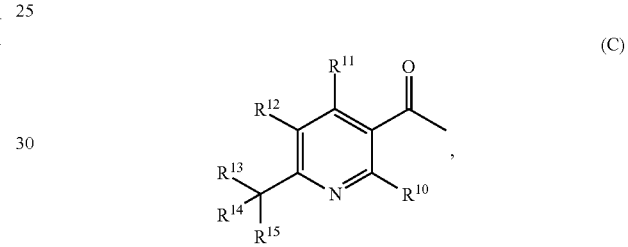

or a salt, hydrate, solvate, polymorph, or co-crystal thereof with a compound of Formula (D):

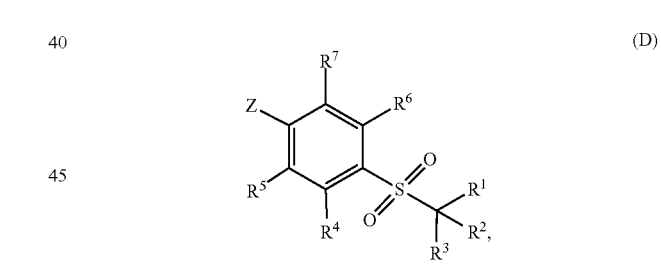

or a salt, hydrate, solvate, polymorph, or co-crystal thereof to produce a compound of Formula (A):

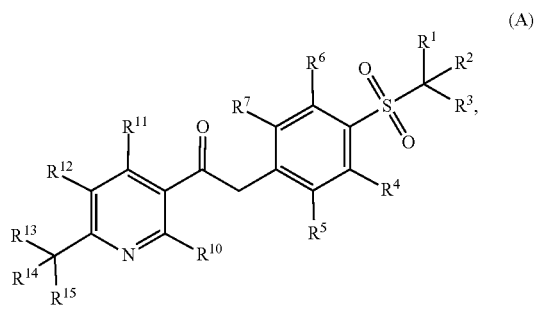

or a salt, hydrate, solvate, polymorph, or co-crystal thereof;
(2) contacting the compound of Formula (A), or a salt, hydrate, solvate, polymorph, or co-crystal thereof with one or more bases and a compound of Formula (B):

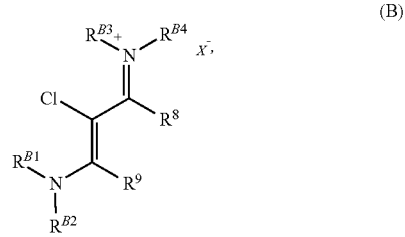
(B)

or a salt, hydrate, solvate, polymorph, or co-crystal thereof to produce a compound of Formula (II):

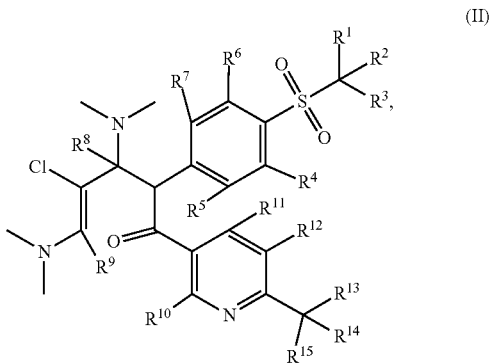
(II)

or a salt, hydrate, solvate, polymorph, or co-crystal thereof;
(3) contacting the compound of Formula (II), or a salt, hydrate, solvate, polymorph, or co-crystal thereof with one or more acids to produce a compound of Formula (III):

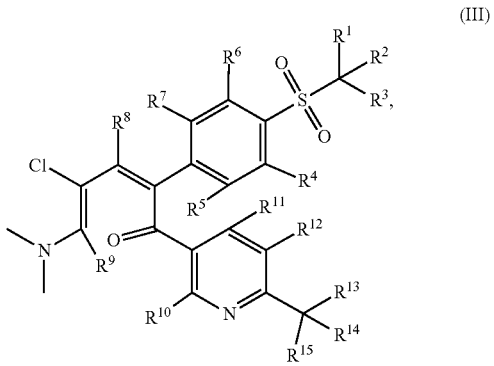
(III)

or a salt, hydrate, solvate, polymorph, or co-crystal thereof; and
(4) contacting the compound of Formula (III) with a source of nitrogen to produce the compound of Formula (I), or a pharmaceutically acceptable salt, hydrate, solvate, polymorph, or co-crystal thereof;
wherein:
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is independently hydrogen or deuterium, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is deuterium;
each of $R^{B1}$, $R^{B2}$, $R^{B3}$, and $R^{B4}$ is independently optionally substituted alkyl;
$X^-$ is an anion; and
Z is halogen.

In some embodiments, each of $R^{B1}$, $R^{B2}$, $R^{B3}$, and $R^{B4}$ is independently optionally substituted alkyl. In some embodiments, each of $R^{B1}$, $R^{B2}$, $R^{B3}$, and $R^{B4}$ is independently optionally substituted $C_{1-6}$ alkyl. In some embodiments, each of $R^{B1}$, $R^{B2}$, $R^{B3}$, and $R^{B4}$ is independently substituted $C_{1-6}$ alkyl. In some embodiments, each of $R^{B1}$, $R^{B2}$, $R^{B3}$, and $R^{B4}$ is independently unsubstituted $C_{1-6}$ alkyl. In some embodiments, each of $R^{B1}$, $R^{B2}$, $R^{B3}$, and $R^{B4}$ is independently methyl, ethyl, propyl, or butyl. In some embodiments, each of $R^{B1}$, $R^{B2}$, $R^{B3}$, and $R^{B4}$ is independently methyl, ethyl, or propyl. In some embodiments, each of $R^{B1}$, $R^{B2}$, $R^{B3}$, and $R^{B4}$ is independently methyl or ethyl. In some embodiments, each of $R^{B1}$, $R^{B2}$, $R^{B3}$, and $R^{B4}$ is methyl.

In some embodiments, $X^-$ is a non-coordinating anion. In some embodiments, $X^-$ is $-PF_6$. In some embodiments, $X^-$ is tetrafluoroborate. In some embodiments, $X^-$ is perchlorate.

In some embodiments, Z is Cl, Br, or I. In some embodiments, Z is Cl. In some embodiments, Z is Br. In some embodiments, Z is I.

In some embodiments, the step of contacting a compound of Formula (C) with a compound of Formula (D) is transition metal-catalyzed. In some embodiments, the step of contacting a compound of Formula (C) with a compound of Formula (D) is palladium-catalyzed. In some embodiments, the step of contacting a compound of Formula (C) with a compound of Formula (D) proceeds via enolate arylation. In some embodiments, the step of contacting a compound of Formula (C) with a compound of Formula (D) proceeds via transition metal-catalyzed enolate arylation. In some embodiments, the step of contacting a compound of Formula (C) with a compound of Formula (D) proceeds via palladium-catalyzed enolate arylation.

In some embodiments, the base is a strong base. In some embodiments, the base is a non-nucleophilic base. In some embodiments, the base is tert-butoxide salt. In some embodiments, the base is potassium tert-butoxide. In some embodiments, the base is sodium tert-butoxide. In some embodiments, the base is lithium diisopropylamide (LDA).

In some embodiments, the acid is an organic acid. In some embodiments, the acid is trifluoroacetic acid. In some embodiments, the acid is acetic acid. In some embodiments, the one or more acids are acetic acid and trifluoroacetic acid.

In some embodiments, one or more steps are performed in organic solvent. In some embodiments, one or more steps are performed in polar aprotic organic solvent. In some embodiments, one or more steps are performed in tetrahydrofuran. In some embodiments, the step of contacting a compound of Formula (A) with one or more bases is performed in tetrahydrofuran.

In some embodiments, the source of nitrogen is ammonia. In some embodiments, the source of nitrogen is an ammonium salt. In some embodiments, the source of nitrogen is ammonium hydroxide. In some embodiments, the source of nitrogen is ammonium acetate.

EXAMPLES

In order that the present disclosure may be more fully understood, the following examples are set forth. The synthetic and biological examples disclosed in this application are offered to illustrate the compounds, pharmaceutical compositions, and methods disclosed herein and are not to be construed in any way as limiting in their scope.

Abbreviations $AUC_{0-\infty}$ Area under the concentration-time curve from time zero extrapolated to infinity $AUC_{0-t}$ Area under the concentration-time curve from time zero to time t $C_{max}$ Maximum concentration observed HPLC High Performance/Pressure Liquid Chromatography LC/MS Liquid Chromatography Tandem Mass Spectrometry min Minute(s)

No. Number

SD Standard deviation $t_{1/2}$ Terminal half-life $T_{max}$ Time of observed maximum concentration Example 1

Synthesis of d3-Etoricoxib d3-Etoricoxib was synthesized according to the following synthetic scheme:

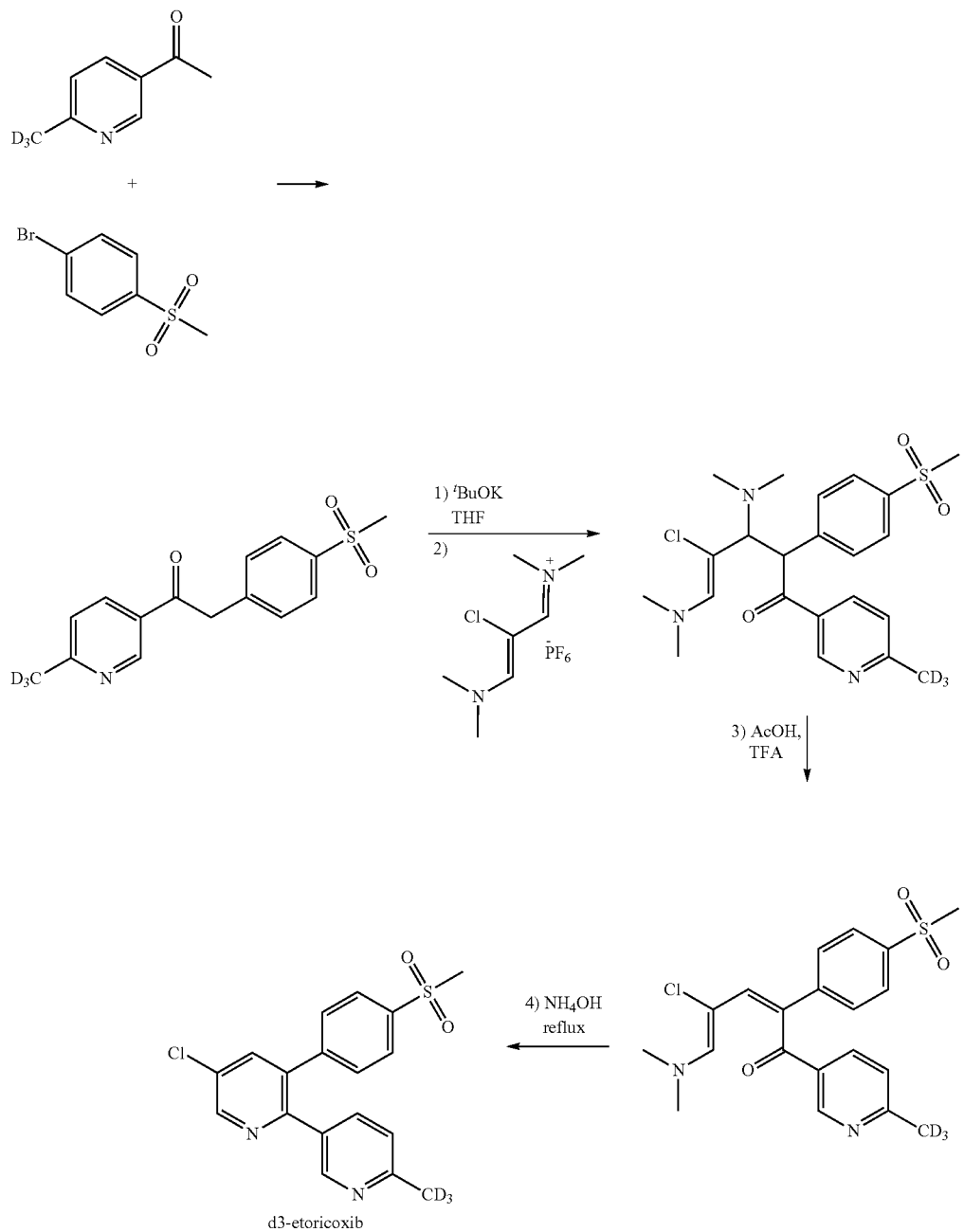

d3-etoricoxib

Figure 2:
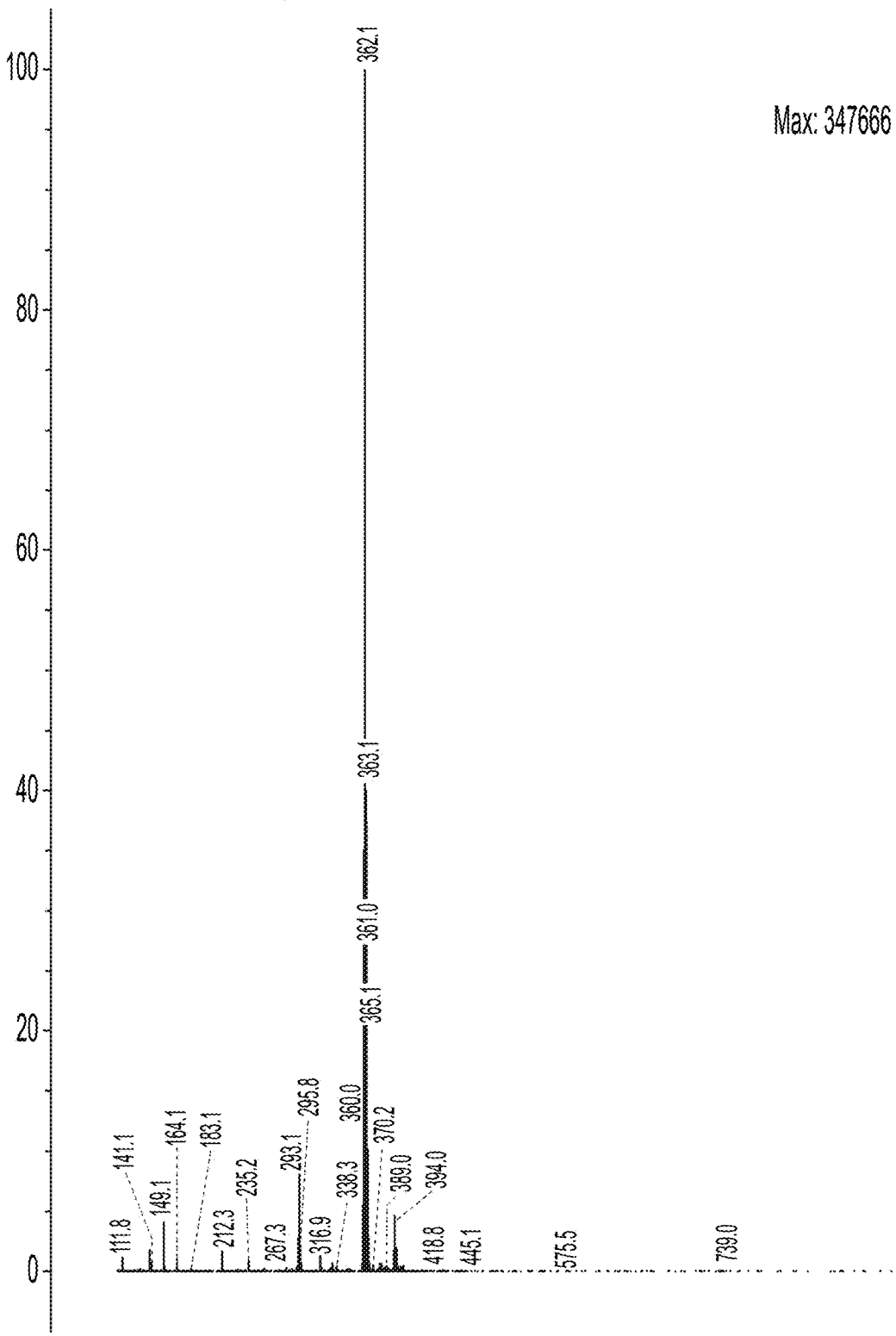
FIG. 2 shows a liquid chromatography/mass spectrometry ("LC/MS") mass spectrum of d3-etoricoxib.
Figure 3:
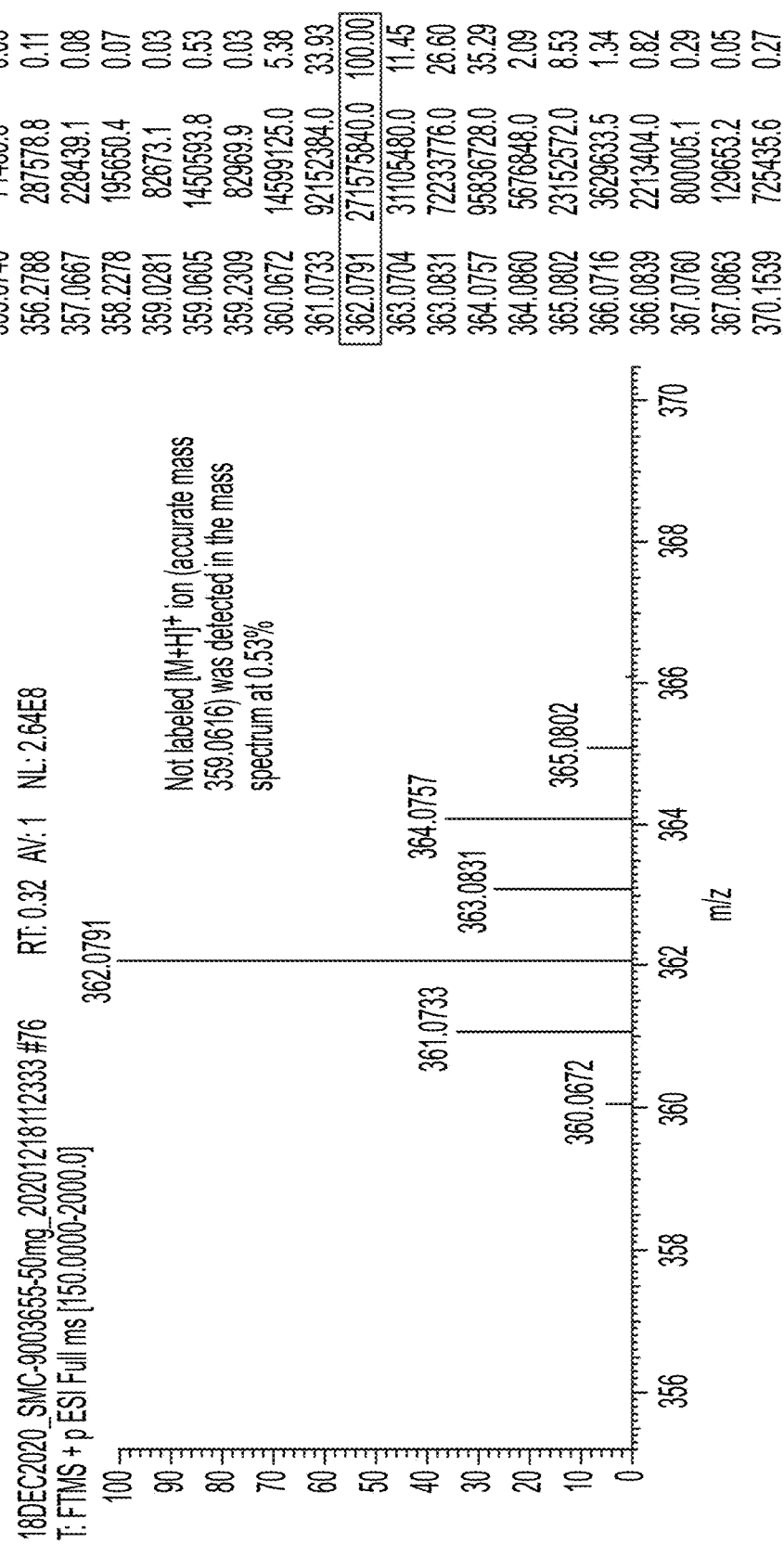
FIG. 3 shows an expanded view of an LC/MS mass spectrum of d3-etoricoxib.
Figure 4:
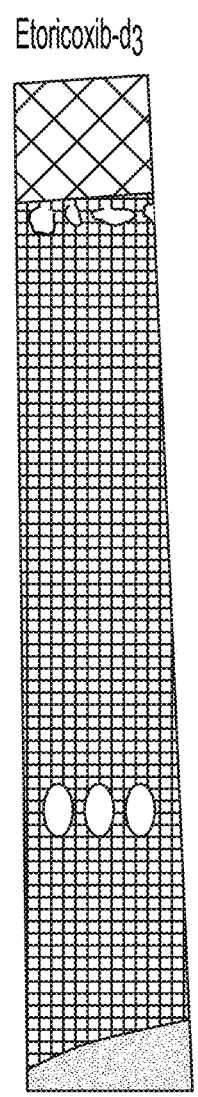
FIG. 4 shows a thin layer chromatography ("TLC") chromatogram of d3-etoricoxib.

Example 2 d3-Etoricoxib 50 mg Batch Analysis d3-Etoricoxib was prepared in a 50 mg batch (batch no. 0605175). HPLC (65:35:10 mM MeOH:H$_2$O:NH$_4$OAc, 1 mL/min, 210 nm): 94.1% purity, R$_t$ of 7.53 minutes (FIG. 1). LC/MS (MM-ES+APCl, Dual pos): m/z 362.1 (M+1), d0 detected at 0.53% (FIGS. 2 and 3). $^1$H NMR (methanol-d4, 400 MHz): δ8.71 (d, 1H, J=2.3 Hz), 8.27 (d, 1H, J=1.8 Hz), 8.00 (d, 1H, J=2.3 Hz), 7.9-7.9 (m, 2H, J=8.3 Hz), 7.67 (dd, 1H, J=2.3, 8.3 Hz), 7.4-7.5 (m, 2H, J=8.3 Hz), 7.23 (d, 1H, J=7.8 Hz), 3.1-3.1 (m, 3H). TLC (80:20 ethyl acetate: heptane): single spot, R$_f$ 0.21, visualized with UV (FIG. 4).

Figure 5:
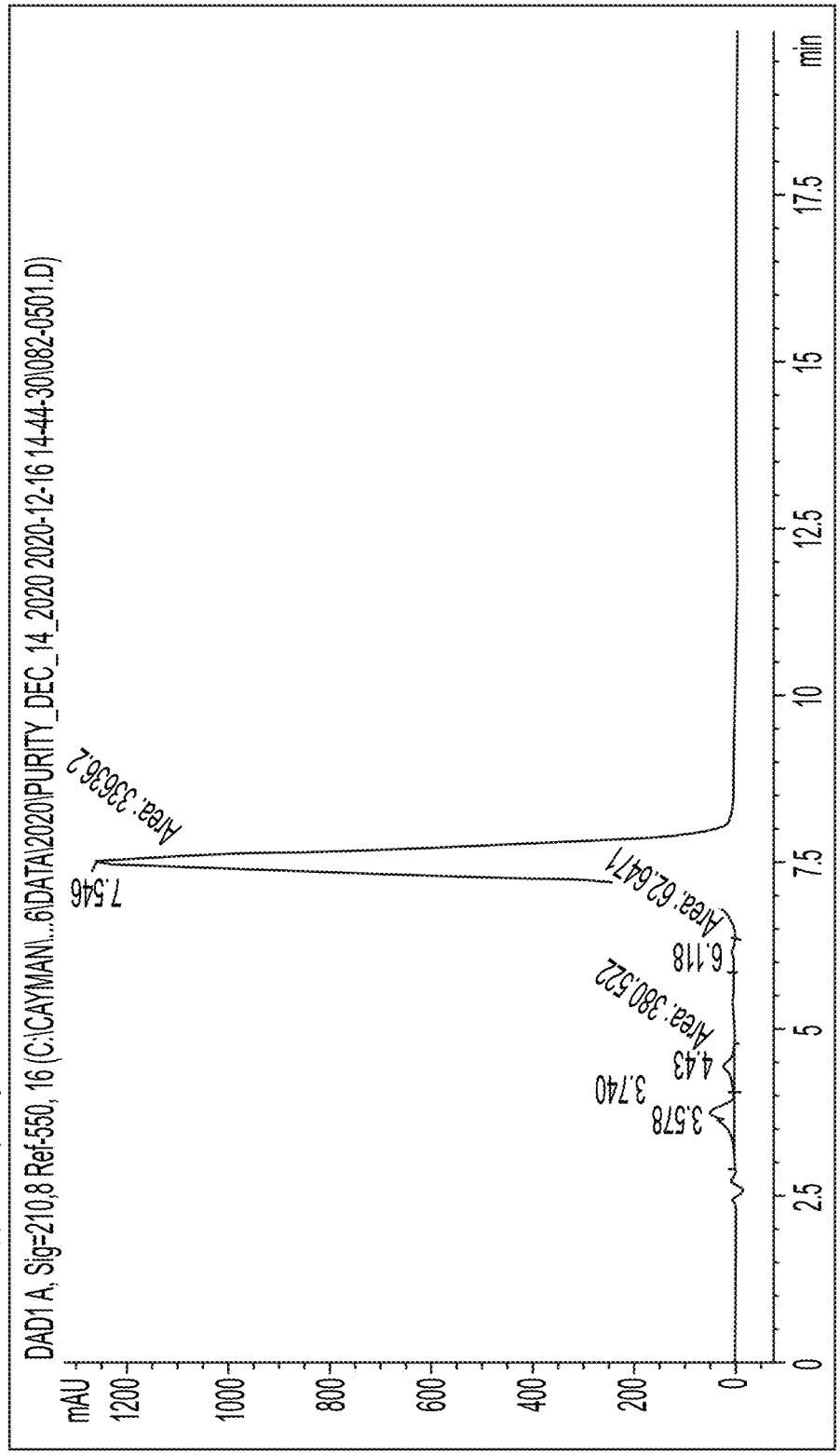
FIG. 5 shows an HPLC chromatogram of d3-etoricoxib.
Figure 6:
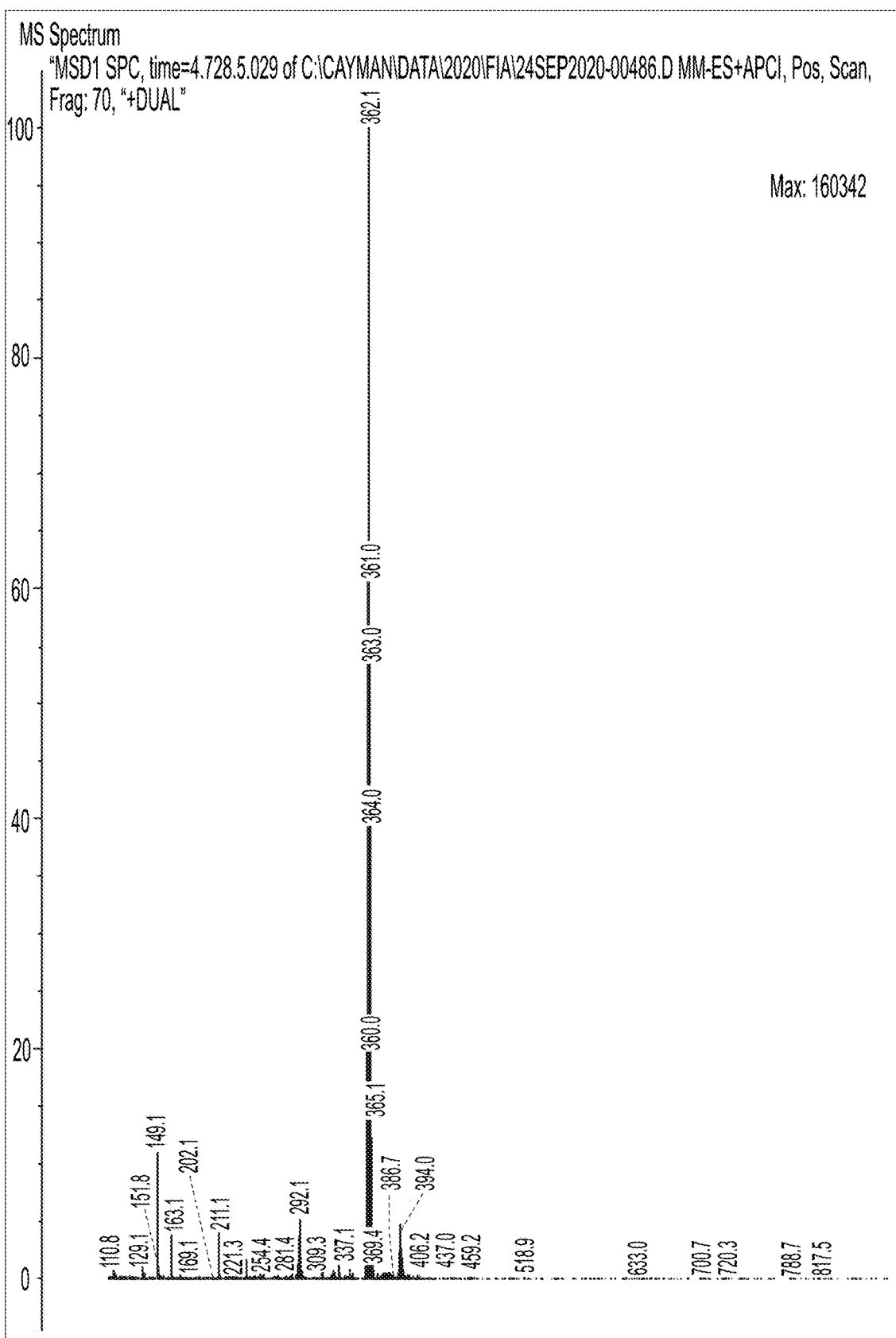
FIG. 6 shows an LC/MS mass spectrum of d3-etoricoxib.
Figure 7:
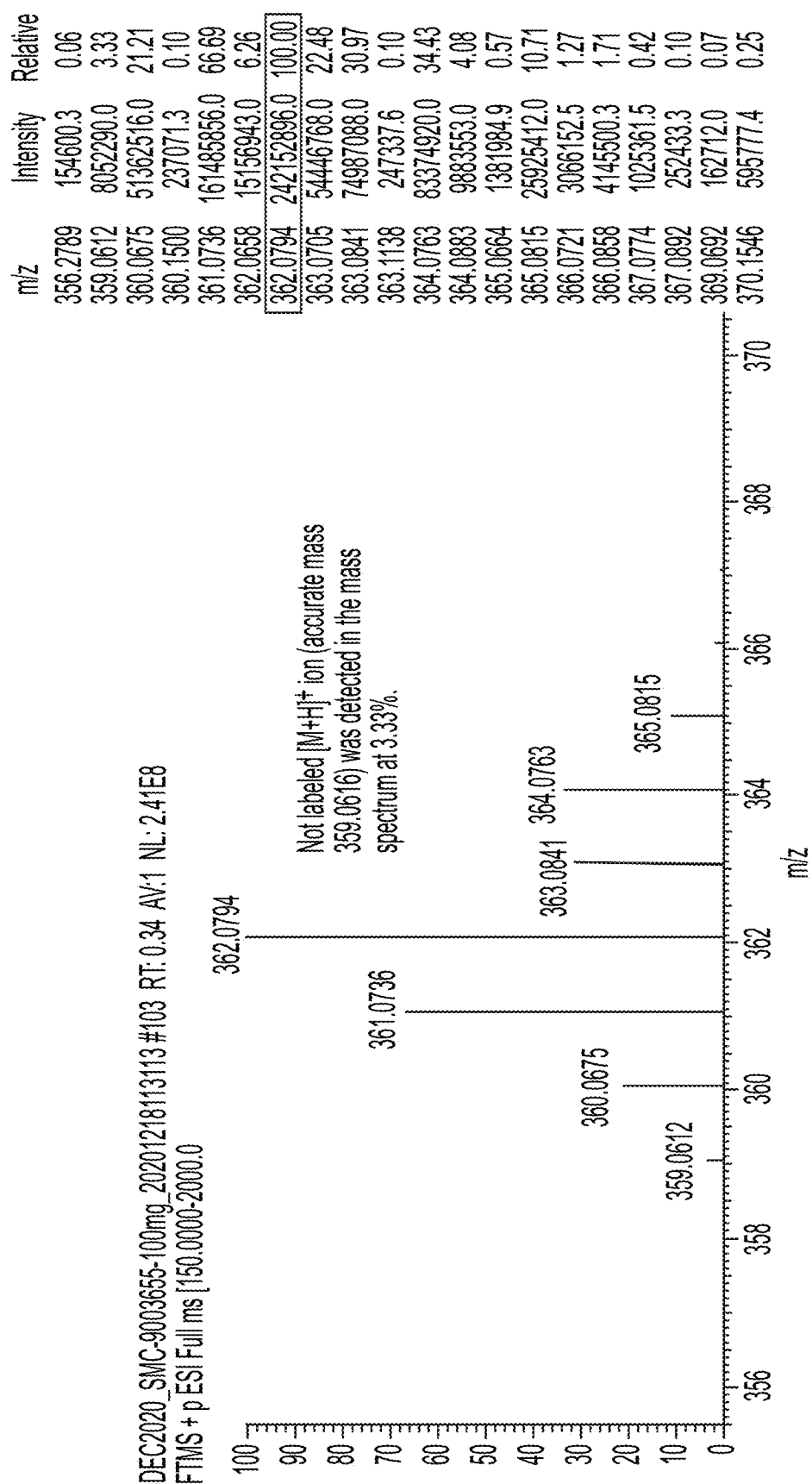
FIG. 7 shows an expanded view of an LC/MS mass spectrum of d3-etoricoxib.
Figure 8:
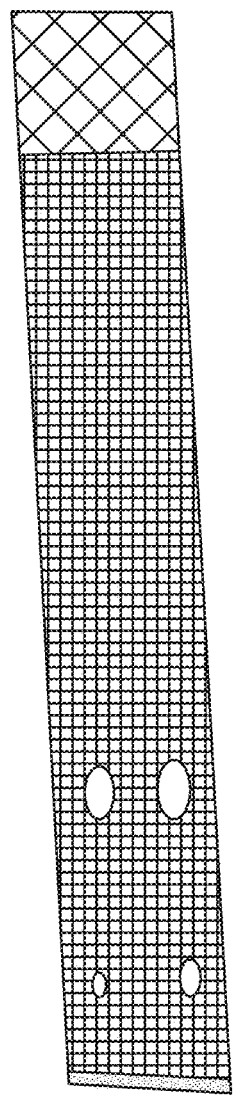
FIG. 8 shows a TLC of d3-etoricoxib.

Example 3 d3-Etoricoxib 100 mg Batch Analysis d3-Etoricoxib was prepared in a 100 mg batch (batch no. 0605176). HPLC (65:35:10 mM MeOH:H$_2$O:NH$_4$OAc, 1 mL/min, 210 nm): 96.2% purity, R$_t$ of 7.55 minutes (FIG. 5). LC/MS (MM-ES+APCl, Dual pos): m/z 362.1 (M+1), d0 detected at 3.33% (FIGS. 6 and 7). $^1$H NMR (methanol-d4, 400 MHz): δ8.71 (d, 1H, J=2.3 Hz), 8.27 (d, 1H, J=2.3 Hz), 8.00 (d, 1H, J=2.3 Hz), 7.91 (d, 2H, J=8.7 Hz), 7.67 (dd, 1H, J=2.3, 8.3 Hz), 7.50 (m, 2H, J=8.0 Hz), 7.23 (d, 1H, J=8.3 Hz), 3.1-3.1 (m, 3H). TLC (80:20 ethyl acetate:heptane): single spot, R$_f$ 0.21, visualized with UV (FIG. 8).

Example 4

Single Dose Crossover Study

A single dose crossover study was conducted to compare the pharmacokinetics of d3-etoricoxib and non-isotopically enriched etoricoxib in dogs. Four male dogs were dosed, and animals received each of the following treatments sequentially, with a minimum of four days washout between doses. The doses are summarized in Table 1.

TABLE 1

Doses of d3-etoricoxib and etoricoxib administered to four male dogs in a crossover study.

| Study Day | Dose Level | Compound | Route of Administration | Vehicle/Presentation |
|---|---|---|---|---|
| 1 | 2.00 mg/kg | d3-etoricoxib | oral (gavage) | 1% methylcellulose in water |
| 8 | 1.98 mg/kg | etoricoxib | oral (gavage) | 1% methylcellulose in water |

Blood samples were taken at 0.083, 0.25, 0.5, 1, 2, 4, 6, 8, 12, and 24 hours post-dose. Plasma was analyzed for d3-etoricoxib or non-isotopically enriched etoricoxib concentration. Results are summarized in Table 2.

TABLE 2

Pharmacokinetic parameters of d3-etoricoxib and etoricoxib administered to four male dogs in a crossover study.

| | $C_{max}$ (ng/mL) | | AUC$_{0.5-24\ h}$ (ng*h/mL) | |
|---|---|---|---|---|
| Animal | d3-etoricoxib | etoricoxib | d3-etoricoxib | etoricoxib |
| 1001 | 628 | 259 | 516 | 342 |
| 1002 | 791 | 426 | 1024 | 606 |
| 1003 | 593 | 670 | 1264 | 1131 |
| 1004 | 317 | 206 | 658 | 336 |
| Mean (SD) | 604 (373) | 390 (209) | 865 (341) | 582 (197) |
| Average % delta d3-etoricoxib vs etoricoxib | +54.9% | N/A | +48.6% | N/A |

Figure 9:
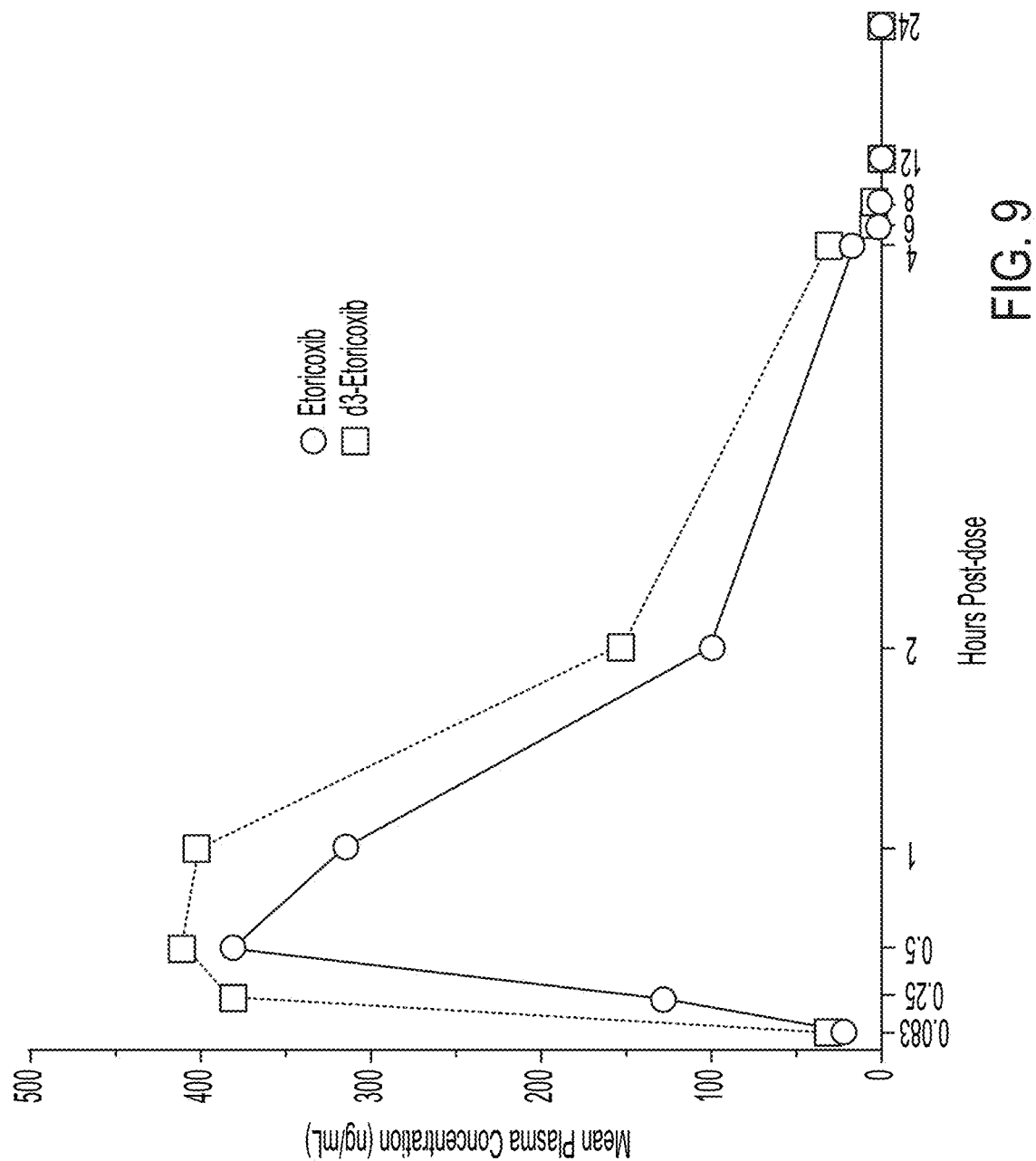
FIG. 9 shows a comparison of the mean plasma concentration (ng/mL) of etoricoxib (black trace) and d3-etoricoxib (grey trace) over 24 hours following administration to a population of dogs.
Figure 10A:
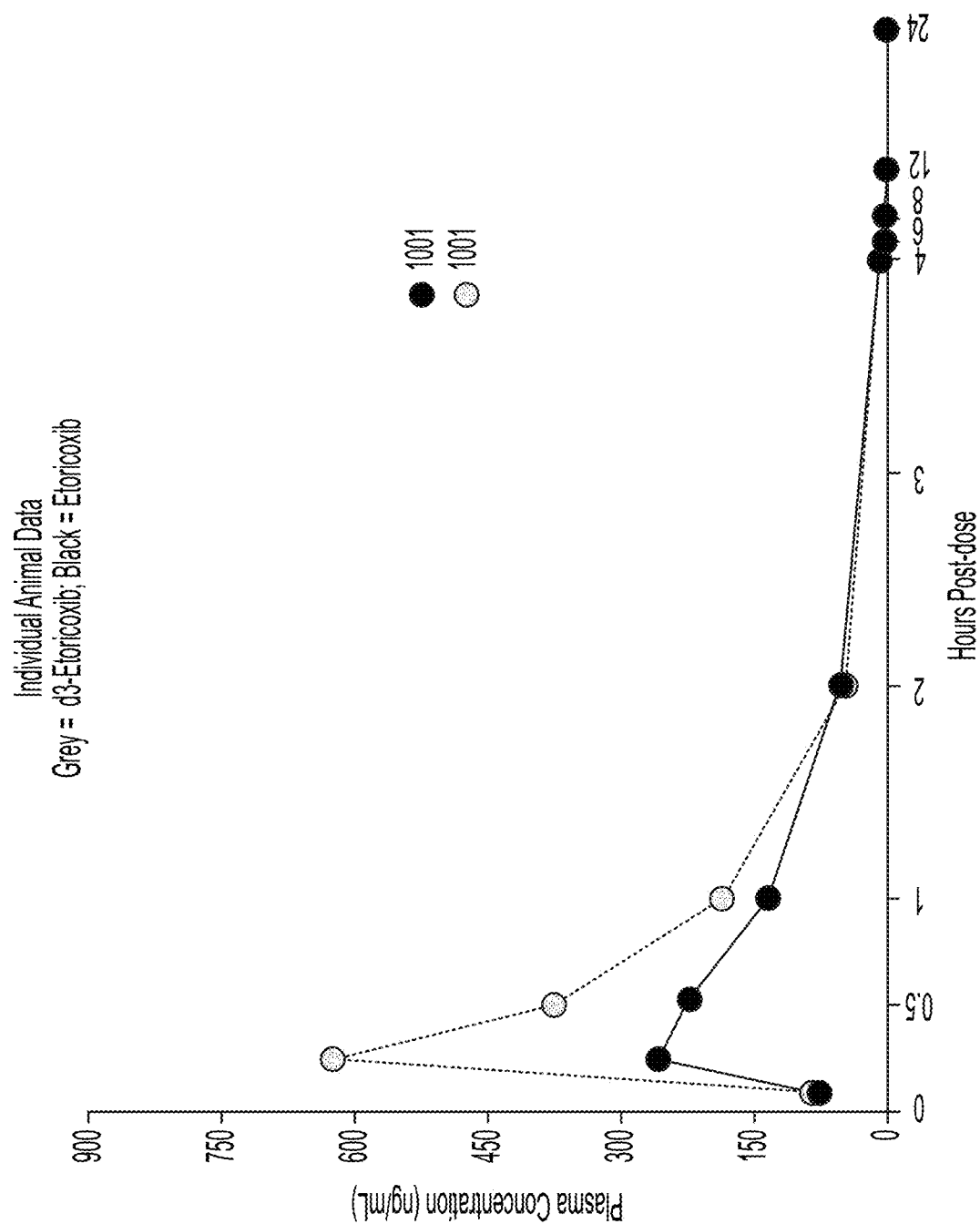
Figure 10B:
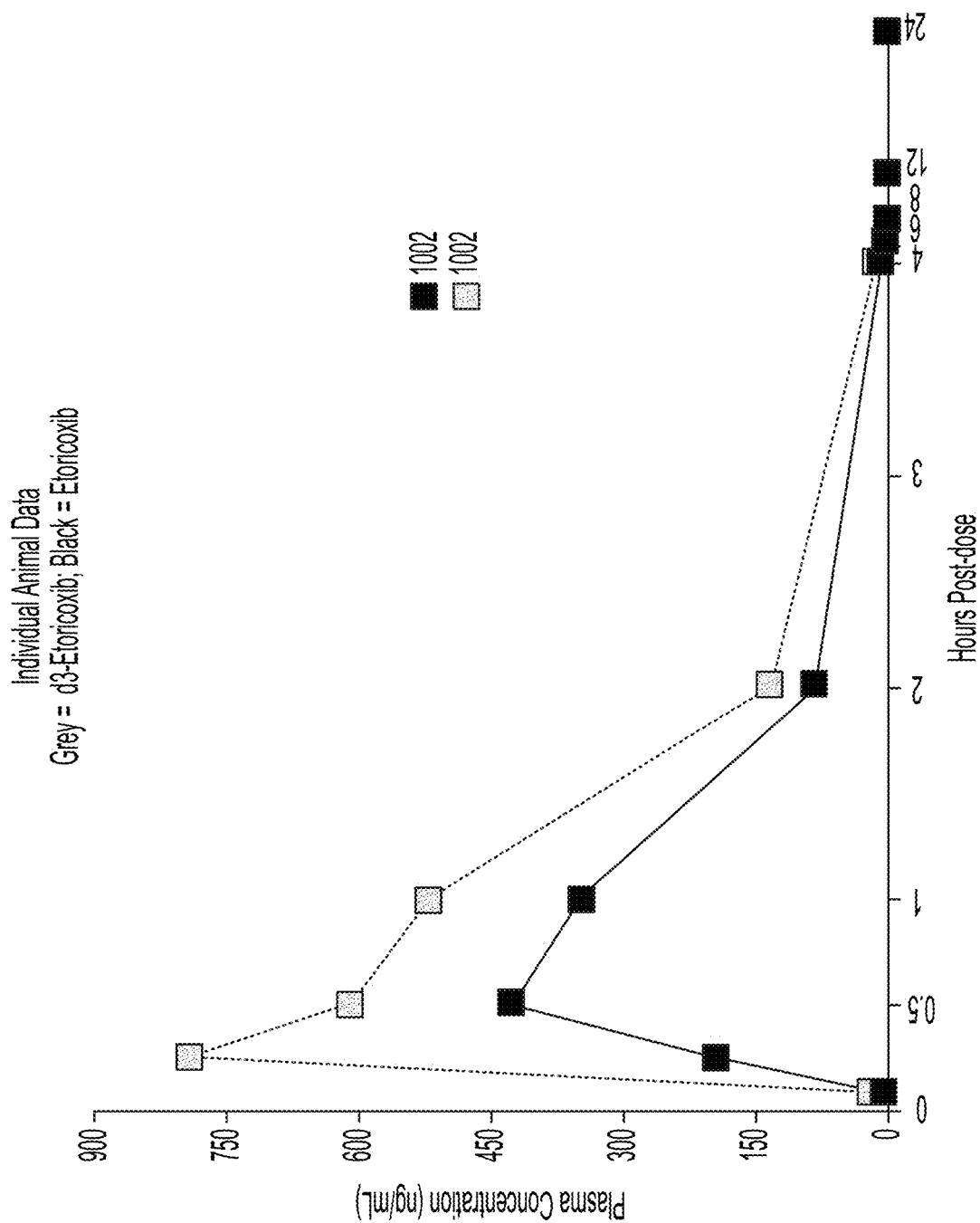
Figure 10C:
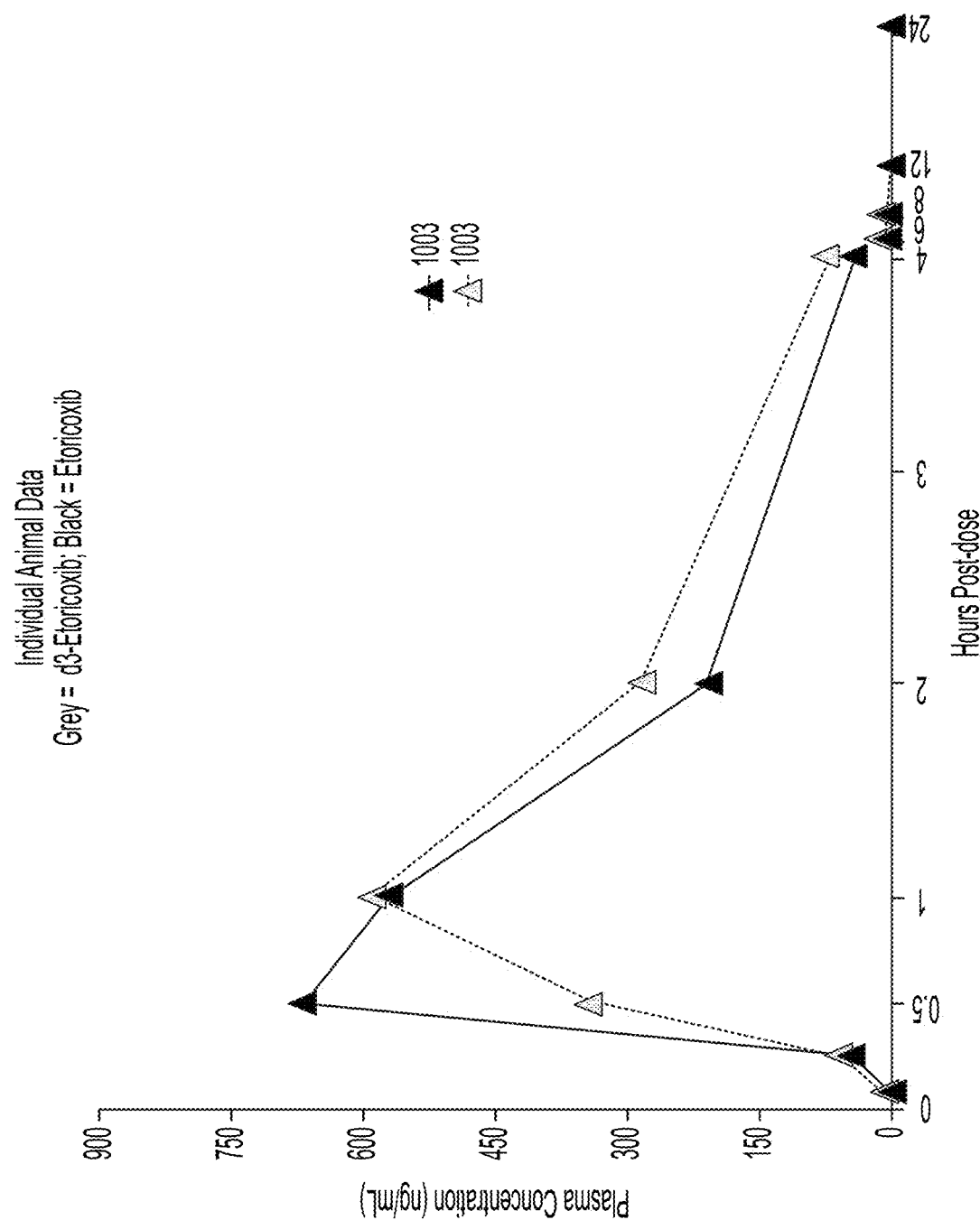

A comparison of the mean plasma concentration (ng/mL) of etoricoxib and d3-etoricoxib over 24 hours following administration of etoricoxib (1.98 mg/kg) or d3-etoricoxib (2.00 mg/kg) to a population of four male dogs is shown in FIG. 9. Individual mean plasma concentrations (ng/mL) of etoricoxib and d3-etoricoxib over 24 hours following administration of etoricoxib (1.98 mg/kg) or d3-etoricoxib (2.00 mg/kg) to each of four male dogs is shown in FIGS. 10A-D. These results demonstrate that, at equivalent doses, d3-etoricoxib is substantially resistant to metabolism in dogs relative to non-isotopically enriched etoricoxib and that this separation occurs almost immediately, resulting in not only higher total exposure (AUC) to d3-etoricoxib, but also a higher $C_{max}$, relative to non-isotopically enriched etoricoxib.

Example 5

In Vitro Metabolic Studies of Etoricoxib and d3-Etoricoxib with Human Liver Microsomes The metabolic stability of non-isotopically enriched etoricoxib and d3-etoricoxib, with human liver microsomes was evaluated. Assay conditions are summarized in Table 3.

TABLE 3

Metabolic Stability with Human Liver Microsomes - Assay Conditions

| | |
|---|---|
| Study species: | Human |
| Incubation volume: | 300 μL, pH 7.4 in phosphate buffer, 2 mM MgCl$_2$ |
| Protein content: | 0.5 mg/mL |
| Cofactors & concentrations: | NADPH (1 mM) and UDPGA (1 mM) |
| DMSO content: | 0.5% |
| Preincubation time: | 10 min at 37° C. |
| Incubation times: | 0, 10, 20, 40, 60 min |
| Replicates: | 2 with cofactors, 1 without cofactor |
| Reaction started by: | Addition of study compound |
| Termination of incubations: | 2-fold volume of 75% acetonitrile |
| Storage of samples: | Immediate analysis |
| Test compound concentration: | 1 μM |

Etoricoxib is extensively metabolized in humans with <1% of a dose recovered in urine as the parent drug. The primary pathway for metabolism of etoricoxib in humans is through the production of the methylhydroxy metabolite of etoricoxib ("M1"). Metabolism of etoricoxib involves conversion primarily to the "M1" derivative, mainly (ca. 60%) by CYP3A4, with less contribution by CYPs 1A2, 2C9, 2C19 and 2D6 (ca. 40% collectively). See, e.g., Arcoxia® (etoricoxib) Australian Product Information, available at http://apps.medicines.org.au/files/mkparcox.pdf (last visited Apr. 9, 2021), the contents of which are herein incorporated by reference in their entirety. Production of the "M1"

metabolite and d3-etoricoxib ("d2-M1") was evaluated in this experiment throughout the incubation period.

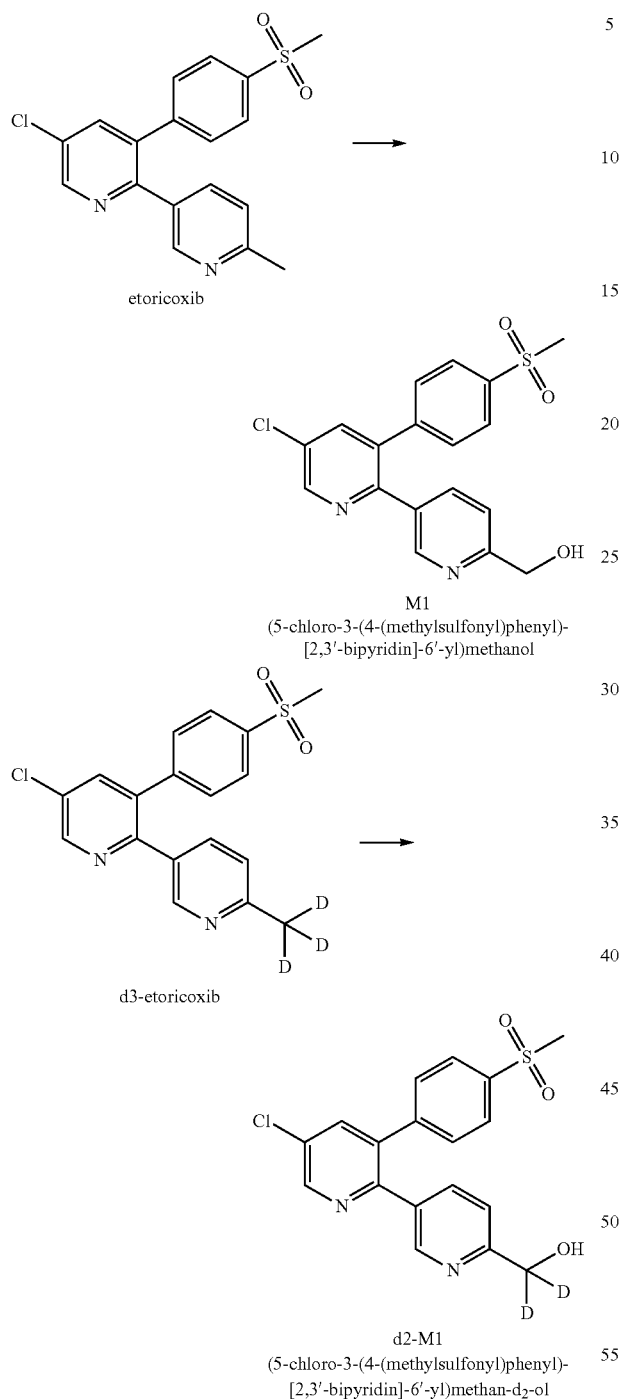

Figure 11:
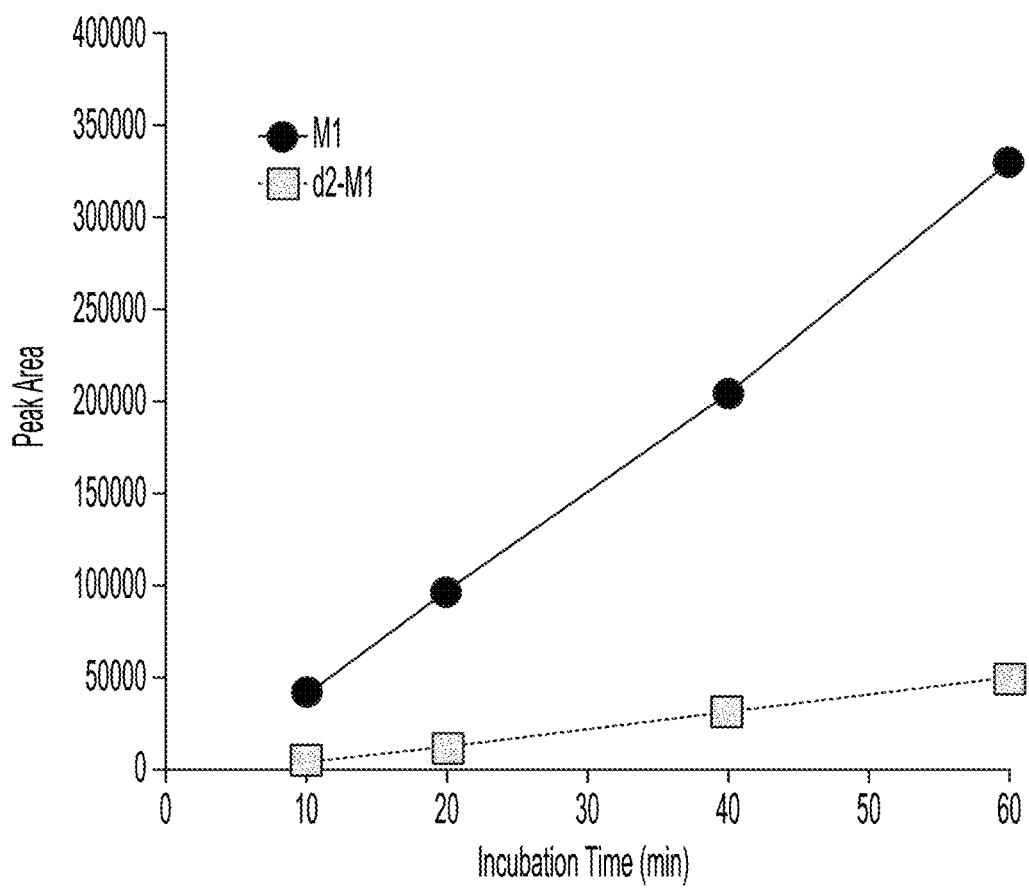
FIG. 11 shows peak area corresponding to the "d2-M1" and "M1" metabolites formed from d3-etoricoxib and etoricoxib over time on incubation with human liver microsomes in a microsomal stability assay.
Figure 12:
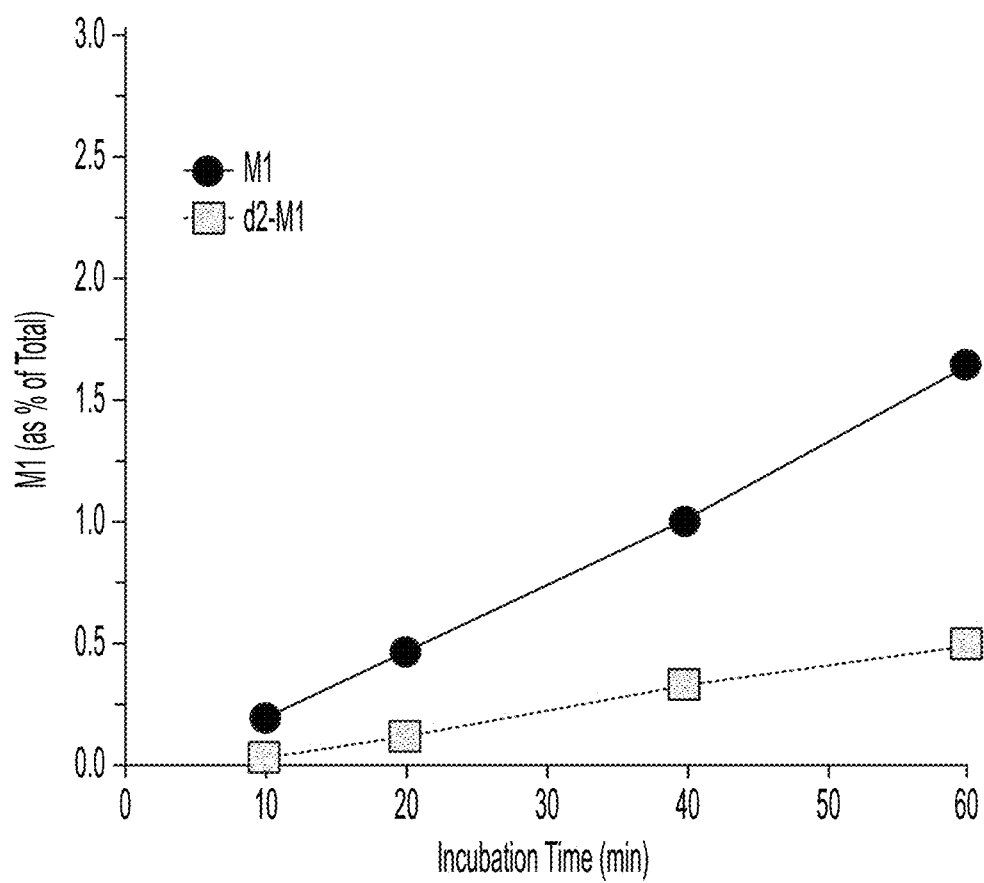
FIG. 12 shows percent total of "d2-M1" and "M1" metabolites formed from d3-etoricoxib and etoricoxib over time on incubation with human liver microsomes in a microsomal stability assay.

FIGS. 11-12 show peak area and relative percentage of parent corresponding to the "M1" and "d2-M1" metabolites formed from non-isotopically enriched etoricoxib and d3-etoricoxib over 60 minutes time on incubation with human liver microsomes in the microsomal stability assay, respectively. Under these conditions, approximately three-fold less of the "d2-M1" metabolite was formed from d3-etoricoxib than of "M1" formed from etoricoxib in this experiment, supporting the result demonstrated in dogs that d3-etoricoxib is resistant to the primary metabolic pathway in humans and dogs of conversion from parent to "d2-M1" relative to non-isotopically enriched etoricoxib and its respective conversion to "M1."

Example 6

In Vitro Metabolic Studies of Etoricoxib, d3-Etoricoxib, and d4-Etoricoxib in CYP3A4 Incubations The metabolic stability of non-isotopically enriched etoricoxib, d3-etoricoxib, and an alternate deuterated form of etoricoxib, d4-etoricoxib (5-chloro-6'-methyl-3-(4-(methylsulfonyl)phenyl-2,3,5,6-d4)-2,3'-bipyridine, CAS No.: 1131345-14-6), in CYP3A4 incubations was evaluated. d4-Etoricoxib has the chemical structure:

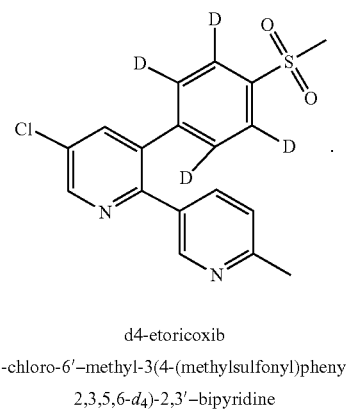

d4-etoricoxib
5-chloro-6'-methyl-3(4-(methylsulfonyl)phenyl-2,3,5,6-$d_4$)-2,3'-bipyridine Assay conditions are summarized in Table 4.

TABLE 4

Metabolic Stability of Etoricoxib, d3-Etoricoxib, and d4-Etoricoxib in CYP3A4 Incubations - Optimization Assay Conditions

| | |
|---|---|
| Study species: | Human recombinant CYP enzyme 3A4 |
| Buffer: | 0.1M phosphate buffer pH 7.4, 2 mM $MgCl_2$ |
| Spiking solvent: | 50% DMSO (1/100 to incubation) |
| Test compound concentration: | 1 μM |
| Protein content: | 100 μmol/mL |
| Cofactors: | NADPH (1 mM) |
| Incubation time: | 0, 10, 20, 30, and 40 min at 37° C |
| Replicates: | 2 |
| Termination of incubations: | 2-fold volume of cold 75% acetonitrile |
| Storage of samples: | Immediate analysis |

Human recombinant CYP3A4 (Corning, item #456202, lot #9322001) was chosen for the assay conditions as CYP3A4 is the principle enzyme responsible for the metabolism of etoricoxib in humans. Formation of the methylhydroxy metabolites formed from etoricoxib, d3-etoricoxib, and d4-etoricoxib was monitored over time (Table 5, FIGS. 13 and 14).

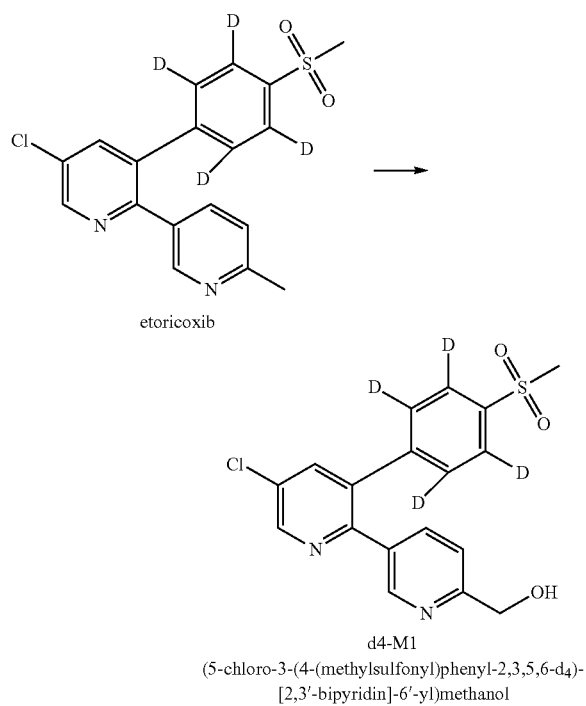

etoricoxib d4-M1
(5-chloro-3-(4-(methylsulfonyl)phenyl-2,3,5,6-d$_4$)-
[2,3'-bipyridin]-6'-yl)methanol

TABLE 5

Formation of M1 Metabolites Derived from Etoricoxib, d3-Etoricoxib,
and d4-Etoricoxib in CYP3A4 Incubations (100 pmol/mL)

| Incubation Time (min) | LC/MS Peak Area | | | % of Parent at Baseline | | |
|---|---|---|---|---|---|---|
| | Etoricoxib | d3-Etoricoxib | d4-Etoricoxib | Etoricoxib | d3-Etoricoxib | d4-Etoricoxib |
| 0 | — | — | — | — | — | — |
| 10 | 2,803,382 | 188,908 | 2,160,656 | 100 | 6.7 | 77.1 |
| 20 | 6,011,436 | 475,888 | 5,037,192 | 100 | 7.9 | 83.8 |
| 30 | 8,373,189 | 717,717 | 7,045,436 | 100 | 8.6 | 84.1 |
| 40 | 10,079,114 | 777,464 | 7,765,602 | 100 | 7.7 | 77.0 |

Figure 13:
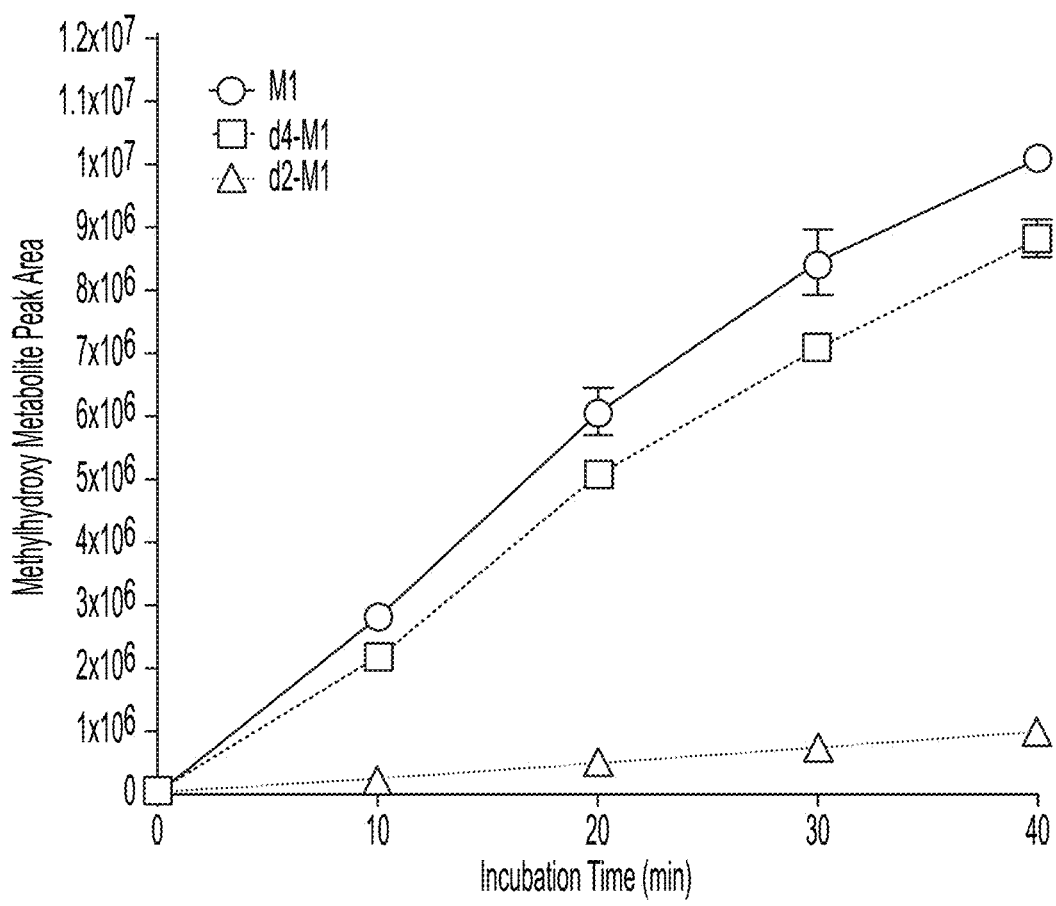
FIG. 13 shows peak area corresponding to the "M1," "d2-M1," and "d4-M1" metabolites formed from etoricoxib, d3-etoricoxib, and d4-etoricoxib over time on incubation with certain human recombinant CYP3A4 alleles in a microsomal stability assay.
Figure 14:
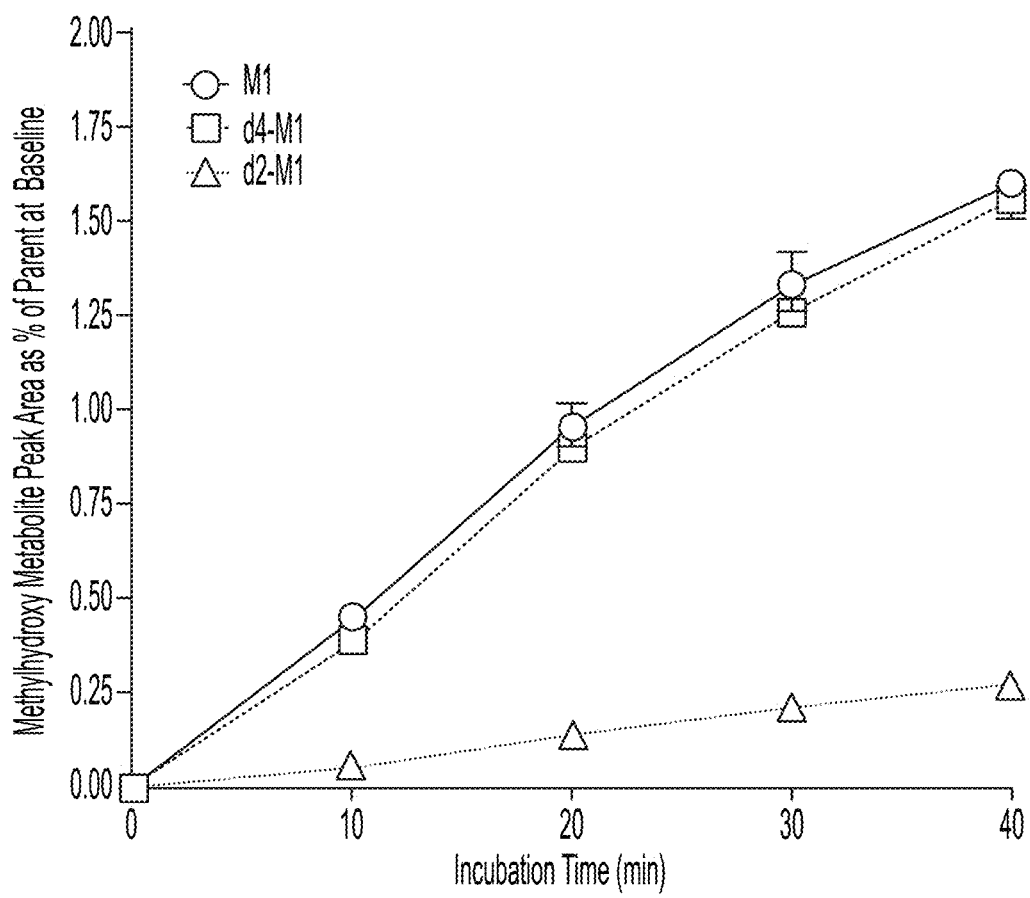
FIG. 14 shows percent total of "M1," "d2-M1," and "d4-M1" metabolites formed from etoricoxib, d3-etoricoxib, or d4-etoricoxib over time on incubation with certain human recombinant CYP3A4 alleles in a microsomal stability assay.

FIG. 13 shows peak area corresponding to the "M1," "d2-M1," and "d4-M1" metabolites formed from etoricoxib, d3-etoricoxib, and d4-etoricoxib over time on incubation with certain human recombinant CYP3A4 alleles. FIG. 14 shows percent total of "M1," "d2-M1," and "d4-M1" metabolites formed from etoricoxib, d3-etoricoxib, and d4-etoricoxib over time on incubation with certain human recombinant CYP3A4 alleles. Formation over time of "M1" formed from etoricoxib was similar to that of "d4-M1" formed from d4-etoricoxib. Formation of "d2-M1" formed from d3-etoricoxib was about six-fold lower than formation of "M1" formed from etoricoxib or "d4-M1" formed from d4-etoricoxib. Thus, despite containing less deuterium than d4-etoricoxib, d3-etoricoxib demonstrated a substantially different susceptibility to metabolism by CYP3A4, while d4-etoricoxib exhibited susceptibility to metabolism by CYP3A4 almost identical to non-isotopically enriched etoricoxib. These results demonstrate that deuteration, in and of itself, does not necessarily affect the metabolism of a particular molecule. The location of deuteration can greatly affect metabolic outcome and requires experimentation to determine what, if any, effects may occur

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Those skilled in the art will recognize or be able to ascertain using no more than routine experimentation many equivalents to the specific embodiments disclosed herein. The scope of the present embodiments disclosed herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for treating acute pain in a subject in need thereof, comprising administering to the subject a therapeutically effective amount of a compound of the formula:

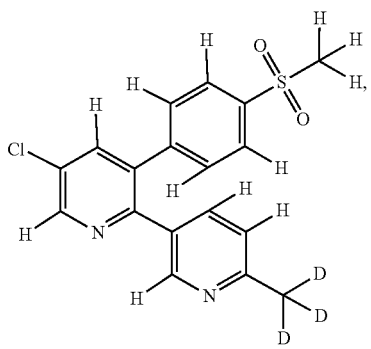

or a pharmaceutically acceptable salt, hydrate, solvate, polymorph, co-crystal, metabolite, or prodrug thereof, or a pharmaceutical composition thereof.

2. The method of claim 1, wherein the acute pain is caused by one or more of acute injury, trauma, illness, and surgery.

3. The method of claim 1, wherein the acute pain is one or more of headache, post-operative pain, pain caused by kidney stones, pain in the gall bladder, pain caused by stones in the gall bladder, birth pain, rheumatic pain, dental pain, pain due to sports injuries, carpal tunnel syndrome, burns, musculoskeletal sprains and strains, muscle tendon deformities, neck and shoulder pain, dyspepsia, gastric ulcer, duodenal ulcer, dysmenorrhea, and endometriosis.

4. The method of claim 1, wherein the subject is a mammal.

5. The method of claim 4, wherein the subject is a human.

6. The method of claim 5, wherein the subject is at least 16 years of age.

7. The method of claim 5, wherein the subject is at most 65 years of age.

8. The method of claim 1, wherein the therapeutically effective amount is administered to the subject once daily.

9. The method of claim 1, wherein the therapeutically effective amount is about 5 mg to about 300 mg.

10. The method of claim 1, wherein the pharmaceutical composition further comprises a pharmaceutically acceptable excipient.

11. The method of claim 10, wherein the pharmaceutical composition is an oral dosage form.

12. The method of claim 10, wherein the pharmaceutical composition is a parenteral, topical, buccal, ophthalmic, rectal, transdermal, or vaginal dosage form.

13. The method of claim 10, wherein the pharmaceutical composition is an injectable dosage form.

14. The method of claim 10, wherein the pharmaceutical composition is a solid dosage formulation.

15. The method of claim 14, wherein the solid dosage formulation is a tablet, capsule, granule, powder, sachet, or chewable dosage form.

16. The method of claim 10, wherein the pharmaceutical composition is a liquid dosage formulation.

17. The method of claim 16, wherein the liquid dosage formulation is a solution, suspension, or syrup.

18. The method of claim 16, wherein the pharmaceutical composition comprises about 1 mg/mL to about 60 mg/mL of the compound, or a pharmaceutically acceptable salt thereof.

19. The method of claim 1, wherein the compound has an isotopic purity of at least 90.0%.

20. The method of claim 19, wherein the compound has an isotopic purity of at least 95.0%.

21. The method of claim 20, wherein the compound has an isotopic purity of at least 97.0%.

22. The method of claim 21, wherein the compound has an isotopic purity of at least 99.0%.

23. The method of claim 1, further comprising administering to the subject ergotamine, an anti-inflammatory agent, a steroid, a barbiturate, an opioid analgesic, caffeine, or a combination thereof.

24. The method of claim 23, wherein the anti-inflammatory agent is a cyclooxygenase-2 (COX-2) inhibitor, a cyclooxygenase-3 (COX-3) inhibitor, a non-steroidal anti-inflammatory drug (NSAID), or a combination thereof.

25. The method of claim 24, wherein the NSAID is ibuprofen, naproxen, sulindac, ketoprofen, tolmetin, etodolac, fenoprofen, diclofenac, flurbiprofen, piroxicam, ketorolac, indomethacin, nabumetone, oxaprozin, mefanamic acid, diflunisal, or a combination thereof.

26. The method of claim 23, wherein the opioid analgesic is codeine, fentanyl, hydrocodone, hydromorphone, meperidine, methadone, morphine, oxycodone, or a combination thereof.

27. The method of claim 23, wherein the barbiturate is secobarbital, mephobarbital, pentobarbital, butabarbital, phenobarbital, amobarbital, or a combination thereof.

28. The method of claim 24, wherein the COX-2 inhibitor is celecoxib, valdecoxib, rofecoxib, or a combination thereof.

29. The method of claim 24, wherein the COX-3 inhibitor is acetaminophen, phenacetin, antipyrine, dipyrone, or a combination thereof.

30. The method of claim 1, wherein the method further comprises administering a loading dose of the compound and a maintenance dose of the compound.

31. The method of claim 3, wherein the dental pain is toothache.

* * * * *